(12) United States Patent
Watanabe et al.

(10) Patent No.: US 10,377,722 B2
(45) Date of Patent: Aug. 13, 2019

(54) ROSUVASTATIN CALCIUM AND PROCESS FOR PRODUCING INTERMEDIATE THEREOF

(71) Applicant: API CORPORATION, Tokyo (JP)

(72) Inventors: Naoyuki Watanabe, Fukuoka (JP); Tomoko Maeda, Kanagawa (JP); Yasumasa Dekishima, Kanagawa (JP); Hiroshi Kawabata, Kanagawa (JP); Masaki Nagahama, Fukuoka (JP); Kosuke Ito, Shizuoka (JP)

(73) Assignee: API CORPORATION, Tokyo (JP)

( * ) Notice: Subject to any disclaimer, the term of this patent is extended or adjusted under 35 U.S.C. 154(b) by 64 days.

(21) Appl. No.: 15/600,196

(22) Filed: May 19, 2017

(65) Prior Publication Data

US 2017/0305867 A1  Oct. 26, 2017

Related U.S. Application Data

(62) Division of application No. 15/116,861, filed as application No. PCT/JP2015/053436 on Feb. 6, 2015, now Pat. No. 9,695,130.

(30) Foreign Application Priority Data

| Feb. 6, 2014 | (JP) | 2014-021769 |
| Oct. 10, 2014 | (JP) | 2014-209142 |
| Oct. 10, 2014 | (JP) | 2014-209480 |

(51) Int. Cl.

| *C12P 7/42* | (2006.01) |
| *C12N 9/02* | (2006.01) |
| *C12N 9/04* | (2006.01) |
| *C07D 239/42* | (2006.01) |
| *C12P 17/12* | (2006.01) |

(52) U.S. Cl.

CPC ......... *C07D 239/42* (2013.01); *C12N 9/0006* (2013.01); *C12P 17/12* (2013.01); *C12Y 101/01184* (2013.01)

(58) Field of Classification Search

CPC .......... C12P 17/12; C12P 7/42; C12N 9/0006; C12Y 101/01184

USPC .............................. 435/189, 146, 128, 252.2

See application file for complete search history.

(56) References Cited

U.S. PATENT DOCUMENTS

| 5,260,440 | A | 11/1993 | Hirai et al. |
| 6,777,552 | B2 | 8/2004 | Niddam-Hildesheim et al. |
| 6,841,554 | B2 | 1/2005 | Taylor et al. |
| 6,965,031 | B2 | 11/2005 | Hara |
| 7,129,352 | B2 | 10/2006 | Taylor et al. |
| 7,335,757 | B2 | 2/2008 | Hiraoka et al. |
| 8,436,167 | B2 | 5/2013 | Booth et al. |
| 8,536,330 | B2 | 9/2013 | Pandya et al. |
| 9,371,291 | B2 | 6/2016 | Okada et al. |
| 2003/0045718 | A1 | 3/2003 | Taylor et al. |
| 2003/0114685 | A1 | 6/2003 | Niddam-Hildesheim et al. |
| 2004/0030139 | A1 | 2/2004 | Hara et al. |
| 2005/0048633 | A1 | 3/2005 | Hiraoka et al. |
| 2006/0014766 | A1 | 1/2006 | Taylor et al. |
| 2006/0293355 | A1 | 12/2006 | Booth et al. |
| 2007/0037979 | A1 | 2/2007 | Niddam-Hildesheim et al. |
| 2007/0167625 | A1 | 7/2007 | Balanov et al. |
| 2007/0255060 | A1 | 11/2007 | Okada et al. |
| 2008/0188657 | A1 | 8/2008 | Lenger |
| 2009/0111839 | A1 | 4/2009 | Zlicar et al. |
| 2010/0222373 | A1 | 9/2010 | Booth et al. |
| 2011/0301348 | A1 | 12/2011 | Okada et al. |
| 2012/0059022 | A1 | 3/2012 | Booth et al. |
| 2012/0149905 | A1 | 6/2012 | Mallela et al. |
| 2013/0150579 | A1 | 6/2013 | Pandya et al. |
| 2013/0225622 | A1 | 8/2013 | Booth et al. |

FOREIGN PATENT DOCUMENTS

| EP | 2 351 762 | 8/2011 |
| JP | 2648897 | 5/1997 |
| JP | 2008-521836 | 6/2008 |
| JP | 2008-546730 | 12/2008 |
| WO | 01/60804 | 8/2001 |
| WO | 02/063028 | 8/2002 |
| WO | 03/016317 | 2/2003 |
| WO | 03/078634 | 9/2003 |
| WO | 2005/023779 | 3/2005 |
| WO | 2005/042522 | 5/2005 |
| WO | 2008/065410 | 6/2008 |
| WO | 2010/047296 | 4/2010 |
| WO | 2011/021058 | 2/2011 |
| WO | 2011/132172 | 10/2011 |
| WO | 2012/063115 | 5/2012 |
| WO | 2012/176218 | 12/2012 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9).*
Rafeeq et al., "Process for Preparation of Statins and Novel Intermediates Thereof," IP.com, IP.com No. IPCOM000145623D, Jan. 19, 2007.
Rafeeq et al., "Processes for Preparation of Statins and Novel Intermediates Thereof," IP.com, IP.com No. IPCOM000144026D, Dec. 14, 2006.
Written Opinion of the International Searching Authority issued in PCT/JP2015/053436, dated Apr. 28, 2015.
International Search Report issued in PCT/JP2015/053436, dated Apr. 28, 2015.

* cited by examiner

*Primary Examiner* — Robert B Mondesi
*Assistant Examiner* — Mohammad Y Meah
(74) *Attorney, Agent, or Firm* — Greenblum & Bernstein, P.L.C.

(57) ABSTRACT

An object of the present invention is to provide a novel method capable of producing rosuvastatin calcium and intermediates therefor efficiently, inexpensively and with high purity. The present invention provides a method of efficiently producing rosuvastatin calcium and intermediates therefor having a high purity at an industrial scale, without using an extremely low temperature reaction or a special asymmetric catalyst.

3 Claims, 6 Drawing Sheets

Specification includes a Sequence Listing.

SEQUENCE LISTING

```
<160> NUMBER OF SEQ ID NOS: 10

<210> SEQ ID NO 1
<211> LENGTH: 753
<212> TYPE: DNA
<213> ORGANISM: Ogataea minuta var. nonfermentans
<220> FEATURE:
<221> NAME/KEY: CDS
<222> LOCATION: (1)..(753)

<400> SEQUENCE: 1 atg gct aaa act gtt tac ttc atc gca ggt gct tcc aga ggt atc ggt      48
Met Ala Lys Thr Val Tyr Phe Ile Ala Gly Ala Ser Arg Gly Ile Gly
1               5                   10                  15 ctc gag gtt gct tcc cag ctg agt gca aac cca gac aat tat gtt att      96
Leu Glu Val Ala Ser Gln Leu Ser Ala Asn Pro Asp Asn Tyr Val Ile
            20                  25                  30 gca tcc tat aga tct gaa aag tct gct tca gga ctt ttg gag ctg gca     144
Ala Ser Tyr Arg Ser Glu Lys Ser Ala Ser Gly Leu Leu Glu Leu Ala
        35                  40                  45 aag aag gat aat gtc gac aca att gtg ttg gat att gca agc cag gaa     192
Lys Lys Asp Asn Val Asp Thr Ile Val Leu Asp Ile Ala Ser Gln Glu
    50                  55                  60 tcg att gat gct gtt cca gca cag att tcc aag ctg act gat gga atc     240
Ser Ile Asp Ala Val Pro Ala Gln Ile Ser Lys Leu Thr Asp Gly Ile
65                  70                  75                  80 gat gtt gcc ttg atc aac gct gga att gcc aac gct atg tgt ccg att     288
Asp Val Ala Leu Ile Asn Ala Gly Ile Ala Asn Ala Met Cys Pro Ile
                85                  90                  95
```

```
ctc gaa tgt tct aga gag tcc tac act gat cac tgg aca acc aat gcc      336
Leu Glu Cys Ser Arg Glu Ser Tyr Thr Asp His Trp Thr Thr Asn Ala
            100                 105                 110 ttg ggt cca atc atg ctc tac caa gct att cat aag ttc atg ctc cag      384
Leu Gly Pro Ile Met Leu Tyr Gln Ala Ile His Lys Phe Met Leu Gln
        115                 120                 125 aga gag acc aga aaa gtg ttc ttt acc acg agt gct ggt ggt tcc att      432
Arg Glu Thr Arg Lys Val Phe Phe Thr Thr Ser Ala Gly Gly Ser Ile
    130                 135                 140 cag gct aag ata ccc gtg cct gtg agt ggt tac ggt atg tcc aag gct      480
Gln Ala Lys Ile Pro Val Pro Val Ser Gly Tyr Gly Met Ser Lys Ala
145                 150                 155                 160 gcg ctt aat tat gct gtg aga aaa ctt gct gac gag tgc tac aag gac      528
Ala Leu Asn Tyr Ala Val Arg Lys Leu Ala Asp Glu Cys Tyr Lys Asp
                165                 170                 175 aac ttc act att gtg ttg ctg cat cct ggt ttt gtt aag acg gac atg      576
Asn Phe Thr Ile Val Leu Leu His Pro Gly Phe Val Lys Thr Asp Met
            180                 185                 190 ggt caa agc gcc att cag aag atg tca aat gga aat gct gag ctt ctt      624
Gly Gln Ser Ala Ile Gln Lys Met Ser Asn Gly Asn Ala Glu Leu Leu
        195                 200                 205 gct tac att gac tca atg act att gat gtt cct acc agt gct ggc caa      672
Ala Tyr Ile Asp Ser Met Thr Ile Asp Val Pro Thr Ser Ala Gly Gln
    210                 215                 220 atc gtc ggt gcc att atg acc ttg gac aag cag agc agc ggt aga ttt      720
Ile Val Gly Ala Ile Met Thr Leu Asp Lys Gln Ser Ser Gly Arg Phe
225                 230                 235                 240 atc aac gct gct gac cag ttt gac atg cca ttt                          753
Ile Asn Ala Ala Asp Gln Phe Asp Met Pro Phe
                245                 250

<210> SEQ ID NO 2
<211> LENGTH: 251
<212> TYPE: PRT
<213> ORGANISM: Ogataea minuta var. nonfermentans

<400> SEQUENCE: 2

Met Ala Lys Thr Val Tyr Phe Ile Ala Gly Ala Ser Arg Gly Ile Gly
1               5                   10                  15

Leu Glu Val Ala Ser Gln Leu Ser Ala Asn Pro Asp Asn Tyr Val Ile
            20                  25                  30

Ala Ser Tyr Arg Ser Glu Lys Ser Ala Ser Gly Leu Leu Glu Leu Ala
        35                  40                  45

Lys Lys Asp Asn Val Asp Thr Ile Val Leu Asp Ile Ala Ser Gln Glu
    50                  55                  60

Ser Ile Asp Ala Val Pro Ala Gln Ile Ser Lys Leu Thr Asp Gly Ile
65                  70                  75                  80

Asp Val Ala Leu Ile Asn Ala Gly Ile Ala Asn Ala Met Cys Pro Ile
                85                  90                  95

Leu Glu Cys Ser Arg Glu Ser Tyr Thr Asp His Trp Thr Thr Asn Ala
            100                 105                 110

Leu Gly Pro Ile Met Leu Tyr Gln Ala Ile His Lys Phe Met Leu Gln
        115                 120                 125

Arg Glu Thr Arg Lys Val Phe Phe Thr Thr Ser Ala Gly Gly Ser Ile
    130                 135                 140

Gln Ala Lys Ile Pro Val Pro Val Ser Gly Tyr Gly Met Ser Lys Ala
145                 150                 155                 160
```

```
Ala Leu Asn Tyr Ala Val Arg Lys Leu Ala Asp Glu Cys Tyr Lys Asp
            165                 170                 175

Asn Phe Thr Ile Val Leu Leu His Pro Gly Phe Val Lys Thr Asp Met
        180                 185                 190

Gly Gln Ser Ala Ile Gln Lys Met Ser Asn Gly Asn Ala Glu Leu Leu
            195                 200                 205

Ala Tyr Ile Asp Ser Met Thr Ile Asp Val Pro Thr Ser Ala Gly Gln
        210                 215                 220

Ile Val Gly Ala Ile Met Thr Leu Asp Lys Gln Ser Ser Gly Arg Phe
225                 230                 235                 240

Ile Asn Ala Ala Asp Gln Phe Asp Met Pro Phe
            245                 250

<210> SEQ ID NO 3
<211> LENGTH: 29
<212> TYPE: DNA
<213> ORGANISM: Artificial Sequence
<220> FEATURE:
<223> OTHER INFORMATION: PCR primer

<400> SEQUENCE: 3
cggaattcat ggctaaaact gtttacttc                              29

<210> SEQ ID NO 4
<211> LENGTH: 35
<212> TYPE: DNA
<213> ORGANISM: Artificial Sequence
<220> FEATURE:
<223> OTHER INFORMATION: PCR primer

<400> SEQUENCE: 4
gggaagctta ttactaaaat ggcatgtcaa actgg                       35

<210> SEQ ID NO 5
<211> LENGTH: 783
<212> TYPE: DNA
<213> ORGANISM: Bacillus subtilis
<220> FEATURE:
<221> NAME/KEY: CDS
<222> LOCATION: (1)..(783)

<400> SEQUENCE: 5 atg tat ccg gat tta aaa gga aaa gtc gtc gct att aca gga gct gct    48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca    96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta   144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga   192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att   240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gca   288
Lys Glu Phe Gly Thr Leu Asp Ile Met Ile Asn Asn Ala Gly Leu Ala
                85                  90                  95
```

| | | | | | | | | | | | | | | | |
|---|---|---|---|---|---|---|---|---|---|---|---|---|---|---|---|
| aat | cct | gtg | cca | tct | cac | gaa | atg | ccg | ctc | aag | gat | tgg | gat | aaa | gtc | 336 |
| Asn | Pro | Val | Pro | Ser | His | Glu | Met | Pro | Leu | Lys | Asp | Trp | Asp | Lys | Val |
| | | | 100 | | | | | 105 | | | | | 110 | | |
| atc | ggc | acg | aac | tta | acg | ggt | gcc | ttt | tta | gga | agc | cgt | gaa | gcg | att | 384 |
| Ile | Gly | Thr | Asn | Leu | Thr | Gly | Ala | Phe | Leu | Gly | Ser | Arg | Glu | Ala | Ile |
| | | | | 115 | | | | | 120 | | | | | 125 | |
| aaa | tat | ttc | gta | gaa | aac | gat | atc | aag | gga | aat | gtc | att | aac | atg | tcc | 432 |
| Lys | Tyr | Phe | Val | Glu | Asn | Asp | Ile | Lys | Gly | Asn | Val | Ile | Asn | Met | Ser |
| | 130 | | | | | 135 | | | | | 140 | | | | |
| agt | gtg | cac | gaa | gtg | att | cct | tgg | ccg | tta | ttt | gtc | cac | tat | gcg | gca | 480 |
| Ser | Val | His | Glu | Val | Ile | Pro | Trp | Pro | Leu | Phe | Val | His | Tyr | Ala | Ala |
| 145 | | | | | 150 | | | | | 155 | | | | | 160 |
| agt | aaa | ggc | ggg | ata | aag | ctg | atg | aca | gaa | aca | tta | gcg | ttg | gaa | tac | 528 |
| Ser | Lys | Gly | Gly | Ile | Lys | Leu | Met | Thr | Glu | Thr | Leu | Ala | Leu | Glu | Tyr |
| | | | | 165 | | | | | 170 | | | | | 175 | |
| gcg | ccg | aag | ggc | att | cgc | gtc | aat | aat | att | ggg | cca | ggt | gcg | atc | aac | 576 |
| Ala | Pro | Lys | Gly | Ile | Arg | Val | Asn | Asn | Ile | Gly | Pro | Gly | Ala | Ile | Asn |
| | | 180 | | | | | 185 | | | | | 190 | | | |
| acg | cca | atc | aat | gct | gaa | aaa | ttc | gct | gac | cct | aaa | cag | aaa | gct | gat | 624 |
| Thr | Pro | Ile | Asn | Ala | Glu | Lys | Phe | Ala | Asp | Pro | Lys | Gln | Lys | Ala | Asp |
| | 195 | | | | | 200 | | | | | 205 | | | | |
| gta | gaa | agc | atg | att | cca | atg | gga | tat | atc | ggc | gaa | ccg | gag | gag | atc | 672 |
| Val | Glu | Ser | Met | Ile | Pro | Met | Gly | Tyr | Ile | Gly | Glu | Pro | Glu | Glu | Ile |
| 210 | | | | | 215 | | | | | 220 | | | | | |
| gcc | gca | gta | gca | gcc | tgg | ctt | gct | tcg | aag | gaa | gcc | agc | tac | gtc | aca | 720 |
| Ala | Ala | Val | Ala | Ala | Trp | Leu | Ala | Ser | Lys | Glu | Ala | Ser | Tyr | Val | Thr |
| 225 | | | | | 230 | | | | | 235 | | | | | 240 |
| ggc | atc | acg | tta | ttc | gcg | gac | ggc | ggt | atg | aca | caa | tat | cct | tca | ttc | 768 |
| Gly | Ile | Thr | Leu | Phe | Ala | Asp | Gly | Gly | Met | Thr | Gln | Tyr | Pro | Ser | Phe |
| | | | | 245 | | | | | 250 | | | | | 255 | |
| cag | gca | ggc | cgc | ggt | | | | | | | | | | | | 783 |
| Gln | Ala | Gly | Arg | Gly |
| | | | 260 |

<210> SEQ ID NO 6
<211> LENGTH: 261
<212> TYPE: PRT
<213> ORGANISM: Bacillus subtilis

<400> SEQUENCE: 6

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Ala
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

```
Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 7
<211> LENGTH: 37
<212> TYPE: DNA
<213> ORGANISM: Artificial Sequence
<220> FEATURE:
<223> OTHER INFORMATION: PCR primer

<400> SEQUENCE: 7
ggggaattca tgtatccgga tttaaaagga aaagtcg        37

<210> SEQ ID NO 8
<211> LENGTH: 32
<212> TYPE: DNA
<213> ORGANISM: Artificial Sequence
<220> FEATURE:
<223> OTHER INFORMATION: PCR primer

<400> SEQUENCE: 8
gggtctagat taaccgcggc ctgcctggaa tg        32

<210> SEQ ID NO 9
<211> LENGTH: 34
<212> TYPE: DNA
<213> ORGANISM: Artificial Sequence
<220> FEATURE:
<223> OTHER INFORMATION: PCR primer

<400> SEQUENCE: 9
cccaagctta gttaacttta gaaggagaca attc        34

<210> SEQ ID NO 10
<211> LENGTH: 18
<212> TYPE: DNA
<213> ORGANISM: Artificial Sequence
<220> FEATURE:
<223> OTHER INFORMATION: PCR primer

<400> SEQUENCE: 10
ctgccgcccg actatcac        18

ROSUVASTATIN CALCIUM AND PROCESS FOR PRODUCING INTERMEDIATE THEREOF

This application is a Divisional of U.S. patent application Ser. No. 15/116,861, U.S. Pat. No. 9,695,130 which is the National Stage of International Patent Application No. PCT/JP2015/053436, filed Feb. 6, 2015, which claims the benefit of priority of Japanese Application Nos. 2014-209480, filed Oct. 10, 2014, 2014-209142, filed Oct. 10, 2014, and 2014-021769, filed Feb. 6, 2014. The disclosures of each of application Nos. 15/116,861 and PCT/JP2015/053436 are expressly incorporated by reference herein in their entireties.

TECHNICAL FIELD

The present invention relates to a production method of rosuvastatin calcium and an intermediate therefor.

BACKGROUND ART

Rosuvastatin is an inhibitor of an enzyme, 3-hydroxy-3-methylglutaryl-coenzyme A reductase (HMG-CoA reductase), and is useful for, for example, the treatment of hypercholesterolemia and mixed dyslipidemia. Rosuvastatin is a generic name of (E)-7-[4-(4-fluorophenyl)-6-isopropyl-2-[methyl(methylsulfonyl)amino]pyrimidin-5-yl]-(3R,5S)-3,5-hydroxy-6-heptenoic acid. In treatments, rosuvastatin is administered as a calcium salt thereof. Rosuvastatin calcium is a trade name of CRESTOR (registered trade mark), and is sold as an HMG-CoA reductase inhibitor. Rosuvastatin calcium has the following chemical formula.

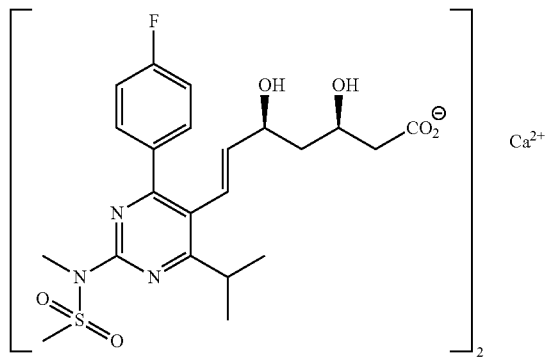

Patent document 1 discloses rosuvastatin, a sodium salt and calcium salt thereof, and production methods of these. According to patent document 1, rosuvastatin and a salt thereof are obtained by condensing methyl (3R)-3-[(tert-butyldimethylsilyl)oxy]-5-oxo-6-triphenylphosphoranylidenehexanoate and 4-(4-fluorophenyl)-6-isopropyl-2-(N-methyl-N-methanesulfonylamino)-5-pyrimidinecarboxaldehyde to introduce a side chain having one asymmetric center, and performing deprotection of 3-hydroxy group, asymmetric reduction of 5-oxo group, and hydrolysis. Since this method requires extremely low temperature conditions (preferably −85° C.--−70° C.) during asymmetric reduction, it is not entirely an industrially preferable production method.

Similar methods for introducing a side chain having two asymmetric centers are also known (patent documents 2, 3 and the like). Since these methods also require extremely low temperature conditions (e.g., about −75° C.) during Wittig reaction, they are not entirely industrially preferable production methods.

Also, methods for introducing an asymmetric center by using an optically active titanium catalyst are known (patent document 4 and the like). Since these methods use an expensive optically active catalyst, and require extremely low temperature conditions (about −80° C.--−50° C.) during asymmetric reduction, they are not entirely industrially preferable production methods.

Non-patent documents 1 and 2 describe a method for producing a dihydroxyester derivative by reduction of a diketoester derivative. However, non-patent documents 1 and 2 specifically disclose only the reduction by organic synthesis reaction, and only compounds wherein the diketoester derivative or dihydroxyester derivative is tert-butylester.

Patent documents 5 and 6 describe a production method using carbonylreductase as a production method of pitavastatin. However, patent documents 5 and 6 do not provide description relating to rosuvastatin. In addition, rosuvastatin has a pyrimidine ring substituted by a sulfonylamino group, whereas pitavastatin has a quinoline ring, and the chemical structures thereof are vastly different.

DOCUMENT LIST

Patent Documents patent document 1: JP-B-2648897
patent document 2: WO 2010/047296
patent document 3: WO 2005/042522
patent document 4: WO 2008/065410
patent document 5: WO 2002/063028
patent document 6: WO 2003/078634

Non-Patent Documents non-patent document 1: IP.com number: IPCOM000144026D, Dec. 14, 2006
non-patent document 2: IP.com number: IPCOM000145623D, Jan. 19, 2007

SUMMARY OF THE INVENTION

Problems to be Solved by the Invention

Since conventional production methods of rosuvastatin use extremely low temperature reactions and expensive asymmetric catalysts, the development of a more economical production method has been desired. The problem of the present invention is to provide a novel method capable of producing rosuvastatin calcium and intermediates therefor efficiently, inexpensively and with high purity.

Means of Solving the Problems

The present inventors have conducted intensive studies in an attempt to solve the above-mentioned problems and found that rosuvastatin calcium can be produced efficiently with a high purity under economical reaction conditions by using the following production method and/or intermediate, which resulted in the completion of the present invention.

Therefore, the present invention provides the following.
[1] A production method of a compound represented by the following formula (2):

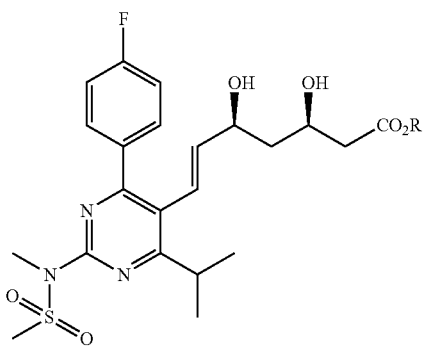

(2)

wherein R is a primary alkyl group having 1-8 carbon atoms or a secondary alkyl group having 3-6 carbon atoms, comprising
(i) a step of reducing a compound represented by the following formula (1):

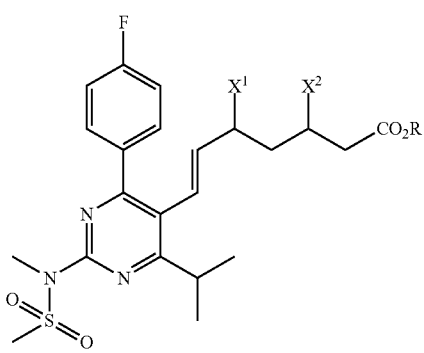

(1)

wherein R is as defined for R in the aforementioned formula (2), —X¹ and —X² are each independently —OH or =O, and —X¹ and/or —X² are/is =O, comprising reacting the compound with an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell.

[2] The production method of the above-mentioned [1], wherein the aforementioned enzyme comprises a polypeptide of any of the following (A), (B) or (C):
(A) a polypeptide having carbonylreductase (OCR1) (SEQ ID NO: 2) derived from *Ogataea minuta* var. *nonfermentans* NBRC1473,
(B) a polypeptide consisting of an amino acid sequence having a homology of 80% or more to the amino acid sequence shown in SEQ ID NO: 2, and having an activity to convert a compound represented by the aforementioned formula (1) to a compound represented by the aforementioned formula (2),
(C) a polypeptide comprising an amino acid sequence which is the amino acid sequence shown in SEQ ID NO: 2, wherein 1 or several amino acids are substituted, deleted or added, and having an activity to convert a compound represented by the aforementioned formula (1) to a compound represented by the aforementioned formula (2).

[3] The production method of the above-mentioned [1], wherein the gene encoding the aforementioned enzyme is a DNA comprising the base sequence shown in the following (D), (E) or (F):

(D) the base sequence shown in SEQ ID NO: 1,
(E) a base sequence that hybridizes to a DNA consisting of a sequence complementary to the base sequence shown in SEQ ID NO: 1 under stringent conditions, and encodes a polypeptide having an activity to act on a compound represented by the aforementioned formula (1) and convert same to a compound represented by the aforementioned formula (2),
(F) a base sequence having a base sequence which is the base sequence shown in SEQ ID NO: 1 wherein 1 or several bases are substituted, deleted or added, and encodes a polypeptide having an activity to act on a compound represented by the aforementioned formula (1) and convert same to a compound represented by the aforementioned formula (2).

[4] The production method of any of the above-mentioned [1]-[3], wherein the aforementioned step (i) is performed in the presence of polyhydric alcohol.

[5] A production method of a compound represented by the following formula (1):

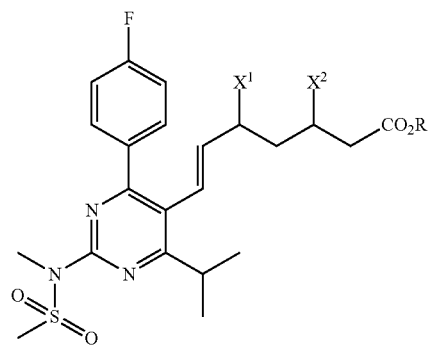

(1)

wherein R is a primary alkyl group having 1-8 carbon atoms or a secondary alkyl group having 3-6 carbon atoms, —X¹ and —X² are each independently —OH or =O, and —X¹ and/or —X² are/is =O, comprising
(ii) a step of condensing a compound represented by the following formula (3):

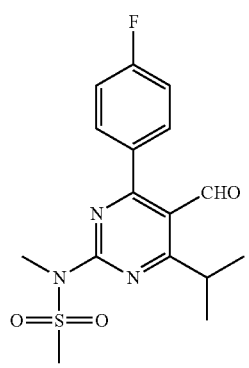

(3)

and a compound represented by the following formula (4):

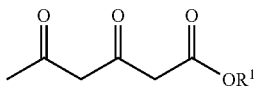

(4)

wherein R¹ is a linear or branched alkyl group having 1-8 carbon atoms, in the presence of a base.

[6] The production method of the above-mentioned [5], wherein (iia) a step of condensing a compound represented by the following formula (3):

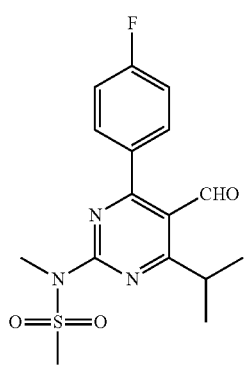

(3)

and a compound represented by the following formula (4a):

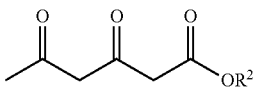

(4a)

wherein $R^2$ is a branched alkyl group having 3-8 carbon atoms, which is different from the above-mentioned R, in the presence of a base; and (iib) a step of reacting a compound represented by the following formula (5):

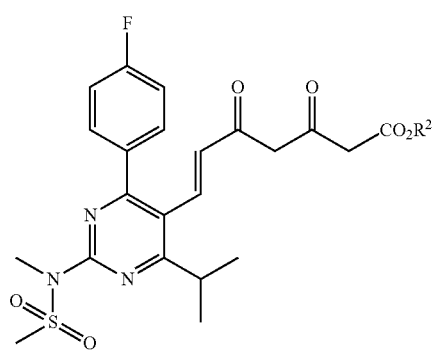

(5)

wherein $R^2$ is as defined for $R^2$ in the aforementioned formula (4a), which is obtained in the aforementioned step (iia) and an alcohol represented by R—OH wherein R is a primary alkyl group having 1-8 carbon atoms or a secondary alkyl group having 3-6 carbon atoms.

[7] The production method of the above-mentioned [5], comprising (iia) a step of condensing a compound represented by the following formula (3):

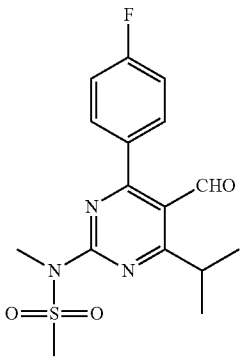

(3)

and a compound represented by the following formula (4a):

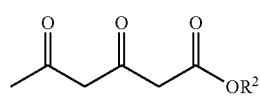

(4a)

wherein $R^2$ is a branched alkyl group having 3-8 carbon atoms, which is different from the aforementioned R, in the presence of a base;

(iib) a step of reacting a compound represented by the following formula (5):

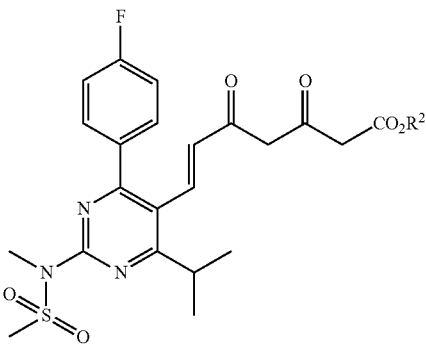

(5)

wherein $R^2$ is as defined for $R^2$ in the aforementioned formula (4a), which is obtained in the aforementioned step (iia), and an alcohol represented by R—OH wherein R is a primary alkyl group having 1-8 carbon atoms or a secondary alkyl group having 3-6 carbon atoms; and (ia) a step of obtaining compound(s) represented by the following formula (1b) and/or (1c):

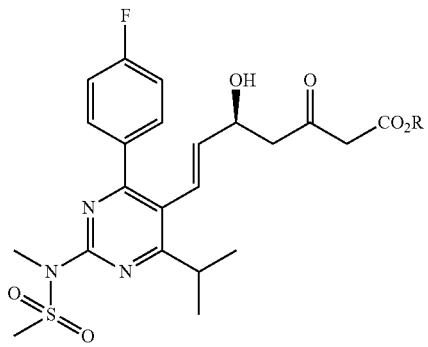

(1b)

wherein R is as defined for R in the aforementioned formula (1a),

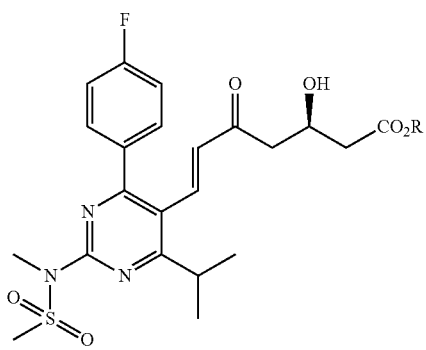

wherein R is as defined for R in the aforementioned formula (1a), comprising acting an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell on a compound represented by the following formula (1a):

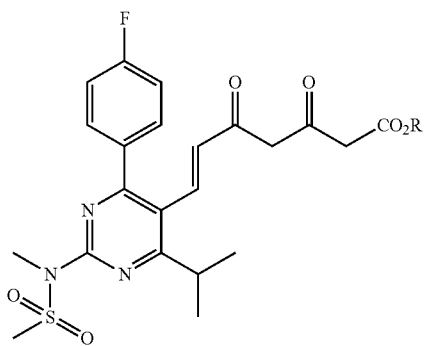

wherein R is a primary alkyl group having 1-8 carbon atoms or a secondary alkyl group having 3-6 carbon atoms, to reduce the compound.

[8] The production method of the above-mentioned [7], wherein the aforementioned enzyme comprises any of the polypeptide shown in the following (A), (B) or (C):

(A) a polypeptide having carbonylreductase (OCR1) (SEQ ID NO: 2) derived from *Ogataea minuta* var. *nonfermentans* NBRC1473, (B) a polypeptide consisting of an amino acid sequence having a homology of 80% or more to the amino acid sequence shown in SEQ ID NO: 2, and having an activity to convert a compound represented by the aforementioned formula (1) to a compound represented by the aforementioned formula (2), (C) a polypeptide comprising an amino acid sequence which is the amino acid sequence shown in SEQ ID NO: 2, wherein 1 or several amino acids are substituted, deleted or added, and having an activity to convert a compound represented by the aforementioned formula (1) to a compound represented by the aforementioned formula (2).

[9] The production method of the above-mentioned [7], wherein the gene encoding the aforementioned enzyme is a DNA comprising the base sequence shown in the following (D), (E) or (F):

(D) the base sequence shown in SEQ ID NO: 1, (E) a base sequence that hybridizes to a DNA consisting of a sequence complementary to the base sequence shown in SEQ ID NO: 1 under stringent conditions, and encodes a polypeptide having an activity to act on a compound represented by the aforementioned formula (1) and convert same to a compound represented by the aforementioned formula (2), (F) a base sequence having a base sequence which is the base sequence shown in SEQ ID NO: 1 wherein 1 or several bases are substituted, deleted or added, and encodes a polypeptide having an activity to act on a compound represented by the aforementioned formula (1) and convert same to a compound represented by the aforementioned formula (2).

[10] The production method of any of the above-mentioned [7]-[9], wherein the aforementioned step (ia) is performed in the presence of polyhydric alcohol.

[11] A compound represented by the following formula (1a):

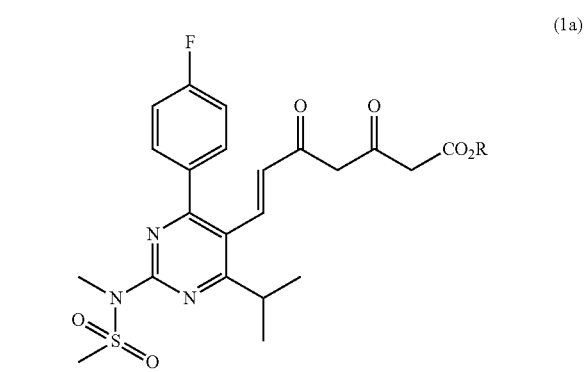

wherein R is a primary alkyl group having 1-8 carbon atoms or a secondary alkyl group having 3-6 carbon atoms.

[12] A compound represented by the following formula (1b) or (1c):

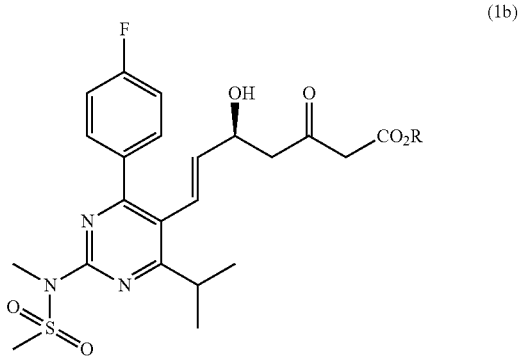

wherein R is a primary alkyl group having 1-8 carbon atoms or a secondary alkyl group having 3-6 carbon atoms,

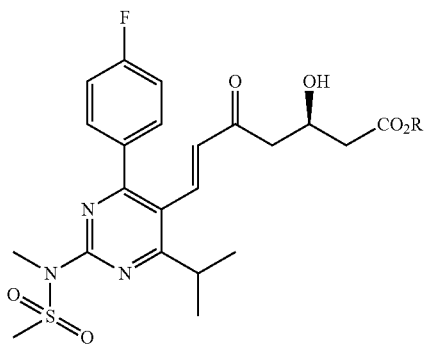

(1c)

wherein R is a primary alkyl group having 1-8 carbon atoms or a secondary alkyl group having 3-6 carbon atoms.

[13] A crystal of a compound represented by the following formula:

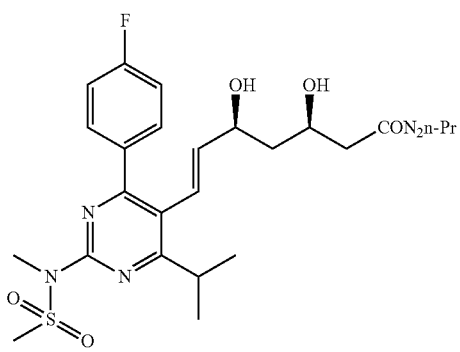

which shows a powder X-ray diffraction pattern having characteristic peaks at 2θ=8.7°, 16.3°, 19.7°, 21.2°, 21.3° (±0.2°).

[14] A production method of rosuvastatin calcium represented by the following formula (6):

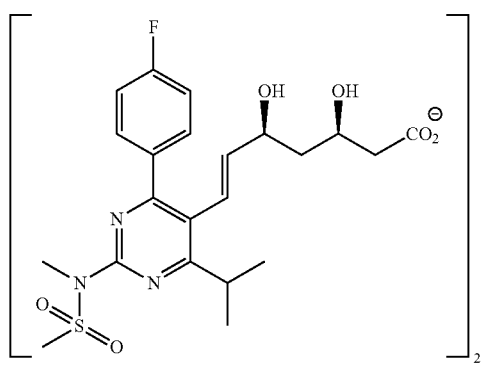

(6)

comprising (iiia) a step of hydrolyzing a compound represented by the aforementioned formula (2):

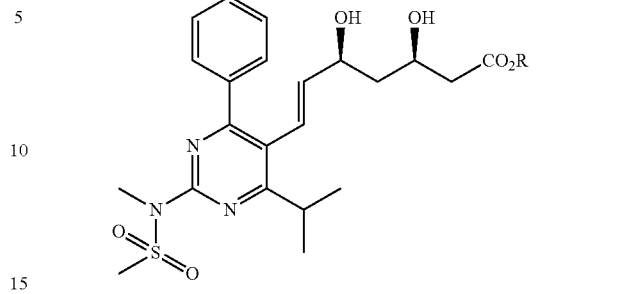

(2)

wherein R is a primary alkyl group having 1-8 carbon atoms or a secondary alkyl group having 3-6 carbon atoms, which is obtained by the production method of the above-mentioned [1], with a base, and reacting same with a calcium compound.

[15] The production method of the above-mentioned [14], wherein the aforementioned hydrolysis in the aforementioned step (iiia) is performed in the presence of mixed solvent of a polar solvent, and at least one solvent selected from the group consisting of ether solvent, hydrocarbon solvent, and halogenated solvent.

[16] The production method of the above-mentioned [14] or [15], wherein the reaction with the calcium compound in step (iiia) is initiated at pH 5-10.

[17] A production method of rosuvastatin calcium represented by the following formula (6):

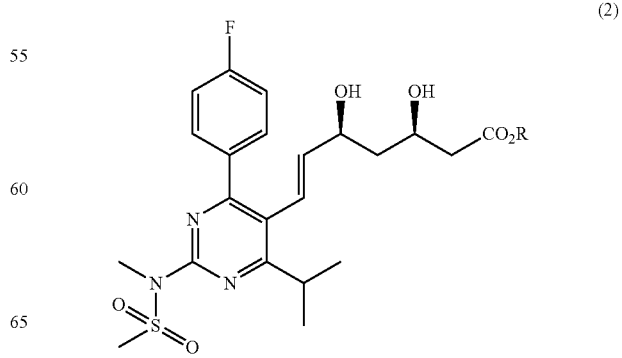

(6)

comprising (iiib) a step of hydrolyzing a compound represented by the aforementioned formula (2):

(2)

wherein R is a primary alkyl group having 1-8 carbon atoms or a secondary alkyl group having 3-6 carbon atoms, which is obtained by the production method of the above-mentioned [1], with a base, treating same with an acid, reacting the obtained compound represented by the following formula (8):

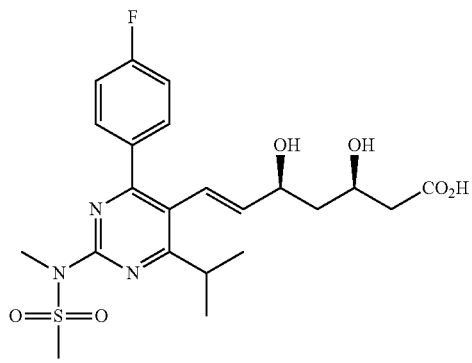
(8)

with an amine compound, subjecting the obtained compound represented by the following formula (9):

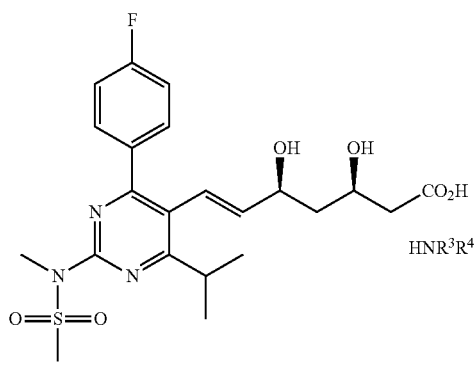
(9)

wherein $R^3$ and $R^4$ are each independently an alkyl group having 1-8 carbon atoms, to salt-exchange with a base, and reacting same with a calcium compound.

[18] A production method of rosuvastatin calcium represented by the following formula (6):

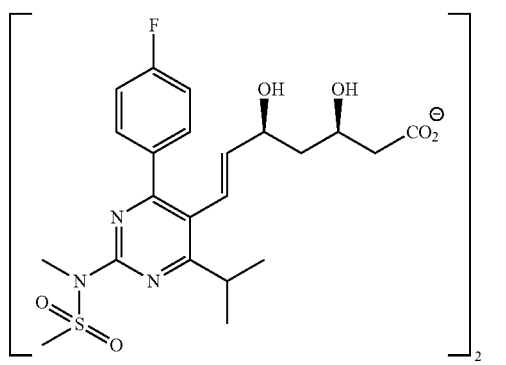
(6)

comprising (iiic) a step of hydrolyzing a compound represented by the aforementioned formula (2):

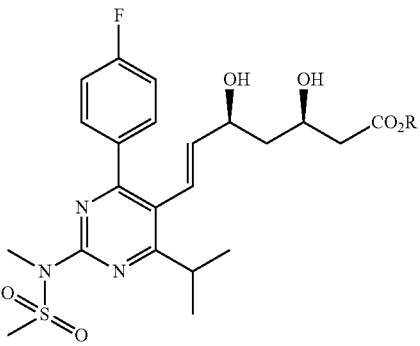
(2)

wherein R is a primary alkyl group having 1-8 carbon atoms or a secondary alkyl group having 3-6 carbon atoms, which is obtained by the production method of the above-mentioned [1], with a base, subjecting same to intramolecular dehydration condensation in the presence or absence of an acid catalyst, and reacting the obtained compound represented by the following formula (10):

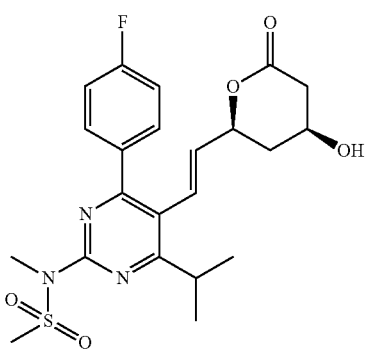
(10)

with a calcium compound.

[19] A crystal of (E)-7-[4-(4-fluorophenyl)-6-isopropyl-2-[methyl(methylsulfonyl)amino]pyrimidin-5-yl]-(3R,5S)-3,5-hydroxy-6-heptenoic acid n-propylamine salt, which shows a powder X-ray diffraction pattern having characteristic peaks at $2\theta=19.8°$, $22.9°$ ($\pm 0.2°$).

[20] A crystal of (E)-7-[4-(4-fluorophenyl)-6-isopropyl-2-[methyl(methylsulfonyl)amino]pyrimidin-5-yl]-(3R,5S)-3,5-hydroxy-6-heptenoic acid dimethylamine salt, which shows a powder X-ray diffraction pattern having characteristic peaks at $2\theta=6.6°$, $17.0°$ ($\pm 0.2°$).

[21] Rosuvastatin calcium comprising not less than 1 ppm and not more than 1500 ppm of a compound represented by the following formula (11):

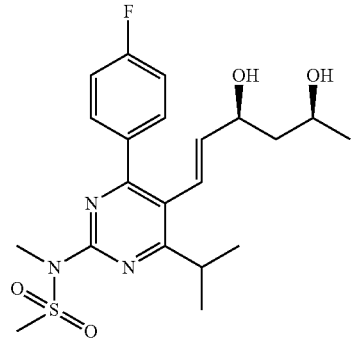
(11)

[22] A purification method of a compound represented by the following formula (2):

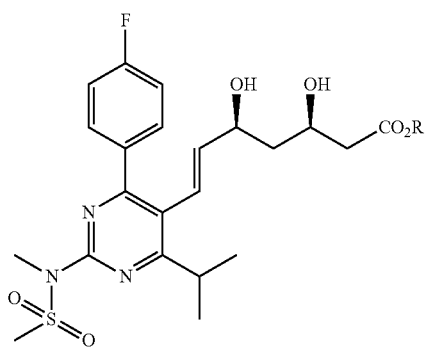

(2)

wherein R is a primary alkyl group having 1-8 carbon atoms or a secondary alkyl group having 3-6 carbon atoms, comprising dissolving the compound in an organic solvent, or a mixed solvent of an organic solvent and water, and cooling same at a cooling rate of 15° C./hr or below to precipitate a crystal of the compound represented by the aforementioned formula (2).

[23] A production method of rosuvastatin calcium, comprising (B) a step of converting a compound represented by the following formula (12):

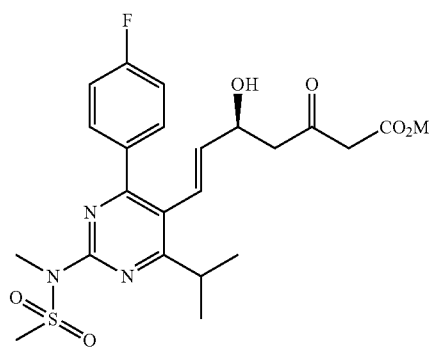

(12)

wherein M is an alkali metal element, an alkaline earth metal element or hydrogen, to a compound represented by the following formula (13):

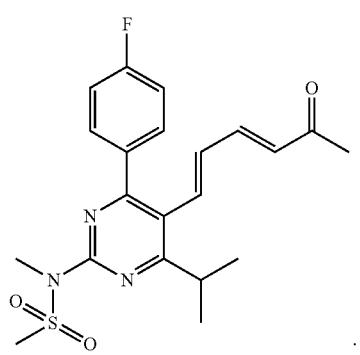

(13)

[24] The production method of the above-mentioned [23], comprising, prior to the aforementioned step (B), (Aa) a step of converting a mixture of a compound represented by the following formula (14):

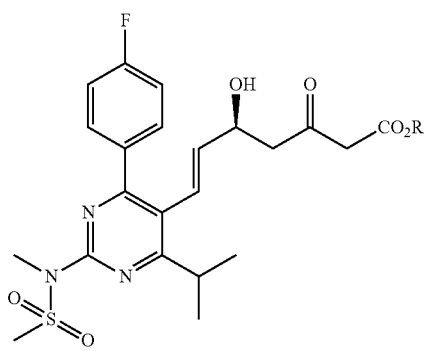

(14)

wherein R is a primary alkyl group having 1-8 carbon atoms or a secondary alkyl group having 3-6 carbon atoms, and a compound represented by the following formula (15):

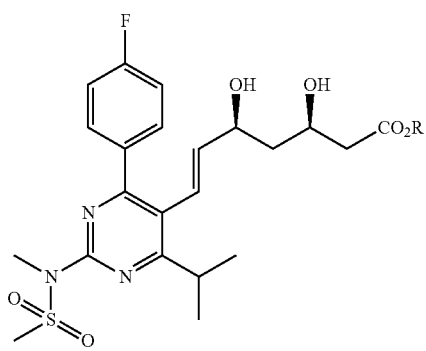

(15)

wherein R is as defined above, to a mixture of a compound represented by the following formula (16):

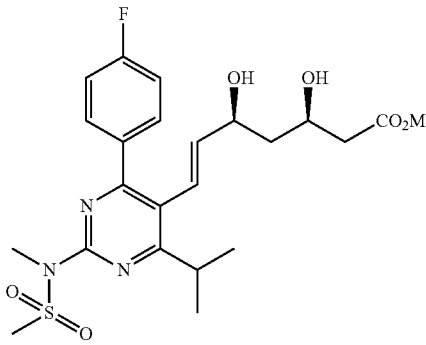

(16)

wherein M is an alkali metal element, an alkaline earth metal element or hydrogen, and a compound represented by the aforementioned formula (12), by hydrolyzing same in the presence of a base.

[25] The production method of the above-mentioned [23] or [24], comprising, after the aforementioned step (B), (C) a step of removing the compound represented by the aforementioned formula (13).

[26] The production method of the above-mentioned [25], comprising, after the aforementioned step (C), (D) a step of reacting the compound obtained by the aforementioned step (C) and a calcium compound.

[27] A purification method of rosuvastatin calcium comprising a compound represented by the following formula (12):

(12)

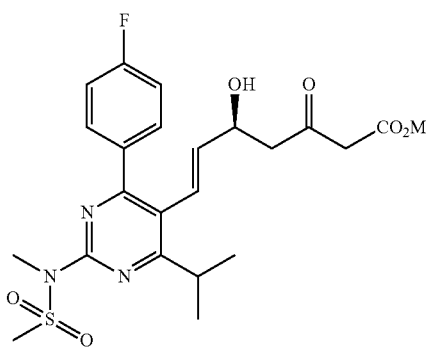

wherein M is an alkali metal element, an alkaline earth metal element or hydrogen, comprising (B) a step of converting the compound represented by the formula (12) to a compound represented by the following formula (13):

(13)

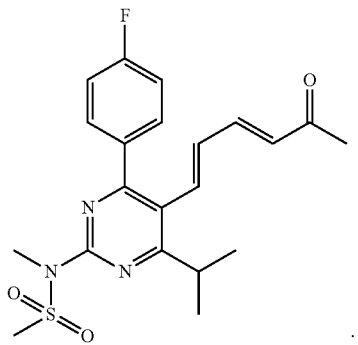

[28] The purification method of the above-mentioned [27], comprising, prior to the aforementioned step (B), (Ab) a step of dissolving rosuvastatin calcium comprising a compound represented by the aforementioned formula (12) in a solvent.
[29] The purification method of the above-mentioned [27] or [28], comprising, after the aforementioned step (B), (C) a step of removing the compound represented by the aforementioned formula (13).
[30] The purification method of the above-mentioned [29], comprising, after the aforementioned step (C), (D) a step of reacting the compound obtained by the aforementioned step (C) and a calcium compound.
[31] Rosuvastatin calcium comprising not less than 1 ppm and not more than 1000 ppm of a compound represented by the following formula (13):

(13)

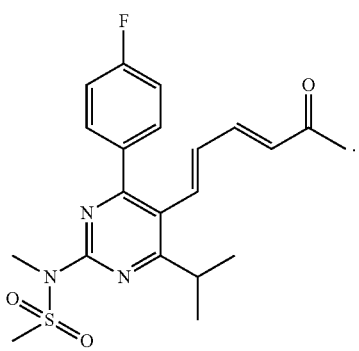

Effect of the Invention

According to the production method of the present invention, rosuvastatin calcium and intermediates therefor having a high purity can be efficiently produced under economical conditions and at an industrial scale, without using an extremely low temperature reaction or an expensive asymmetric catalyst.

DESCRIPTION OF EMBODIMENTS

Figure 1:
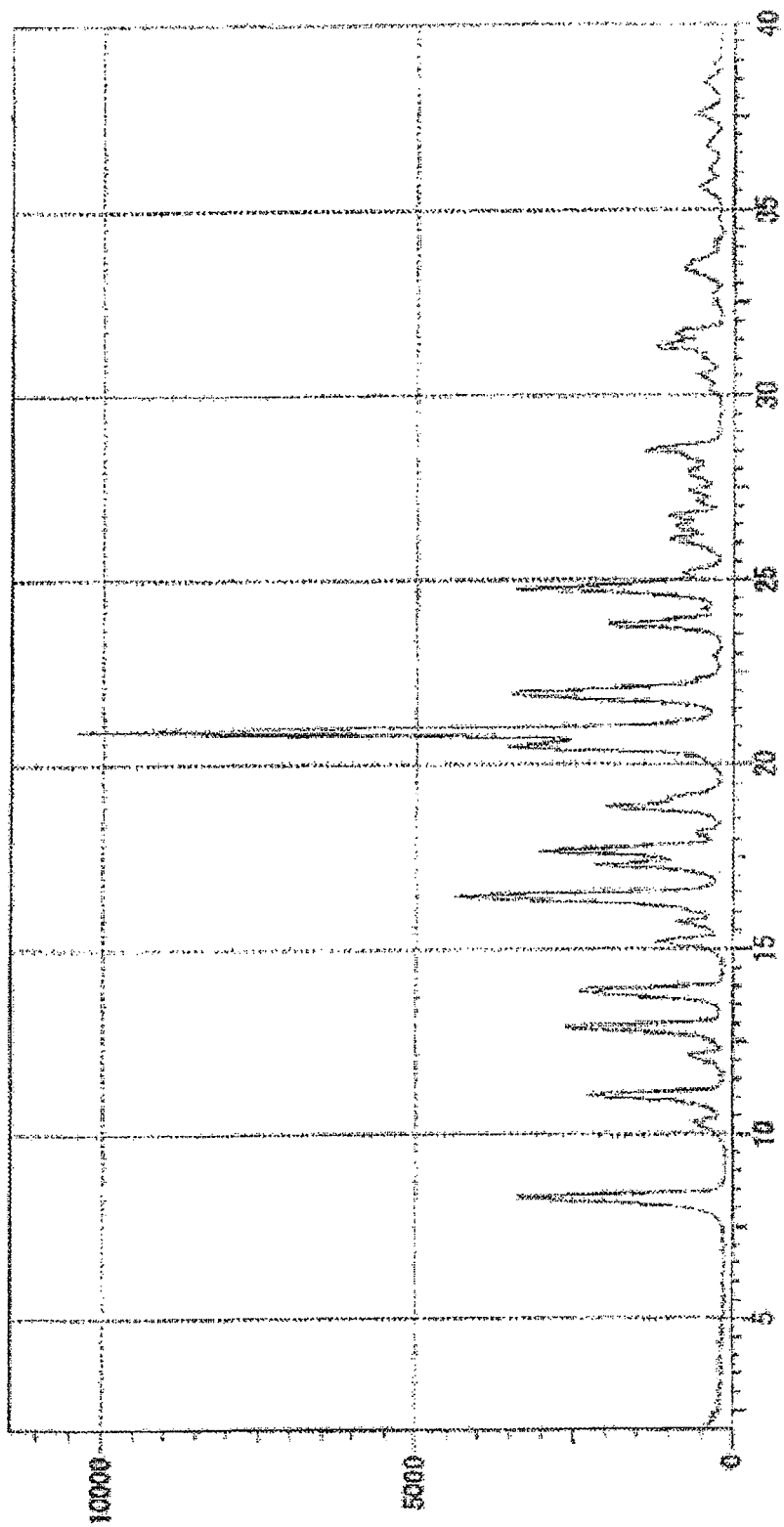
FIG. 1 shows the powder X-ray diffraction pattern of the compound (DOXP(n-propyl (E)-7-[4-(4-fluorophenyl)-6-isopropyl-2-[methyl(methylsulfonyl)amino]pyrimidin-5-yl]-3,5-dioxo-6-heptenoate)) obtained in Example 2, wherein the vertical axis shows intensity and the horizontal axis shows 2θ (°)

The terms used in the present specification are explained in detail the following.
In the present specification, the "primary alkyl group having 1-8 carbon atoms" means methyl group, ethyl group, n-propyl group, n-butyl group, n-pentyl group, n-hexyl group, n-octyl group.
In the present specification, the "primary alkyl group having 1-4 carbon atoms" means methyl group, ethyl group, n-propyl group, n-butyl group.
In the present specification, the "secondary alkyl group having 3-6 carbon atoms" means isopropyl group, cyclopropyl group, sec-butyl group, 1-methylbutyl group, 1-methylheptyl group, 1-ethylpropyl group, 1-ethylbutyl group.
In the present specification, the "secondary alkyl group having 3-4 carbon atoms" means isopropyl group, cyclopropyl group, sec-butyl group.
In the present specification, the "linear or branched alkyl group having 1-8 carbon atoms" means methyl group, ethyl group, n-propyl group, n-butyl group, n-pentyl group, n-hexyl group, n-octyl group, isopropyl group, cyclopropyl group, sec-butyl group, 1-methylbutyl group, 1-methylheptyl group, tert-butyl group, tert-amyl group.
In the present specification, the "branched alkyl group having 3-8 carbon atoms" means isopropyl group, cyclopropyl group, sec-butyl group, 1-methylbutyl group, 1-methylheptyl group, tert-butyl group, tert-amyl group.
In the present specification, the "calcium compound" means a compound such as calcium chloride, calcium acetate and the like, which can convert a carboxylic acid to a calcium salt thereof. Preferably, the calcium compound is calcium chloride.

In the present specification, the "amine compound" means a compound such as n-propylamine, isopropylamine, dimethylamine and the like, which can convert a carboxylic acid to an amine salt thereof. Preferably, the amine compound is n-propylamine or dimethylamine.

The compound of the present invention also encompasses salts, anhydrides, hydrates, solvates and the like of the compound.

In the present specification, the "enzyme having an activity capable of reducing a carbonyl group stereoselectively" means an enzyme having an activity to convert a carbonyl group in a carbonyl group-containing compound to optically active alcohol by asymmetric reduction.

Whether the "activity capable of reducing a carbonyl group stereoselectively" is present can be determined by measuring an activity to convert a carbonyl group in a carbonyl group-containing compound to an optically active alcohol by asymmetric reduction by a general assay method. For example, a measurement target enzyme is reacted with a compound represented by the formula (1), and the amount of a compound represented by the formula (2) converted from the compound represented by the formula (1) is directly measured, whereby the enzyme activity can be confirmed.

The "enzyme" in the present specification includes purified enzyme (including partially purified enzyme), an enzyme immobilized by a conventional immobilization technique, for example, one immobilized on a carrier such as polyacrylamide, carageenan gel and the like.

In the present specification, the "microorganism or cell capable of producing an enzyme having an activity capable of reducing a carbonyl group stereoselectively" (hereinafter sometimes referred to as "the microorganism or cell of the present invention") is not particularly limited as long as it has an "activity capable of reducing a carbonyl group stereoselectively", and it may be a microorganism or cell inherently having the aforementioned activity, or a microorganism or cell imparted with the aforementioned activity by bleeding. As a means for imparting the aforementioned activity by bleeding, known methods such as a gene recombinant treatment (transformation), a mutation treatment and the like can be adopted. As a method of transformation, methods such as introduction of the object gene, enhanced expression of an enzyme gene in the biosynthetic pathway of organic compounds, reduction of expression of an enzyme gene in the by-product biosynthetic pathway and the like can be used.

As the kind of the "microorganism or cell", those described in the below-mentioned host organism or host cell can be mentioned. A "microorganism or cell" in a state of being frozen can also be used. In the present specification, the "microbial or cell capable of producing an enzyme having the activity" is not limited to a living microorganism or cell, but also includes one which is biologically dead but has an enzymatic activity.

The microorganism or cell in the present invention can be produced by the method described in WO 2003/078634.

In the present specification, the kind of the organism to be a "host organism" is not particularly limited, and prokaryotes such as *Escherichia coli, Bacillus subtilis, corynebacterium, Pseudomonas bacterium, Bacillus bacterium, Rhizobium bacterium, Lactobacillus* bacterium, *Succinobacillus* bacterium, *Anaerobiospirillum* bacterium, *Actinobacillus* bacterium and the like, fungi such as yeast, filamentous fungi and the like, eucaryotes such as plant, animal and the like can be mentioned. Of these, preferred are *Escherichia coli*, yeast and *corynebacterium*, and particularly preferred is *Escherichia coli*.

In the present specification, the kind of the cell to be a "host cell" is not particularly limited, and animal cell, plant cell, insect cell and the like can be used.

In the present specification, an "expression vector" is a genetic factor used for replicating and expressing a protein having a desired function in the aforementioned host organism, by introducing a polynucleotide encoding a protein having a desired function into a host organism. Examples thereof include, but are not limited to, plasmid, virus, phage, cosmid and the like. Preferable expression vector is a plasmid.

In the present specification, a "transformant" means a microorganism or cell into which the aforementioned expression vector has been introduced, and which has acquired an ability to show a desired trait associated with a protein having a desired function.

In the present specification, a "treated product of microorganism or cell" means a product obtained by culturing a microorganism or cell, and 1) treating the microorganism or cell with an organic solvent and the like, 2) freeze-drying same, 3) immobilizing same on a carrier and the like, 4) physical or enzymatical destruction and containing a protein having a desired function and the like.

In the present specification, a "culture solution containing enzyme obtained by culturing microorganism or cell" means 1) a culture solution of microorganism or cell, 2) a culture solution obtained by treating a culture solution of microorganism or cell with an organic solvent and the like, or 3) a culture solution wherein cellular membrane of microorganism or cell is physically or enzymatically destroyed.

[The Production Method of the Present Invention]

The production method of the present invention is explained in detail below. In the following, w/v means weight/volume.

The production method of the present invention includes, as shown below, step (i) for converting a compound represented by the formula (1) to a compound represented by the formula (2), and step (iiia), (iiib) ((iiib-1)-(iiib-3)) or (iiic-1)-(iiic-2)) for converting a compound represented by the formula (2) or rosuvastatin calcium represented by the formula (6)

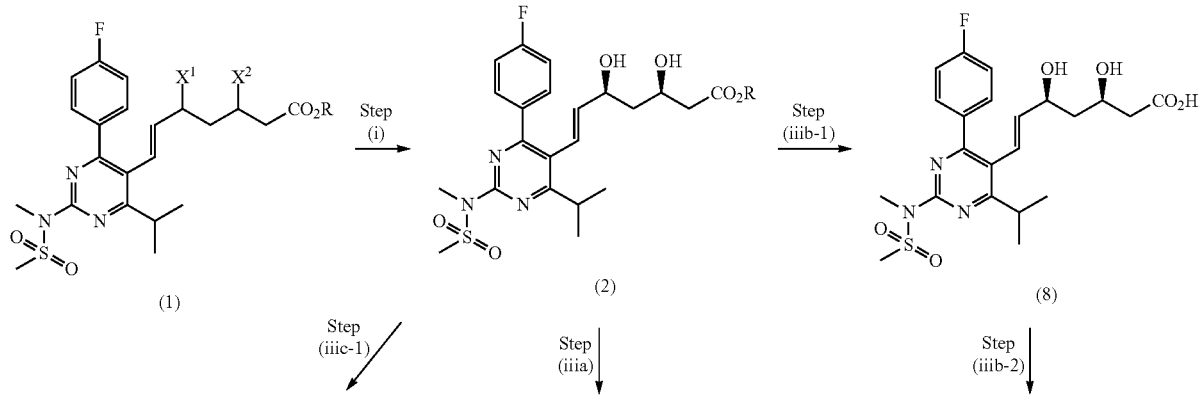

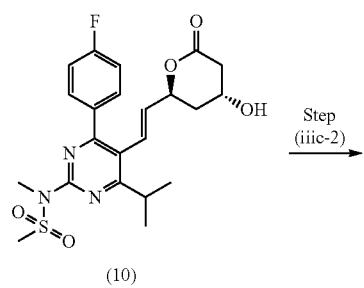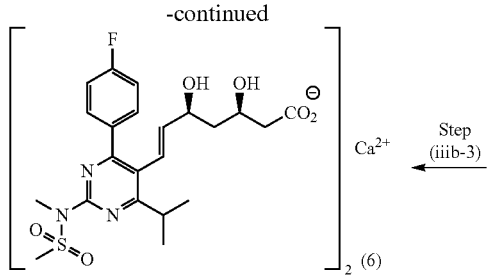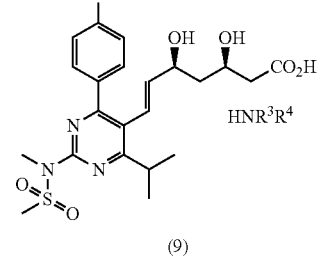

wherein, R is a primary alkyl group having 1-8 carbon atoms or a secondary alkyl group having 3-6 carbon atoms, preferably a primary alkyl group having 1-4 carbon atoms or a secondary alkyl group having 3-4 carbon atoms. As R, methyl group, ethyl group, n-propyl group, isopropyl group or n-butyl is preferable. Of these, R is more preferably n-propyl group or isopropyl group, particularly preferably n-propyl group to efficiently perform step (i).

—$X^1$ and —$X^2$ are each independently —OH or =O, and —$X^1$ and/or —$X^2$ are/is =O.

$R^3$ and $R^4$ are each independently a hydrogen atom or an alkyl group having 1-8 carbon atoms, preferably a hydrogen atom or an alkyl group having 1-4 carbon atoms.

The production method of the present invention includes, as shown below, as a production method of a compound represented by the formula (1) used in step (i), step (ii) for converting a compound represented by the formula (3) and a compound represented by the formula (4) to a compound represented by the formula (1).

Furthermore, as a preferable embodiment of step (ii), step (iia) for converting a compound represented by the formula (3) and a compound represented by the formula (4a) to a compound represented by the formula (5), and step (iib) for converting a compound represented by the formula (5) to a compound represented by the formula (1) are included.

As another embodiment of step (i), moreover, step (ia) for converting a compound represented by the formula (1a) to a compound represented by the formula (1b) and/or a compound represented by the formula (1c), and step (ib) for converting a compound represented by the formula (1b) and/or a compound represented by the formula (1c) to a compound represented by the formula (2) are also included in the production method of the present invention.

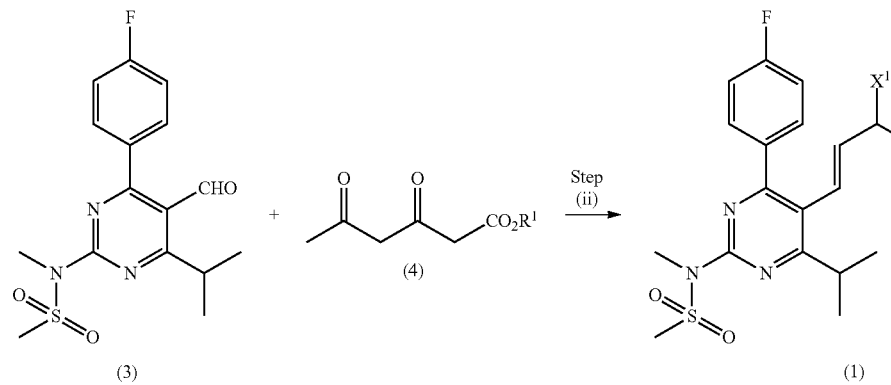

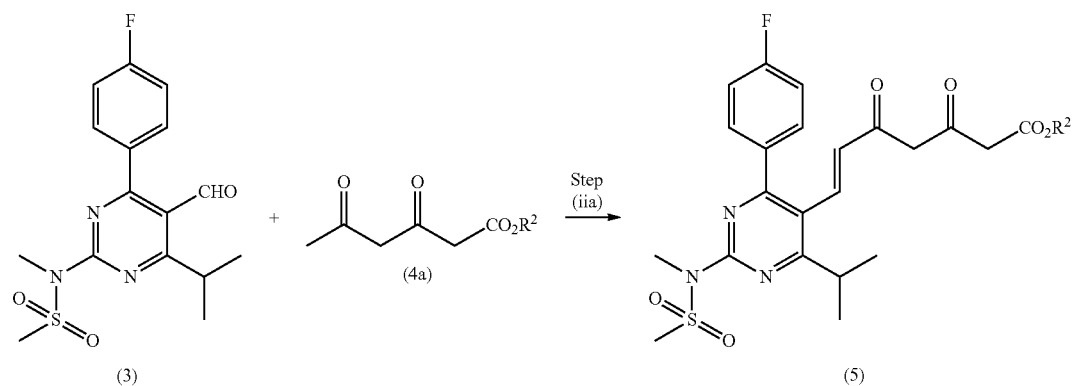

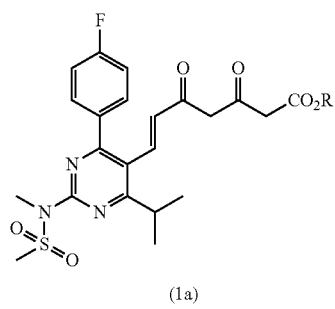
(1a)

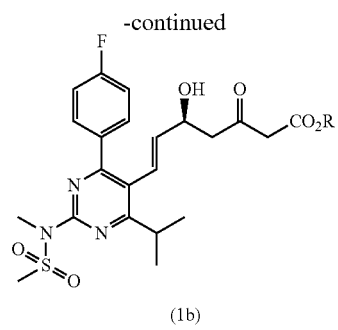
(1b)

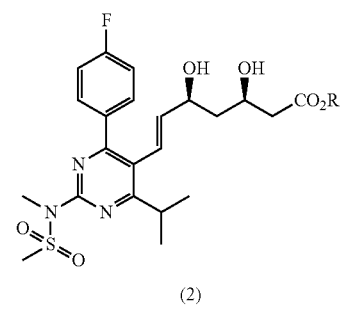
(2)

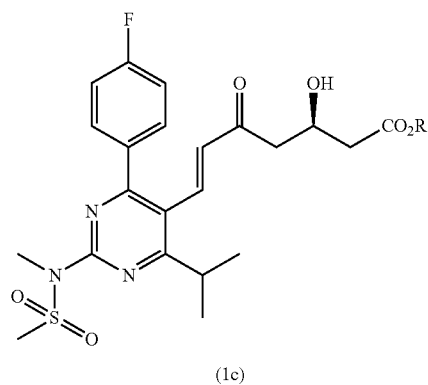
(1c)

wherein R, —$X^1$ and —$X^2$ are as defined above.

$R^1$ is a linear or branched alkyl group having 1-8 carbon atoms, preferably a primary alkyl group having 1-8 carbon atoms or a secondary alkyl group having 3-6 carbon atoms, more preferably a primary alkyl group having 1-4 carbon atoms or a secondary alkyl group having 3 or 4 carbon atoms. As $R^1$, methyl group, ethyl group, n-propyl group, isopropyl group or n-butyl is preferable. Of these, $R^1$ is more preferably n-propyl group or isopropyl group, particularly preferably n-propyl group, since step (i) can be performed efficiently.

$R^2$ is a branched alkyl group having 3-8 carbon atoms, and is different from the above-mentioned R. $R^2$ is preferably isopropyl group, s-butyl group, tert-butyl group, tert-amyl group, particularly preferably tert-butyl group.

In the following, each step of the production method of the present invention is explained in detail.

Step (i):

In step (i), a compound represented by the formula (1) is reduced by reaction with an enzyme having an activity capable of stereoselectively reducing a carbonyl group, a microorganism or cell having an ability to produce the enzyme (the microorganism or cell of the present invention), a treated product of the microorganism or cell, and/or a culture solution containing the enzyme obtained by culturing the microorganism or cell (hereinafter these are sometimes collectively referred to as "the enzyme etc. of the present invention") to give a compound represented by the formula (2).

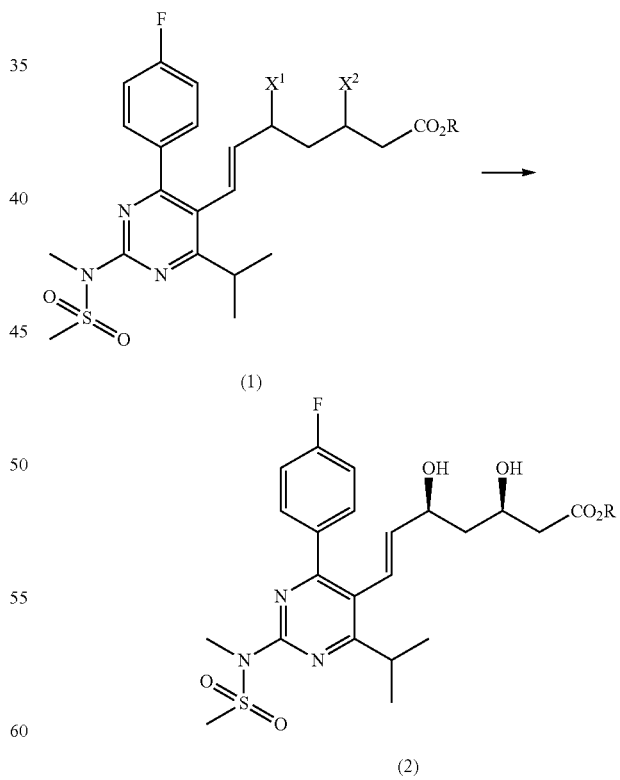

wherein, R, —$X^1$ and —$X^2$ are as defined above.

As the enzyme used in step (i), one having the amino acid sequence shown in SEQ ID NO: 2 (hereinafter sometimes to be referred to as "OCR1") or a homologue of the amino acid sequence can be used. Specifically, an enzyme containing a polypeptide of the following (A), (B) or (C) or a homologue of these can be mentioned.

(A) a polypeptide having carbonylreductase (OCR1) (SEQ ID NO: 2) derived from *Ogataea minuta* var. *nonfermentans* NBRC1473 described in JP-B-4270918,
(B) a polypeptide consisting of an amino acid sequence having a so homology of 80% or more to the amino acid sequence shown in SEQ ID NO: 2, and having an activity to convert a compound represented by the formula (1) to a compound represented by the formula (2),
(C) a polypeptide comprising an amino acid sequence which is the amino acid sequence shown in SEQ ID NO: 2, wherein 1 or several amino acids are substituted, deleted or added, and having an activity to convert a compound represented by the formula (1) to a compound represented by the formula (2).

A homologue of the above-mentioned (B) is a protein having at least 80%, preferably 85% or more, more preferably 90% or more, further preferably 95% or more, homology with the full-length amino acid sequence shown in SEQ ID NO: 2.

A homologue of the above-mentioned (C) has an amino acid sequence which is the amino acid sequence shown in SEQ ID NO: 2, wherein 1 or several amino acids are deleted, added or substituted, as long as the activity capable of stereoselectively reducing the carbonyl group is not inhibited. As used herein, "1 or several amino acids" is specifically 20 or less, preferably 10 or less, more preferably 5 or less, amino acids.

The gene encoding the above-mentioned enzyme is a DNA comprising the base sequence shown in the following (D), (E) or (F) or a homologue thereof:
(D) the base sequence shown in SEQ ID NO: 1,
(E) a base sequence that hybridizes to a DNA consisting of a sequence complementary to the base sequence shown in SEQ ID NO: 1 under stringent conditions, and encodes a polypeptide having an activity to act on a compound represented by the formula (1) and convert same to a compound represented by the formula (2),
(F) a base sequence having a base sequence which is the base sequence shown in SEQ ID NO: 1 wherein 1 or several bases are substituted, deleted or added, and encodes a polypeptide having an activity to act on a compound represented by the formula (1) and convert same to a compound represented by the formula (2).

Here, the "base sequence that hybridizes under stringent conditions" in the above-mentioned (E) means a base sequence of a DNA obtained by colony hybridization method, plaque hybridization method, or Southern blot hybridization method and the like under stringent conditions by using DNA as a probe. Examples of the stringent conditions in colony hybridization method and plaque hybridization method include conditions of hybridization using a filter immobilizing a colony- or plaque-derived DNA or a fragment of the DNA in the presence of a 0.7 mol/L-1.0 mol/L aqueous sodium chloride solution at 65° C., and washing the filter with 0.1-2×SSC solution (composition of 1×SSC, 150 mmol/L aqueous sodium chloride solution, 15 mmol/L aqueous sodium citrate solution) at 65° C.

Each hybridization can be performed according to the method described in Molecular Cloning: A Laboratory Manual, 2nd Ed., Cold Spring Harbor Laboratory, Cold Spring Harbor, N.Y., 1989 and the like.

A homologue of the above-mentioned (F) has a base sequence which is the base sequence shown in SEQ ID NO: 1, wherein 1 or several bases are deleted, added or substituted, as long as the activity capable of stereoselectively reducing the carbonyl group is not inhibited. As used herein, "1 or several bases" is specifically 60 or less, preferably 30 or less, more preferably 15 or less, bases.

In step (i), since the enzyme etc. of the present invention is superior in the handling property, and easily added to a reaction system, it can also be used in a frozen state. When frozen enzyme etc. of the present invention are used, the shape thereof is not particularly limited and, for example, prismatic, cylindrical, bulk, spherical shape and the like can be employed.

In step (i), a compound represented by the formula (1) to be a reaction substrate is generally used at a substrate concentration of 0.01% w/v-20% w/v, preferably 0.1% w/v-10% w/v. A reaction substrate may be added at once at the start of the reaction. When substrate is inhibited by the enzyme, the enzyme can also be added continuously or intermittently to reduce the influence thereof or improve accumulation concentration of the resultant product.

Step (i) is preferably performed in the presence of coenzyme $NAD(P)^+$ or $NAD(P)H$. In this case, the above-mentioned coenzyme is preferably added at a concentration of generally 0.001 mmol/L-100 mmol/L, preferably 0.01 mmol/L-10 mmol/L.

When the above-mentioned coenzyme is added, regeneration of $NAD(P)^+$ produced from $NAD(P)H$ into NAD(P)H in the reaction system is preferable, since production efficiency can be improved. Examples of the regeneration method include
1) a method utilizing an ability to generate $NAD(P)H$ from $NAD(P)^+$ of the microorganism or cell itself in the present invention, i.e., $NAD(P)^+$ reduction ability,
2) a method comprising addition of one or more kinds from a microorganism or a treated product thereof having an ability to generate $NAD(P)H$ from $NAD(P)^+$, or an enzyme utilizable for regeneration of $NAD(P)H$ such as glucose dehydrogenase, formate dehydrogenase, alcohol dehydrogenase, amino acid dehydrogenase, organic acid dehydrogenase (malic acid dehydrogenase and the like) and the like (hereinafter to be referred to as "regenerating enzyme") to a reaction system,
3) a method comprising concurrent introduction of one or more kinds of the above-mentioned regenerating enzyme gene into a host organism or host cell when producing the microorganism or cell in the present invention, and the like.

In the above-mentioned method of 1), glucose, ethanol, 2-propanol or formic acid and the like are preferably added to the reaction system.

In the above-mentioned method of 2), a microorganism having an ability to produce the above-mentioned regenerating enzyme, a treated product of microorganism such as the microorganism treated with acetone or freeze-dry treated, physically or enzymatically disrupted and the like, the enzyme fraction obtained as a crude product or purified product, and further, these after immobilization on a carrier such as polyacrylamide gel, carageenan gel and the like, and the like may be used, or a commercially available enzyme may also be used.

In this case, the amount of the above-mentioned regenerating enzyme to be used is such amount that renders the enzyme activity generally 0.01-fold to 100-fold, preferably about 0.5-fold to 20-fold, as compared to the carbonyl reduction activity of the enzyme of the present invention having an ability to stereoselectively reduce a carbonyl group.

While addition of a compound to be the substrate of the above-mentioned regenerating enzyme, for example, glucose when glucose dehydrogenase is utilized, formic acid when formate dehydrogenase is utilized, ethanol or isopropanol when alcohol dehydrogenase is utilized and the like, is also necessary, the amount thereof to be added is generally 0.1 equivalent-20 equivalents, preferably 1 equivalent-10 equivalents, relative to a compound represented by the formula (1) to be the reaction starting material.

In the method of the above-mentioned 3), a method for incorporating a DNA of the above-mentioned regenerating enzyme into chromosome along with a DNA encoding the enzyme used in step (i), a method for introducing both DNAs into a single expression vector and transforming a host organism or cell, or a method for introducing both DNAs into separate expression vectors, and transforming a host organism or cell can be used. In the method for introducing both DNAs into separate expression vectors, and transforming a host organism or cell, an expression vector needs to be selected in consideration of the incompatibility between both expression vectors.

When plural genes are introduced into a single expression vector, a method of connecting regions involved in the control of expression such as a promoter and a terminator and the like to each gene, as well as expression as an operon containing multiple cistrons such as lactose operon are also possible.

Step (i) is performed in an aqueous medium or a mixture of the aqueous medium and an organic solvent, which contains a compound represented by the formula (1) and the above-mentioned enzyme, a microorganism or cell having an ability to produce the enzyme, a treated product of the microorganism or cell, and/or a culture solution containing the enzyme obtained by culturing the microorganism or cell and, where necessary, various coenzymes (a regenerating system thereof, i.e., more preferably the coenzyme can be regenerated). A compound represented by the formula (1) can be produced by the below-mentioned method.

As the aqueous medium, water and buffers such as potassium phosphate buffer, sodium citrate buffer, Tris-HCl buffer and the like can be mentioned.

As the organic solvent, a solvent in which a compound represented by the formula (1) shows high solubility, such as ethyl acetate, isopropyl acetate, butyl acetate, toluene, chloroform, n-hexane, n-heptane, dimethyl sulfoxide, methanol, ethanol, n-propanol, 2-propanol and the like can be used. Of these, dimethyl sulfoxide, methanol, ethanol are preferable as an organic solvent, since a compound represented by the formula (1) shows high solubility. Furthermore, dimethyl sulfoxide is more preferable since conversion ratio is high.

Step (i) can also be performed in the presence of polyhydric alcohol such as glycerol, ethylene glycol, propylene glycol, erythritol, inositol, sorbitol, xylitol and the like. The aforementioned polyhydric alcohol may be a polymer or derivative, and one kind thereof may be used or a mixture of two or more kinds thereof can also be used. When step (i) is performed in the presence of polyhydric alcohol, the conversion ratio tends to be improved. Among those, glycerol is preferable since it is assumed to maintain enzymatic activity by retaining conformation of the enzyme, and is easily available. The amount of glycerol to be used is preferably not less than 40 g/L, more preferably not less than 170 g/L, and preferably not more than 600 g/L, more preferably not more than 400 g/L.

The below-mentioned step (ia) and/or step (ib) can also be performed in the presence of the aforementioned polyhydric alcohol.

Step (i) is generally performed at a reaction temperature of 4° C.-70° C., preferably 20° C.-60° C., generally at pH 3-11, preferably pH 4-8. The reaction time is generally 0.5 hr-48 hr, preferably 0.5 hr-24 hr. It can also be performed utilizing a membrane reactor and the like.

A compound represented by the formula (2) obtained in step (i) can be purified by separating cells, polypeptide and the like by centrifugation, filtration and the like, adjusting to a suitable pH, extraction with an organic solvent such as hexane, ethyl acetate, toluene and the like, and applying an appropriate combination of purification by column chromatography, crystallization and the like.

When a compound represented by the formula (2) is purified by crystallization, as an organic solvent that can be used, a solvent in which a compound represented by the formula (2) shows high solubility, for example, hydrocarbon solvents such as cyclohexane, n-hexane, n-heptane, toluene and the like, halogenated solvents such as chlorobenzene, dichlorobenzene and the like, ether solvents such as tert-butyl methyl ether, tetrahydrofuran (THF), cyclopentyl methyl ether (CPME) and the like, alcoholic solvents such as methanol, ethanol, n-propanol, isopropanol and the like, polar solvents such as N-methyl-2-pyrrolidone, N,N-dimethylformamide, N,N-dimethylacetamide, dimethyl sulfoxide and the like, and the like can be used. These organic solvents can be used singly, and a mixed solvent of these organic solvents and water can also be used.

When a compound represented by the formula (2) is purified by crystallization, a crystal of a compound represented by the aforementioned formula (2) is preferably precipitated by dissolving a compound represented by the aforementioned formula (2) in an organic solvent, or a mixed solvent of an organic solvent and water, and then cooling same at a cooling rate of 15° C./hr or below (this step of crystal precipitation by cooling is hereinafter to be referred to as a "cooling step").

In the cooling step, a temperature at which cooling is started is preferably 15° C.-60° C., more preferably 20° C.-55° C.

The cooling rate in the cooling step is preferably not more than 15° C./hr, more preferably not more than 9° C./hr, further preferably not more than 6° C./hr, particularly preferably not more than 5° C./hr. In this way, the purity of the obtained compound represented by the formula (2) can be increased.

The cooling rate can be changed during the cooling step. Particularly, slow cooling is preferable within a temperature range of preferably not more than 45° C., more preferably not more than 40° C. To be specific, the cooling rate is more preferably 9° C./hr, further preferably not more than 6° C./hr, particularly preferably not more than 5° C./hr.

Also, it is preferable to include a step of aging (hereinafter to be referred to as "aging step") after dissolving a compound represented by the aforementioned formula (2) in the aforementioned solvent and before the aforementioned cooling step. The aging step preferably has an aging step at a high temperature and a low temperature aging step wherein aging is performed at a temperature lower than that in the high temperature aging step. In the aging step, the order of the high temperature aging step and the low temperature aging step is not particularly limited, and a high temperature aging step is preferably performed after a low temperature aging step. In addition, a low temperature aging step and a high temperature aging step may be repeated several times as necessary.

The low temperature aging step in the aging step is a step wherein aging is performed after dissolving a compound represented by the aforementioned formula (2) in the aforementioned organic solvent or a mixed solvent of an organic solvent and water, and at a temperature lower than the temperature of dissolution in the aforementioned organic solvent and the like, and lower than the aging temperature of the below-mentioned high temperature aging step.

The aging temperature in the low temperature aging step is preferably lower than the temperature of dissolution in the aforementioned organic solvent and the like by not less than 1° C., more preferably not less than 5° C., particularly preferable not less than 10° C. A specific aging temperature is preferably 0° C.-59° C., more preferably 5° C.-50° C.

In the low temperature aging step, the temperature can be changed on the way. When the temperature is changed, for example, aging can be performed first at a comparatively high temperature (e.g., 35° C.-45° C.) for 5 min-12 hr, after which at a comparatively low temperature (e.g., 30° C.-40° C.) for 10 min-5 hr.

The low temperature aging step is preferably performed for 10 min-24 hr, more preferably 20 min-10 hr.

In the low temperature aging step, the temperature is not merely retained but, where necessary, the solution may be stirred or a seed crystal may be added.

The high temperature aging step in the aging step is a step wherein aging is performed at a temperature higher than the aging temperature of the aforementioned low temperature aging step.

The aging temperature in the high temperature aging step is preferably higher than the aging temperature in the aforementioned low temperature aging step by not less than 1° C., more preferably not less than 3° C., particularly preferably not less than 5° C. A specific aging temperature is preferably 20° C.-60° C., more preferably 25° C.-55° C. Generally, the aforementioned cooling step is started from the aging temperature of the high temperature aging step (final temperature of the high temperature aging step when the high temperature aging step is performed plural times). The temperature can be changed on the way also in the high temperature aging step.

The high temperature aging step is preferably performed for 10 min-24 hr, more preferably 20 min-10 hr.

In the high temperature aging step, the temperature is not merely retained but, where necessary, the solution may be stirred.

By forming such aging step, effects of improved filtration efficiency and improved purity of the object product can be obtained.

When a compound represented by the formula (2) is purified by crystallization, purification is preferably achieved by performing the aforementioned aging step (the aforementioned high temperature aging step, and the aforementioned low temperature aging step) and the aforementioned cooling step after dissolving a compound represented by the aforementioned formula (2) in an organic solvent, or a mixed solvent of an organic solvent and water.

The purity of the obtained crystal can be further improved by crystallization by such method.

Step (i) can also be performed in two steps of step (ia) and step (ib) as shown below.

Step (ia):

In step (ia), a compound represented by the formula (1a) which is the formula (1) wherein —$X^1$ and —$X^2$ are =O, is reduced by reaction with an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell to give a compound represented by the formula (1b) which is the formula (1) wherein —$X^1$ is —OH and —$X^2$ is =O, and/or a compound represented by the formula (1c) which is the formula (1) wherein —$X^1$ is =O and —$X^2$ is —OH.

A compound represented by the formula (1a) can be reduced by a method similar to that in step (i).

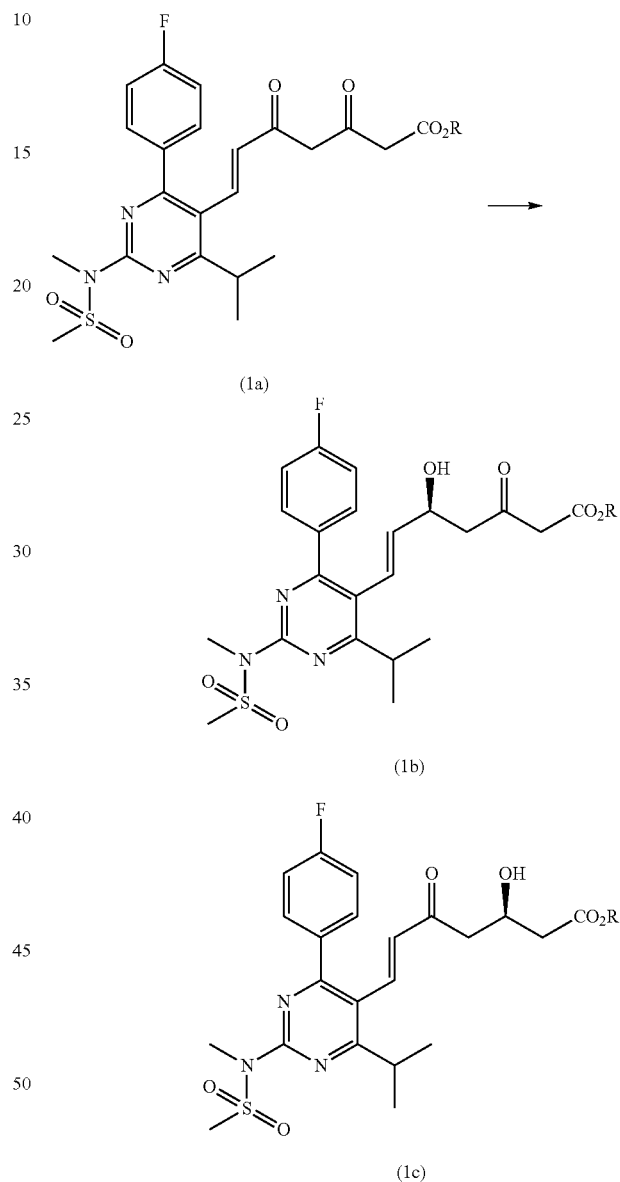

wherein R is as defined above.

The compound(s) represented by the formula (1b) and/or (1c) obtained in step (ia) may be purified by, for example, crystallization before subjecting to step (ib).

Step (ib):

In step (ib), a compound represented by the formula (1b) and/or a compound represented by the formula (1c) obtained in step (ia) is reduced by applying the above-mentioned enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell to give a compound represented by the formula (2).

A compound represented by the formula (1b) and/or a compound represented by the formula (1c) can be reduced by a method similar to that in step (i).

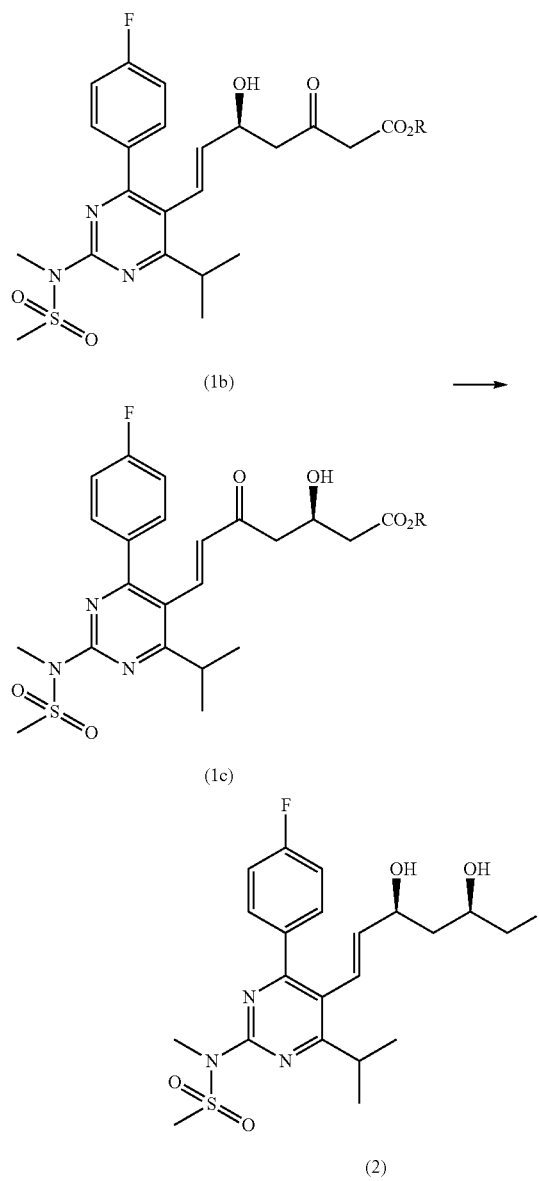

(1b)

(1c)

(2)

wherein R is as defined above.

Among the compounds represented by the formula (2) obtained in step (i), or step (ia) and (ib), since a compound of the formula (2) wherein R is an n-propyl group or isopropyl group has high crystallinity, it can be obtained with a high purity.

A crystal of a compound of the formula (2) wherein R is an n-propyl group has, for example, a powder X-ray diffraction pattern shown below (powder X-ray diffraction patterns shown below were obtained in the below-mentioned Example 5).

TABLE 1

| 2θ | relative intensity |
|---|---|
| 7.7 | 16 |
| 8.4 | 65 |
| 11.2 | 8 |
| 12.6 | 32 |
| 12.9 | 9 |
| 14.6 | 11 |
| 15.0 | 12 |
| 16.1 | 26 |
| 16.8 | 36 |
| 18.1 | 7 |
| 18.4 | 11 |
| 19.5 | 35 |
| 21.1 | 100 |
| 22.1 | 8 |
| 22.5 | 13 |
| 24.2 | 6 |
| 24.4 | 9 |
| 24.7 | 10 |
| 25.1 | 5 |
| 26.4 | 6 |
| 28.5 | 8 |
| 29.5 | 6 |
| — | — |

That is, a crystal of a compound of the formula (2) wherein R is an n-propyl group has a powder X-ray diffraction pattern showing characteristic peaks at 2θ=8.4°, 16.1°, 21.1° (±0.2°). Furthermore, a powder X-ray diffraction pattern showing peaks at 2θ=7.70, 8.4°, 16.1°, 19.5°, 21.1° (±0.2°) is preferable, and a powder X-ray diffraction pattern showing peaks at 2θ=7.7°, 8.4°, 15.0°, 16.1°, 19.5°, 21.1°, 22.5°, (±0.2°) is more preferable. In addition, a powder X-ray diffraction pattern showing peaks at 2θ=16.3°, 19.7°, 21.3° (±0.2°) is also preferable, and further, a powder X-ray diffraction pattern showing characteristic peaks at 2θ=7.9°, 16.3°, 19.7°, 21.3°, 22.7°, 24.9° (±0.2°) is more preferable.

Step (ii):

Step (ii) is a step for preparing a compound represented by the formula (1) to be used in step (i). Specifically, a compound represented by the formula (3) and a compound represented by the formula (4) are condensed in the presence of a base.

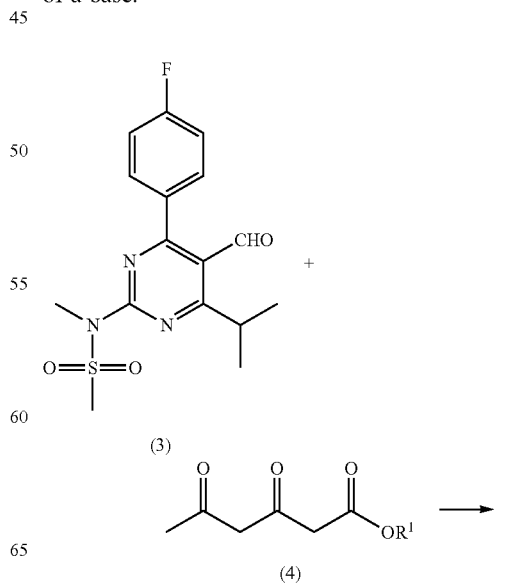

(3)

(4)

-continued (1)

wherein, $R^1$, R, $—X^1$ and $—X^2$ are as defined above.

As the base, metal hydrides such as sodium hydride, potassium hydride, calcium hydride and the like, metal amides such as sodium amide and the like, organic lithiums such as butyllithium, lithium diisopropylamide and the like, Grignard reagents such as tert-butylmagnesium chloride and the like, alkoxides such as sodium ethoxide, sodium tert-butoxide, potassium tert-butoxide and the like, and the like can be used, particularly, sodium hydride, sodium amide and sodium tert-butoxide are preferable. The amount of the base to be used is generally 1 equivalent-6 equivalents, preferably 1.5 equivalents-6 equivalents, relative to a compound represented by the formula (3).

The reaction can be performed using a solvent. While the solvent is not particularly limited as long as the reaction proceeds, hydrocarbon solvents such as cyclohexane, n-hexane, n-heptane, toluene and the like, halogenated solvents such as chlorobenzene, dichlorobenzene and the like, ether solvents such as tert-butyl methyl ether, tetrahydrofuran (THF), cyclopentyl methyl ether (CPME) and the like, polar solvents such as N-methyl-2-pyrrolidone, N,N-dimethylformamide, N,N-dimethylacetamide, dimethyl sulfoxide and the like, and the like can be used. One kind thereof may be used or a mixture of two or more kinds thereof can also be used, and a mixture of a polar solvent and a nonpolar solvent can also be used.

The amount of the solvent to be used is, generally 5 mL-100 mL, preferably 5 mL-30 mL, relative to 1 g of a compound represented by the formula (3).

The reaction temperature is generally −10° C.-200° C., preferably −5° C.-40° C.

The reaction time is generally 0.1 hr-200 hr, preferably 1 hr-24 hr.

A compound represented by the formula (3) can be produced by the method described in, for example, JP-B-2648897, and a commercially available can also be used.

A compound represented by the formula (4) can be produced according to a known method, for example, the method described in SYNTHETIC COMMUNICATIONS, 18(7), 735-739 (1988), and the method described in Reference Example 1 in the present specification, and a commercially available compound can also be used.

A compound represented by the formula (4) has a pH of preferably not more than 4, more preferably not more than 3. The pH of a compound represented by the formula (4) is a value obtained by mixing a compound represented by the formula (4) and water at 1:1 (volume ratio), and measuring the pH of the aqueous layer. When the pH value is too high (e.g., pH higher than 4), it can be lowered as necessary with an acid such as acetic acid, hydrochloric acid, sulfuric acid and the like. As a result, the preservation stability of a compound represented by the formula (4) is improved, and impurity formation during the reaction can be reduced.

When $R^1$ in the formula (4a) is a group different from R in the formula (1), a compound represented by the formula (1) is obtained by reacting a compound obtained by the above-mentioned condensation and alcohol represented by R—OH. In this step, a method similar to that in the below-mentioned step (iib) can be employed.

Step (ii) particularly preferably includes the following steps (iia) and (iib).

Step (iia):

In step (iia), a compound represented by the formula (5) is obtained by condensing a compound represented by the formula (3) and a compound represented by the formula (4a) which is the formula (4) wherein $R^1$ is $R^2$, in the presence of a base.

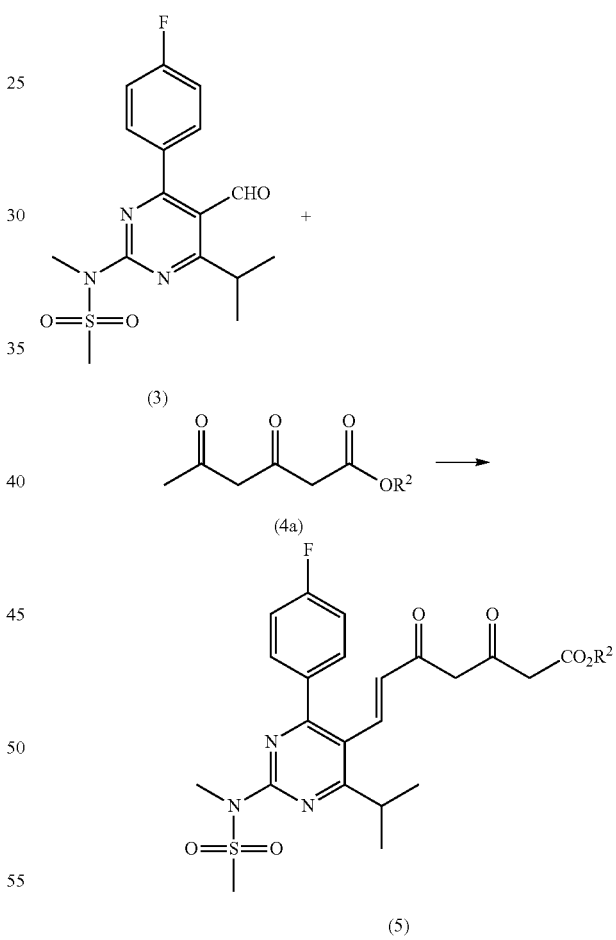

wherein $R^2$ is as defined above.

As the base, metal hydrides such as sodium hydride, potassium hydride, calcium hydride and the like, metal amides such as sodium amide and the like, organic lithiums such as butyllithium, lithium diisopropylamide and the like, Grignard reagents such as tert-butylmagnesium chloride and the like, alkoxides such as sodium ethoxide, sodium tert-butoxide, potassium tert-butoxide and the like, and the like can be used, particularly, sodium amide, sodium tert-butoxide and sodium hydride are preferable. The amount of the base to be used is generally 1 equivalent-6 equivalents, preferably 1.5 equivalents-6 equivalents, relative to a compound represented by the formula (3).

The reaction can be performed using a solvent. While the solvent is not particularly limited as long as the reaction proceeds, hydrocarbon solvents such as cyclohexane, n-hexane, n-heptane, toluene and the like, halogenated solvents such as chlorobenzene, dichlorobenzene and the like, ether solvents such as tert-butyl methyl ether, THF, CPME and the like, polar solvents such as N-methyl-2-pyrrolidone, N,N-dimethylformamide, N,N-dimethylacetamide, dimethyl sulfoxide and the like, and the like can be used. One kind thereof may be used or a mixture of two or more kinds thereof can also be used, and a mixture of a polar solvent and a nonpolar solvent can also be used.

The amount of the solvent to be used is, generally 5 mL-100 mL, preferably 5 mL-30 mL, relative to 1 g of a compound represented by the formula (3).

The reaction temperature is generally 0° C.-200° C., preferably 0° C.-40° C.

The reaction time is generally 0.1 hr-200 hr, preferably 1 hr-24 hr.

Since a compound represented by the formula (5) has high crystallinity, it can be obtained with a high purity without performing a complicated purification such as chromatography and the like.

Step (iib):

A compound represented by the formula (5) is reacted with alcohol represented by R—OH to give a compound represented by the formula (1a).

Here, R is a primary alkyl group having 1-8 carbon atoms or a secondary alkyl group having 3-6 carbon atoms, preferably a primary alkyl group having 1-4 carbon atoms or a secondary alkyl group having 3-4 carbon atoms. As R, methyl group, ethyl group, n-propyl group, isopropyl group or n-butyl group is preferable, n-propyl group or isopropyl group is more preferable, and n-propyl group is particularly preferable.

The amount of alcohol represented by R—OH to be used is generally 1 mL-100 mL, preferably 1 mL-10 mL, relative to 1 g of a compound represented by the formula (5).

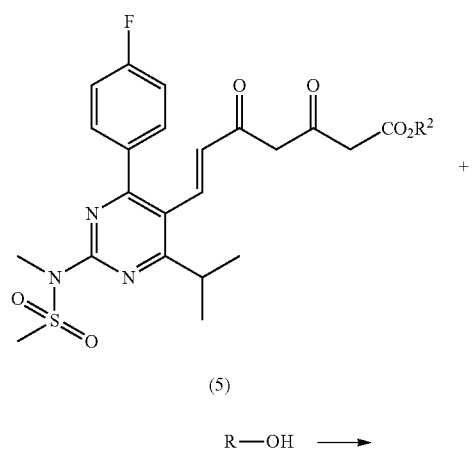

(5)

R—OH →

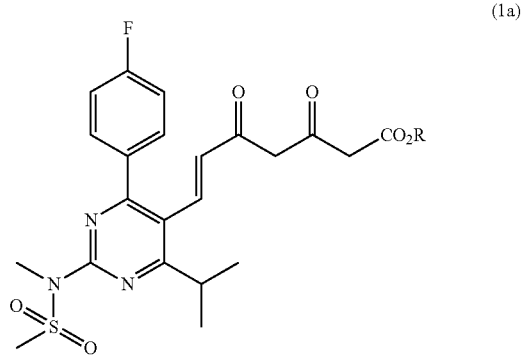

(1)

wherein $R^2$, R, —$X^1$ and —$X^2$ are as defined above.

Of compounds represented by the formula (1), a compound represented by the following formula (1a) is particularly preferable.

(1a)

wherein R is as defined above.

The reaction can also be performed in a solvent. While the solvent is not particularly limited as long as the reaction proceeds, ester solvents such as ethyl acetate, methyl acetate, isopropyl acetate and the like, nonpolar solvents such as cyclohexane, n-hexane, n-heptane, toluene and the like, halogenated solvents such as methylene chloride, chloroform, carbon tetrachloride and the like, ether solvents such as tert-butyl methyl ether (MTBE), THF, CPME and the like, polar solvents such as N-methyl-2-pyrrolidone, N,N-dimethylformamide, N,N-dimethylacetamide, dimethyl sulfoxide and the like, and the like can be used. One kind thereof may be used or a mixture of two or more kinds thereof can also be used, and a mixture of a polar solvent and a nonpolar solvent can also be used. In addition, alcohol itself represented by R—OH may also be used as a solvent.

The amount of the solvent to be used is generally 1 mL-100 mL, preferably 1 mL-10 mL, relative to 1 g of a compound represented by the formula (5).

The reaction temperature is generally 30° C.-150° C., preferably 40° C.-110° C.

The reaction time is generally 1 hr-48 hr, preferably 2 hr-24 hr.

A compound represented by the formula (1) obtained as mentioned above, particularly a compound represented by the formula (1a), among them, a compound of the formula (1a) wherein R is an n-propyl group or isopropyl group has high crystallinity, it can be obtained with a high purity.

A crystal of a compound of the formula (1a) wherein R is an n-propyl group preferably has, for example, a powder X-ray diffraction pattern shown below (powder X-ray diffraction patterns shown below were obtained in the below-mentioned Example 2).

TABLE 2

| 2θ | relative intensity |
|---|---|
| 8.3 | 32.3 |
| 11.1 | 21.5 |
| 12.1 | 6.4 |
| 13.0 | 25.3 |
| 13.9 | 23.1 |
| 15.2 | 11.7 |
| 16.5 | 41.5 |
| 17.4 | 20.5 |
| 17.7 | 29.1 |
| 18.9 | 19.2 |
| 19.2 | 9.9 |
| 20.6 | 33.7 |
| 21.0 | 100 |
| 22.0 | 33.1 |
| 23.9 | 18.7 |
| 24.9 | 32.5 |
| 26.2 | 9.7 |
| 26.6 | 8.4 |
| 27.5 | 7 |
| 28.1 | 7 |
| 28.6 | 13.5 |
| 30.3 | 4 |
| 31.5 | 11.5 |
| 31.8 | 8.9 |
| 33.5 | 7.7 |
| 37.8 | 6 |
| — | — |
| — | — |

That is, it has a powder X-ray diffraction pattern showing characteristic peaks at 2θ=8.3°, 16.5°, 21.0° (±0.2°). Furthermore, a powder X-ray diffraction pattern showing characteristic peaks at 2θ=8.3°, 16.5°, 21.0°, 22.0° (±0.2°) is preferable, and a powder X-ray diffraction pattern showing characteristic peaks at 2θ=8.3°, 13.0°, 13.9°, 16.5°, 17.7°, 21.0°, 22.0°, 24.9° (±10.2°) is more preferable. In addition, a powder X-ray diffraction pattern showing peaks at 2θ=16.7°, 17.6°, 20.8°, 22.1° (±0.2°) is also preferable.

Moreover, a crystal of a compound of the formula (1a) wherein R is an n-propyl group also preferably has a powder X-ray diffraction pattern shown below (powder X-ray diffraction patterns shown below were obtained in the below-mentioned Example 2').

TABLE 3

| 2θ | relative intensity |
|---|---|
| 5.2 | 6 |
| 6.5 | 6 |
| 7.9 | 7 |
| 9.8 | 15 |
| 10.3 | 100 |
| 11.8 | 57 |
| 14.1 | 35 |
| 15.5 | 5 |
| 16.5 | 30 |
| 17.5 | 8 |
| 17.9 | 5 |
| 18.4 | 46 |
| 19.0 | 19 |
| 19.5 | 21 |
| 20.6 | 17 |
| 21.5 | 63 |

TABLE 3-continued

| 2θ | relative intensity |
|---|---|
| 21.9 | 10 |
| 23.7 | 19 |
| 24.1 | 5 |
| 25.3 | 10 |
| 26.1 | 12 |
| 27.1 | 5 |
| 29.7 | 6 |
| 30.7 | 5 |
| 31.0 | 5 |
| 31.5 | 5 |
| 35.7 | 8 |
| 38.2 | 5 |

That is, it has a powder X-ray diffraction pattern showing characteristic peaks at 2θ=10.3°, 11.8°, 21.5° (±0.2°). Furthermore, a powder X-ray diffraction pattern showing characteristic peaks at 2θ=10.3°, 11.8°, 14.1°, 18.4°, 21.5° (±0.20) is preferable, and a powder X-ray diffraction pattern showing characteristic peaks at 2θ=10.3°, 11.8°, 14.1°, 16.5°, 18.4°, 19.0°, 19.5°, 20.6°, 21.5°, 23.7° (±0.2°) is more preferable. In addition, a powder X-ray diffraction pattern showing peaks at 2θ=16.7°, 19.2°, 20.8°, 21.3° (±0.2°) is also preferable.

Step (iiia):

In step (iiia), a compound represented by the formula (2) is hydrolyzed with a base, reacted with a calcium compound, and the obtained resultant product is isolated, whereby rosuvastatin calcium shown by the formula (6) is obtained.

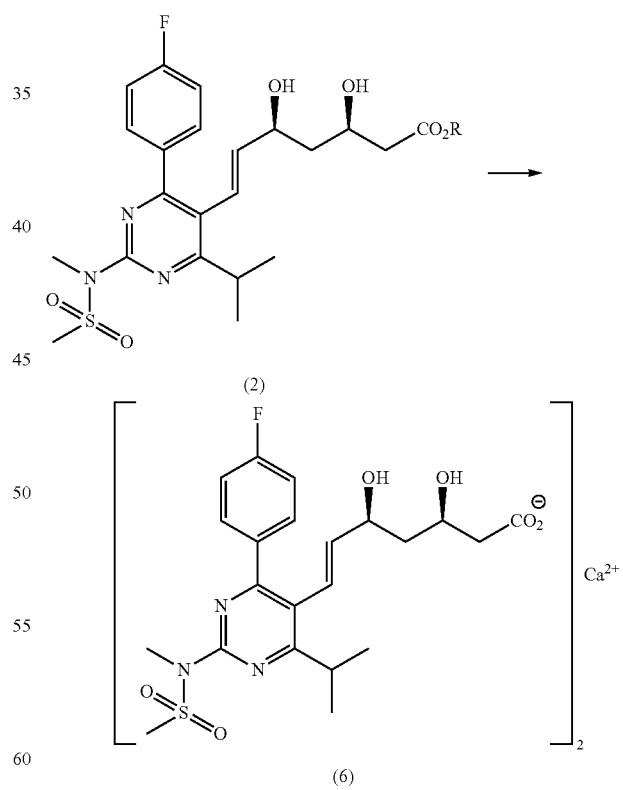

wherein R is as defined above.

In step (iiia), a compound represented by the formula (2) is first hydrolyzed with a base.

As the base, sodium hydroxide, potassium hydroxide and the like can be used, and particularly, sodium hydroxide is preferable. The amount of the base to be used is generally 0.9 equivalents-2 equivalents, preferably 1 equivalent-1.5 equivalents, relative to a compound represented by the formula (2).

The reaction can be performed in a solvent. While the solvent is not particularly limited as long as the reaction proceeds, hydrocarbon solvents such as cyclohexane, n-hexane, n-heptane, toluene and the like, halogenated solvents such as methylene chloride, chloroform, carbon tetrachloride and the like, ether solvents such as MTBE, THF, CPME and the like, polar solvents such as N-methyl-2-pyrrolidone, N,N-dimethylformamide, N,N-dimethylacetamide, dimethyl sulfoxide, water and the like can be used. Furthermore, a mixed solvent of such polar solvent and at least one kind selected from the group consisting of ether solvent, hydrocarbon solvent, and halogenated solvent is preferable, and a mixed solvent of a polar solvent and an ether solvent is preferable. Using such mixed solvent, a resultant product obtained by hydrolysis (e.g., sodium salt) is transferred to an aqueous layer, and impurity is transferred to an organic solvent layer, whereby the resultant product and impurity can be preferably separated easily.

When a mixed solvent of a polar solvent and at least one kind selected from the group consisting of ether solvent, hydrocarbon solvent, and halogenated solvent is used as a solvent, of those mentioned above, water or a mixed solvent of water and other polar solvent (e.g., THF, N-methyl-2-pyrrolidone, dimethyl sulfoxide etc.) is preferable as a polar solvent. MTBE and CPME are preferable as ether solvent, cyclohexane and toluene are preferable as hydrocarbon solvent, and methylene chloride is preferable as halogenated solvent. Of these, since toxicity of the solvent is low, a mixed solvent of water and MTBE or a mixed solvent of water and CPME is particularly preferably used.

The amount of the solvent to be used is generally 1 mL-100 mL, preferably 2 mL-50 mL, more preferably 5 mL-30 mL, relative to 1 g of a compound represented by the formula (2).

The reaction temperature is generally $-10°$ C.$-50°$ C., preferably $0°$ C.$-40°$ C.

The reaction time is generally 1 hr-48 hr, preferably 2 hr-24 hr.

The pH during reaction is preferably pH 8 or more, more preferably pH 9 or more. In this range, the reaction efficiency can be improved. The upper limit thereof is preferably not more than pH 13.

After hydrolysis of a compound represented by the formula (2), it can be subjected to a reaction with the below-mentioned calcium compound. Where necessary, washing, extraction, concentration, drying and the like may be performed and, for example, it can be isolated as a sodium salt. Then, the resultant product obtained by the aforementioned hydrolysis is reacted with a calcium compound to give rosuvastatin calcium represented by the formula (6).

As the calcium compound, calcium chloride, calcium acetate and the like can be used, and calcium acetate is particularly preferable due to its high solubility in water.

The amount of the calcium compound to be used is generally 0.4 equivalents-3 equivalents, preferably 0.5 equivalents-2 equivalents, more preferably 0.5 equivalents-1.5 equivalents, relative to a compound represented by the formula (2).

In the reaction with a calcium compound, while the solvent is not particularly limited as long as the reaction proceeds, ester solvents such as ethyl acetate, methyl acetate, isopropyl acetate and the like, ether solvents such as MTBE, THF, CPME and the like, polar solvents such as N-methyl-2-pyrrolidone, N,N-dimethylformamide, N,N-dimethylacetamide, dimethyl sulfoxide, acetonitrile, water and the like can be used. Of these, water or a mixed solvent of water and a polar solvent other than water is preferable, and water is more preferable. Examples of the polar solvent other than water include THF, N-methyl-2-pyrrolidone, dimethyl sulfoxide and the like.

The amount of the solvent to be used is generally 1 mL-100 mL, preferably 2 mL-50 mL, more preferably 5 mL-30 mL, relative to 1 g of a compound represented by the formula (2).

The reaction temperature is generally $-10°$ C.$-50°$ C., preferably $0°$ C.$-40°$ C., more preferably $5°$ C.$-25°$ C.

The reaction time is generally 0.01 hr-48 hr, preferably 0.5 hr-24 hr.

The pH during reaction is generally pH 5-pH 13, preferably pH 6-pH 12. The pH at the time of start of the reaction is preferable pH 5-pH 10, more preferably pH 6-pH 9. By adjusting pH to fall within such range, washing of the compound obtained after the reaction is facilitated, and the amount of the impurity contained in the obtained compound can be reduced.

Rosuvastatin calcium obtained in step (iiia) can be subjected to aging, cooling, drying, pulverization, crushing and the like as necessary.

Step (iiib):

In step (iiib), a compound represented by the formula (2) is hydrolyzed with a base, treated with an acid, the obtained compound represented by the formula (8) is reacted with an amine compound, the obtained compound represented by the formula (9) is hydrolyzed with a base, and reacted with a calcium compound, whereby rosuvastatin calcium shown by the formula (6) is obtained.

To be specific, a compound represented by the formula (2) is hydrolyzed with a base to give a compound represented by the formula (7).

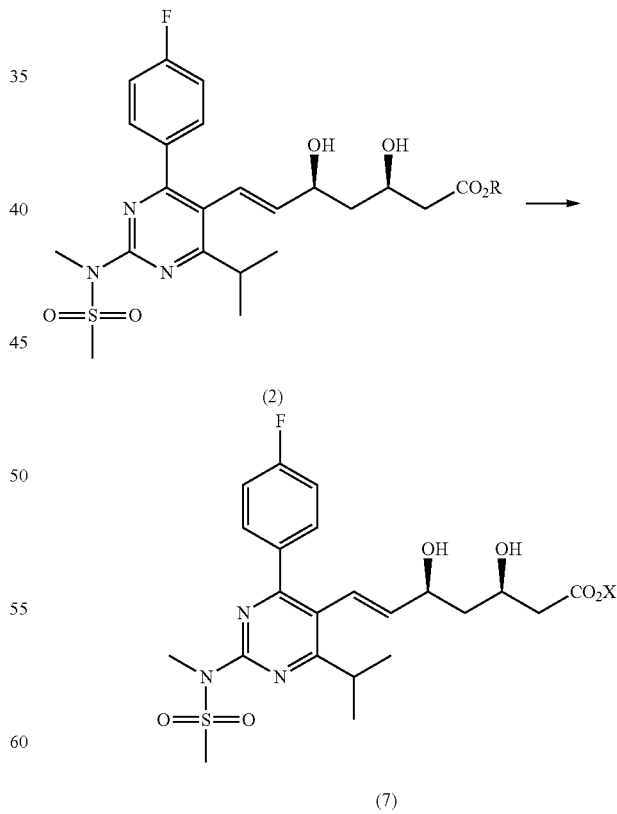

wherein R is as defined above, and X is sodium or potassium and the like.

As the base, sodium hydroxide, potassium hydroxide and the like can be used, and particularly, sodium hydroxide is preferable. The amount of the base to be used is generally 0.9 equivalents-2 equivalents, preferably 1 equivalent-1.5 equivalents, relative to a compound represented by the formula (2).

As the calcium compound, calcium chloride, calcium acetate and the like can be used, and calcium chloride is particularly preferable. The amount of the calcium compound to be used is generally 0.4 equivalents-1.5 equivalents, preferably 0.5 equivalents-1.2 equivalents, relative to a compound represented by the formula (2).

The reaction can be performed in a solvent. While the solvent is not particularly limited as long as the reaction proceeds, ester solvents such as ethyl acetate, methyl acetate and the like, nonpolar solvents such as cyclohexane, n-hexane, n-heptane and the like, halogenated solvents such as methylene chloride, chloroform, carbon tetrachloride and the like, ether solvents such as MTBE, THF, CPME and the like, polar solvents such as N-methyl-2-pyrrolidone, N,N-dimethylformamide, N,N-dimethylacetamide, dimethyl sulfoxide, water and the like, and a mixture of such polar solvent and a nonpolar solvent is preferable. The amount of the solvent to be used is generally 1 mL-100 mL, preferably 5 mL-30 mL, relative to 1 g of a compound represented by the formula (2).

The reaction temperature is generally −10° C.-50° C., preferably 0° C.-40° C.

The reaction time is generally 1 hr-48 hr, preferably 2 hr-24 hr.

Then, a compound represented by the formula (7) is treated with an acid to give a compound represented by the formula (8).

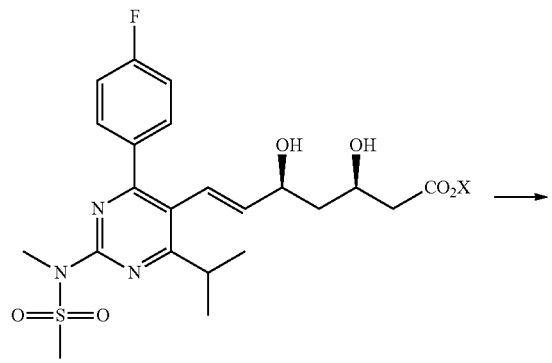

(7)

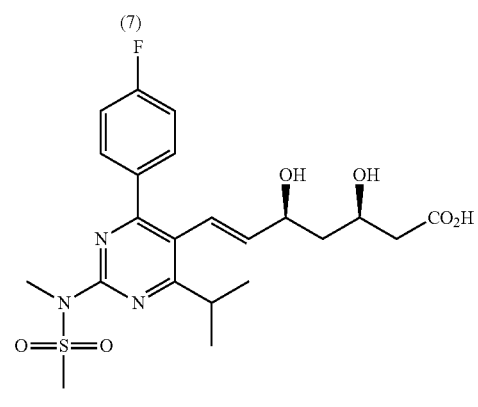

(8)

wherein X is as defined above.

As an acid, hydrochloric acid, sulfuric acid and the like can be used, and hydrochloric acid is particularly preferable. The amount of the acid to be used is not particularly limited as long as acidification is possible. It is generally 1 equivalent-3 equivalents, preferably 1 equivalent-1.5 equivalents, relative to the base used for hydrolysis.

The reaction temperature is generally −10° C.-50° C., preferably 0° C.-30° C.

The reaction time is generally 0.5 hr-5 hr.

Furthermore, an amine compound is added to a compound represented by the formula (8) to give an amine salt represented by the formula (9). An amine salt having high crystallinity can improve the purity of the object rosuvastatin calcium.

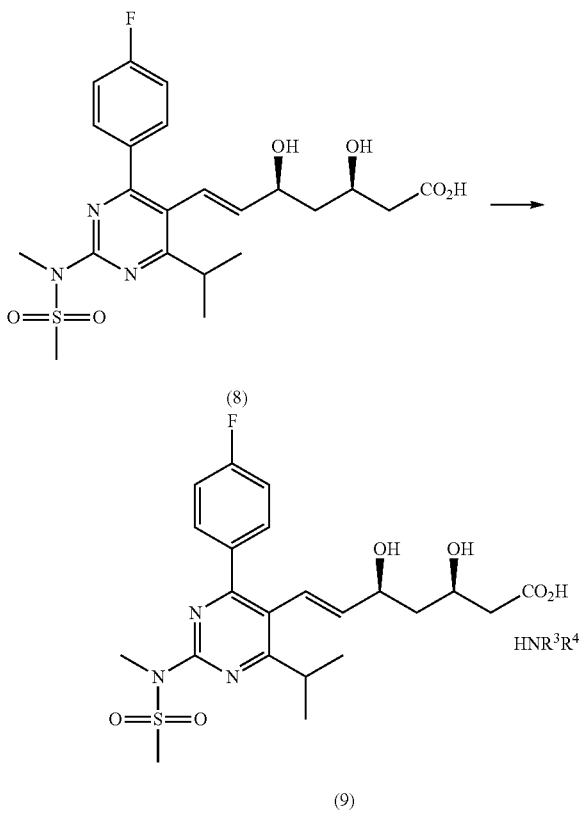

wherein $R^3$ and $R^4$ are as defined above.

As an amine compound, n-propylamine, isopropylamine, dimethylamine and the like can be used, and n-propylamine and dimethylamine are particularly preferable. The amount of the amine compound to be used is generally 1 equivalent-3 equivalents, preferably 1 equivalent-2 equivalents, relative to a compound represented by the formula (8).

The reaction can also be performed in a solvent. While the solvent is not particularly limited as long as the reaction proceeds, ester solvents such as ethyl acetate, methyl acetate, isopropyl acetate and the like, halogenated solvents such as methylene chloride, chloroform, carbon tetrachloride and the like, ether solvents such as MTBE, THF, CPME and the like, polar solvents such as N-methyl-2-pyrrolidone, N,N-dimethylformamide, N,N-dimethylacetamide, dimethyl sulfoxide, acetonitrile and the like, and the like can be used. One kind thereof may be used or a mixture of two or more kinds thereof can also be used, and a mixture of a polar solvent and a nonpolar solvent can also be used.

The reaction temperature is generally −10° C.-50° C., preferably 0° C.-30° C.

The reaction time is 0.5 hr-5 hr.

Particularly, a compound represented by the formula (9) which is an n-propylamine salt or dimethylamine salt is preferable, since it has high crystallinity and can be obtained with a high purity.

The n-propylamine salt of (E)-7-[4-(4-fluorophenyl)-6-isopropyl-2-[methyl(methylsulfonyl)amino]pyrimidin-5-yl]-(3R,5S)-3,5-hydroxy-6-heptenoic acid has, for example, X-ray diffraction pattern shown below (powder X-ray diffraction patterns shown below were obtained in the below-mentioned Example 7).

TABLE 4

| 2θ | relative intensity |
|---|---|
| 6.0 | 9 |
| 6.4 | 4 |
| 8.1 | 0 |
| 10.0 | 18 |
| 10.8 | 33 |
| 11.8 | 1 |
| 12.8 | 8 |
| 13.7 | 12 |
| 15.3 | 39 |
| 16.3 | 15 |
| 16.8 | 18 |
| 17.8 | 9 |
| 18.5 | 20 |
| 19.1 | 16 |
| 19.8 | 64 |
| 20.9 | 48 |
| 21.6 | 15 |
| 22.9 | 100 |
| 23.8 | 9 |
| 24.4 | 11 |
| 25.3 | 17 |
| 25.6 | 16 |
| 26.8 | 31 |
| 28.1 | 15 |
| 29.1 | 12 |
| 30.3 | 19 |
| 32.6 | 8 |
| 34.2 | 11 |
| 35.4 | 12 |
| 36.5 | 7 |
| 37.6 | 11 |
| 38.9 | 9 |
| 41.0 | 8 |
| 42.0 | 8 |
| 43.7 | 8 |
| 45.7 | 9 |
| 46.8 | 9 |
| 48.6 | 5 |
| 51.2 | 4 |
| 52.7 | 5 |

That is, it has a powder X-ray diffraction pattern showing characteristic peaks at 2θ=19.8°, 22.9° (±0.2°). Furthermore, a powder X-ray diffraction pattern showing peaks at 2θ=10.8°, 15.3°, 19.8°, 20.9°, 22.9° (±0.2°) is preferable, and a powder X-ray diffraction pattern showing peaks at 2θ=10.0°, 10.8°, 15.3°, 16.8°, 18.5°, 19.8°, 20.9°, 22.9°, 26.8°, 30.3° (±0.2°) is more preferable. In addition, it may have a powder X-ray diffraction pattern showing peaks at 2θ=26.8°, 29.1°, 30.3°, 38.9°, 45.7° (±0.2°), and further optionally has a powder X-ray diffraction pattern showing peaks at 2θ=19.8°, 22.9°, 26.8°, 29.1°, 30.30, 34.2°, 36.5°, 38.9°, 45.7°, 46.8° (±0.2°).

In addition, the dimethylamine salt of (E)-7-[4-(4-fluorophenyl)-6-isopropyl-2-[methyl(methylsulfonyl)amino]pyrimidin-5-yl]-(3R,5S)-3,5-hydroxy-6-heptenoic acid has, for example, powder X-ray diffraction pattern shown below (powder X-ray diffraction patterns shown below were obtained in the below-mentioned Example 9).

TABLE 5

| 2θ | relative intensity |
|---|---|
| 6.6 | 100 |
| 10.1 | 60 |
| 10.4 | 18 |
| 11.8 | 12 |
| 12.9 | 14 |
| 13.5 | 62 |
| 17.0 | 74 |
| 17.9 | 16 |
| 18.3 | 46 |
| 18.9 | 34 |
| 19.4 | 28 |
| 19.6 | 24 |
| 20.5 | 36 |
| 21.2 | 24 |
| 22.4 | 18 |
| 24.0 | 22 |
| 27.7 | 12 |
| 28.8 | 12 |

That is, it has a powder X-ray diffraction pattern showing characteristic peaks at 2θ=6.6°, 17.0° (±0.2°). Furthermore, a powder X-ray diffraction pattern showing peaks at 2θ=6.6°, 10.1°, 13.5°, 17.0°, 18.3° (±0.2°) is preferable. Particularly, a powder X-ray diffraction pattern showing peaks at 2θ=6.6°, 10.1°, 13.5°, 17.0°, 18.3°, 18.9°, 19.4°, 19.6°, 20.5°, 21.2° (±0.2°) is more preferable.

Then, an amine salt represented by the formula (9) is salt-exchanged with a base to give a compound represented by the formula (7).

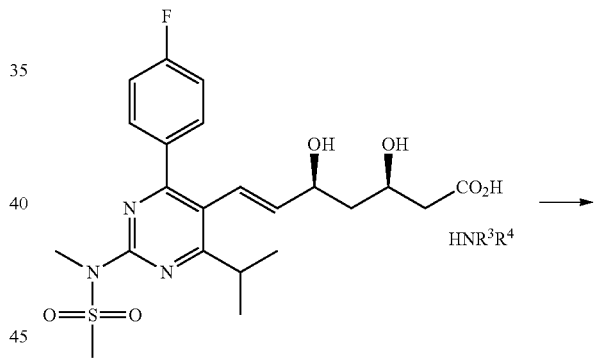

(9)

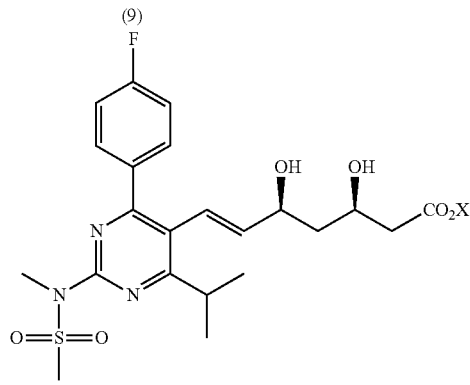

(7)

wherein $R^1$, $R^4$ and X are as defined above.

As the base, sodium hydroxide, potassium hydroxide and the like can be used, and sodium hydroxide is particularly preferable. The amount of the base to be used is generally 1 equivalent-3 equivalents, preferably 1 equivalent-2 equivalents, relative to a compound represented by the formula (9).

The reaction can be performed in a solvent. While the solvent is not particularly limited as long as the reaction proceeds, ether solvents such as MTBE, THF, CPME and the like, polar solvents such as N-methyl-2-pyrrolidone, N,N-dimethylformamide, N,N-dimethylacetamide, dimethyl sulfoxide, acetonitrile, water and the like, and the like can be used. One kind thereof may be used or a mixture of two or more kinds thereof can also be used, and a mixture of a polar solvent and a nonpolar solvent can also be used.

The reaction temperature is generally −10° C.-50° C., preferably 0° C.-30° C.

The reaction time is generally 0.5 hr-10 hr.

Furthermore, a compound represented by the formula (7) is reacted with a calcium compound to give rosuvastatin calcium represented by the formula (6).

used. One kind thereof may be used or a mixture of two or more kinds thereof can also be used, and a mixture of a polar solvent and a nonpolar solvent can also be used.

The reaction temperature is generally 0° C.-200° C., preferably 20° C.-110° C.

The reaction time is generally 0.01 hr-200 hr, preferably 0.5 hr-24 hr.

Step (iiic):

In step (iiic), a compound represented by the formula (2) is hydrolyzed with a base to give a compound represented by the formula (7), the compound represented by the formula (7) is subjected to intramolecular dehydration condensation in the presence or absence of an acid catalyst, and the obtained compound represented by the formula (10) is reacted with a calcium compound to give rosuvastatin calcium represented by the formula (6).

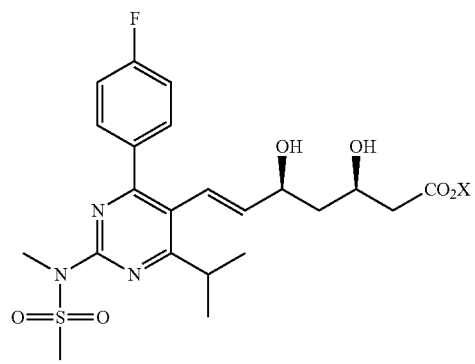

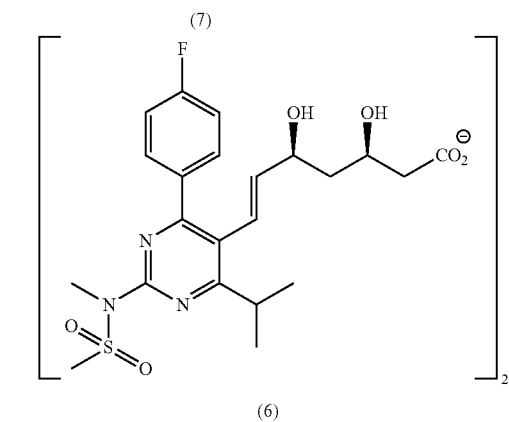

wherein X is as defined above.

As the calcium compound, calcium chloride, calcium acetate and the like can be used, and calcium chloride is particularly preferable. The amount of the calcium compound to be used is generally 0.5 equivalents-3 equivalents, preferably 0.6 equivalents-2.8 equivalents, relative to a compound represented by the formula (7).

The reaction can be performed in a solvent. While the solvent is not particularly limited as long as the reaction proceeds, ether solvents such as MTBE, THF, CPME and the like, polar solvents such as N-methyl-2-pyrrolidone, N,N-dimethylformamide, N,N-dimethylacetamide, dimethyl sulfoxide, acetonitrile, water and the like, and the like can be

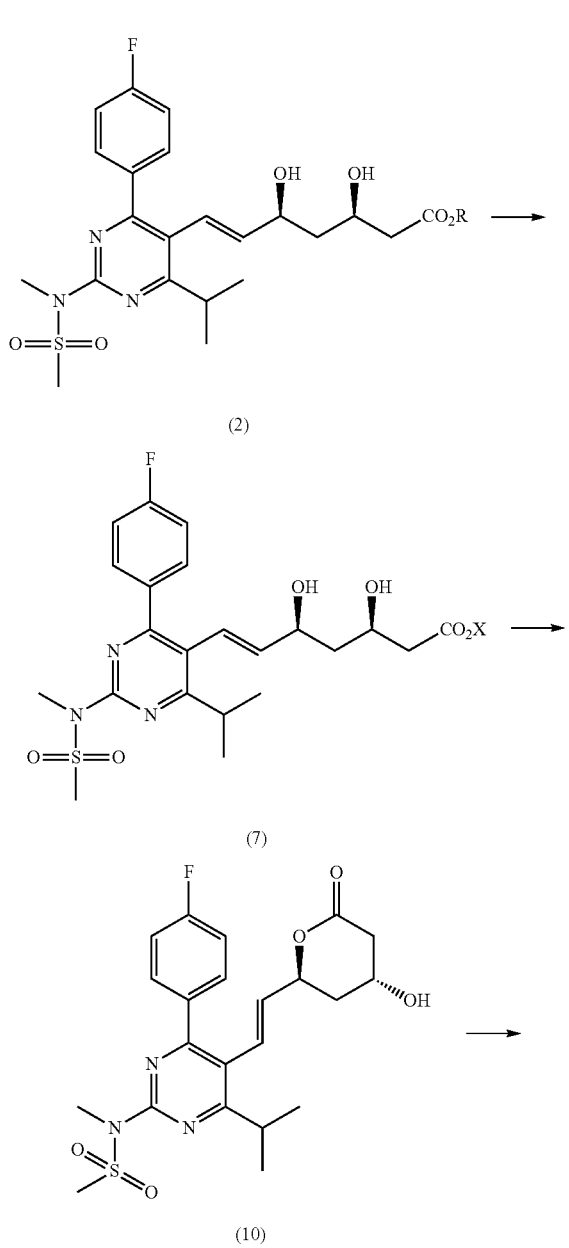

-continued

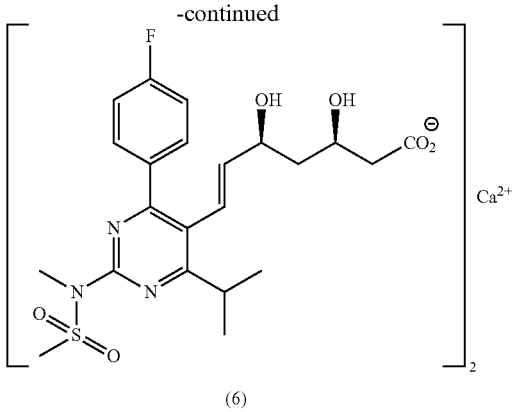

(6)

wherein R and X are as defined above.

A method similar to that in step (iiib) can be employed for the step wherein a compound represented by the formula (2) is hydrolyzed with a base to give a compound represented by the formula (7).

In the step wherein the compound represented by the formula (7) is subjected to intramolecular dehydration condensation in the presence or absence of an acid catalyst to give a compound represented by the formula (10), p-toluenesulfonic acid, pyridinium p-toluenesulfonate, sulfuric acid, hydrochloric acid and the like can be used as the acid catalyst and hydrochloric acid and p-toluenesulfonic acid are particularly preferable. The amount of the acid catalyst to be used is generally 0.001 equivalent-0.5 equivalents, preferably 0.01 equivalent-0.1 equivalent, relative to a compound represented by the formula (7).

The aforementioned intramolecular dehydration condensation can be performed in a solvent. While the solvent is not particularly limited as long as the reaction proceeds, ester solvents such as ethyl acetate, methyl acetate and the like, nonpolar solvents such as cyclohexane, n-hexane, n-heptane, toluene and the like, halogenated solvents such as methylene chloride, chloroform, carbon tetrachloride and the like, ether solvents such as MTBE, THF and the like, polar solvents such as N-methyl-2-pyrrolidone, N,N-dimethylformamide, N,N-dimethylacetamide, dimethyl sulfoxide and the like, and further, a mixture of a polar solvent and a nonpolar solvent is preferable. The amount of the solvent to be used is generally 1 mL-100 mL, preferably 5 mL-50 mL, relative to 1 g of a compound represented by the formula (7).

The reaction temperature is generally 0° C.-200° C., preferably 20° C.-110° C.

The reaction time is generally 1 hr-72 hr, preferably 1 hr-24 hr.

A method similar to that in step (iiib) can be employed for the step wherein the compound represented by the formula (10) is reacted with a calcium compound to give rosuvastatin calcium represented by the formula (6).

The production method of rosuvastatin calcium of the present invention preferably further includes the following step (B) as necessary. In step (B), (B) a compound represented by the following formula (12):

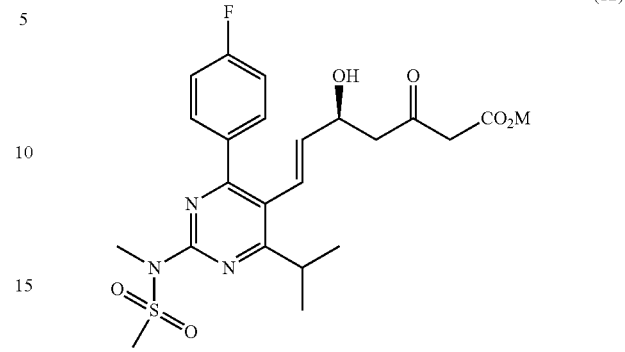

wherein M is an alkali metal element, an alkaline earth metal element or hydrogen, is converted to a compound represented by the following formula (13):

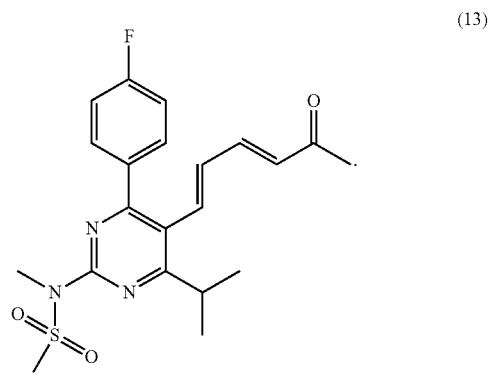 [SMILES: CC(=O)/C=C/C=C/c1c(-c2ccc(F)cc2)nc(N(C)S(C)(=O)=O)nc1C(C)C]

Particularly, step (B) can efficiently remove impurity represented by the aforementioned formula (12) and can further improve purity of rosuvastatin calcium. It is particularly preferable to include step (B) when the aforementioned step (iiia) is performed.

In the below-mentioned formula (16) and the aforementioned formula (12), M is preferably an alkali metal element. Here, the alkali metal element is preferably lithium, sodium or potassium, particularly preferably sodium.

The production method of the present invention preferably targets a compound represented by the formula (16) to be indicated later, which contains not less than 0.01 area %, more preferably not less than 0.05 area %, of a compound represented by the aforementioned formula (12), as measured by HPLC (High Performance Liquid Chromatography) (detection wavelength: UV 245 nm). While the upper limit is not particularly limited as long as the effect of the present invention can be obtained, it is generally not more than 99 area %, preferably not more than 50 area %, more preferably not more than 25 area %, particularly preferably not more than 5 area %, most preferably not more than 1 area %. In a particularly preferable embodiment of the present invention, a compound represented by the formula (16) to be indicated later contains not less than 0.01 area % and not more than 5 area % of a compound represented by the aforementioned formula (12).

The production method of the present invention preferably includes, prior to the aforementioned step (B), (Aa) a step of converting a mixture of a compound represented by the following formula (14):

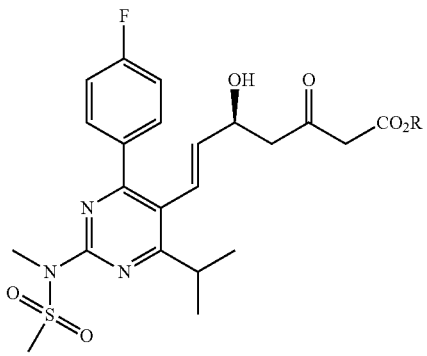

(14)

wherein R is a primary alkyl group having 1-8 carbon atoms or a secondary alkyl group having 3-6 carbon atoms, and a compound represented by the following formula (15):

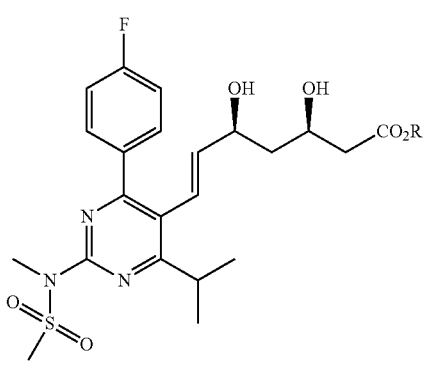

(15)

wherein R is as defined above, to a mixture of a compound represented by the following formula (16):

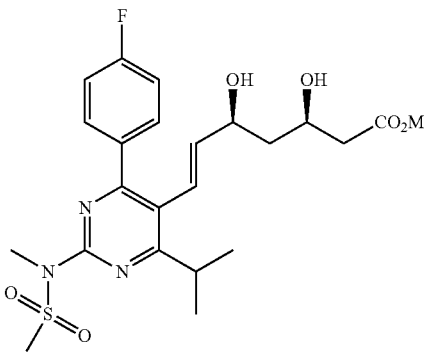

(16)

wherein M is alkali metal element, an alkaline earth metal element or hydrogen, and a compound represented by the aforementioned formula (12), by hydrolysis in the presence of a base.

In the aforementioned formulas (14) and (15), R is preferably methyl group, ethyl group, isopropyl group, n-propyl group, t-butyl group, s-butyl group, n-butyl group, more preferably methyl group, ethyl group, isopropyl group, n-propyl group, particularly preferably ethyl group, isopropyl group, n-propyl group.

In addition, (C) a step of removing a compound represented by the aforementioned formula (13) is preferably included after the aforementioned step (B).

Furthermore, (D) a step of reacting the compound obtained in the aforementioned step (C) with a calcium compound is preferably included after the aforementioned step (C).

The steps (Aa) and (B)-(D) of the production method of the present invention are explained below for each step.

Step (Aa):

In step (Aa), a mixture of a compound represented by the aforementioned formula (14) and a compound represented by the aforementioned formula (15) is converted to a mixture of a compound represented by the aforementioned formula (16) and a compound represented by the aforementioned formula (12) by hydrolysis in the presence of a base. In this case, the compound represented by the aforementioned formula (14) is converted to the compound represented by the aforementioned formula (12), and the compound represented by the aforementioned formula (15) is converted to the compound represented by the aforementioned formula (16).

The detail of step (Aa) is described in the explanation of the aforementioned step (iiia).

Step (B):

In step (B), a compound represented by the aforementioned formula (12) is converted to a compound represented by the aforementioned formula (13).

The reaction conditions and the like are not particularly limited as long as a compound represented by the aforementioned formula (12) can be converted to a compound represented by the aforementioned formula (13). A preferable example of the reaction conditions in step (B) is described below.

Step (B) is preferably performed in the presence of a solvent. Examples of the solvent here include ethers (e.g., methyl t-butyl ether, THF, cyclopentyl methyl ether and the like), acetic acid esters (e.g., methyl acetate, ethyl acetate, isopropyl acetate and the like), amides (e.g., N,N-dimethylformamide, N,N-dimethylacetamide and the like), hydrocarbons (e.g., toluene, cyclohexane and the like), alcohols (e.g., methanol, ethanol, isopropanol and the like), water and the like. Of these, methyl t-butyl ether, THF, ethyl acetate, toluene and water are preferable.

The reaction temperature is generally not less than 30° C., preferably not less than 40° C., and generally not more than 130° C., preferably not more than 100° C. To carry out the reaction efficiently, heating is preferably applied as necessary. In a particularly preferable embodiment of the present invention, step (B) is performed under the conditions of not less than 30° C. and not more than 130° C.

While the pH condition of step (B) is not particularly limited, acidic condition or basic condition is preferable for accelerating the reaction.

When the acidic condition is used, the step is preferably performed at not less than pH 0 and not more than pH 3. Examples of the acid that can be used here include hydrochloric acid, sulfuric acid, methanesulfonic acid, p-toluenesulfonic acid and the like, and hydrochloric acid or sulfuric acid is preferable.

When the basic condition is used, the step is preferably performed at not less than pH 10 and not more than pH 14. Examples of the base that can be used here include alkali metal hydroxide (e.g., sodium hydroxide, lithium hydroxide, potassium hydroxide and the like), calcium hydroxide, calcium carbonate, triethylamine, diisopropylethylamine and the like. Of these, sodium hydroxide and potassium hydroxide are preferable.

While the reaction time varies depending on other conditions, it is generally not less than 1 hr, preferably not less than 2 hr, and generally not more than 48 hr, preferably not more than 24 hr.

To shorten the above-mentioned reaction time, the reaction solution is preferably agitated as necessary in step (B).

In this step, generally, a compound represented by the aforementioned formula (16) is not particularly converted.

Step (C):

In step (C), a compound represented by the aforementioned formula (13) is removed from the mixture obtained in step (B). As used herein, removing does not necessarily mean complete removal, and the majority thereof only needs to be removed so that the purity of the obtained compound can be improved. When a compound represented by the aforementioned formula (13) is removed in this step, a compound represented by the aforementioned formula (16) remains.

The means and reaction conditions therefor are not particularly limited as long as a compound represented by the aforementioned formula (13) can be removed. A preferable example of step (C) is described below.

In step (C), a compound represented by the aforementioned formula (13) is preferably removed by extraction with an organic solvent under basic condition.

Examples of the organic solvent that can be used here include ethers (e.g., methyl t-butyl ether, cyclopentyl methyl ether (CPME) and the like), esters such as isopropyl acetate, ethyl acetate, methyl acetate and the like, toluene, ketones such as methyl ethyl ketone and the like, and the like. Of these, methyl t-butyl ether, cyclopentyl methyl ether, methyl ethyl ketone, and ethyl acetate are preferable.

Under basic condition preferably means not less than pH 8 and not more than pH 14, more preferably not less than pH 10 and not more than pH 14.

Examples of the base that can be used here include alkali metal hydroxide (e.g., sodium hydroxide, potassium hydroxide and the like), calcium hydroxide, calcium carbonate, triethylamine, diisopropylethylamine and the like. Of these, sodium hydroxide and potassium hydroxide are preferable.

Step (D):

In step (D), the compound obtained in the aforementioned step (C), namely, a compound represented by the aforementioned formula (16), and a calcium compound are reacted.

The reaction conditions and the like are not particularly limited as long as a calcium salt can be obtained by reacting the compound obtained in the aforementioned step (C) and a calcium compound. A preferable example of the reaction condition in step (D) and the like are described below.

As a calcium compound, calcium chloride, calcium acetate and the like can be used, and calcium chloride is particularly preferable. The amount of the calcium compound to be used is generally 0.5 equivalents-3 equivalents, preferably 0.6 equivalents-2.8 equivalents, relative to the compound obtained in the aforementioned step (C).

The reaction can be performed in a solvent. While the solvent is not particularly limited as long as the reaction proceeds, ether solvents such as MTBE, THF, CPME and the like, polar solvents such as N-methyl-2-pyrrolidone, N,N-dimethylformamide, N,N-dimethylacetamide, dimethyl sulfoxide, acetonitrile, water and the like, and further, a mixture of a polar solvent and a nonpolar solvent (e.g., toluene, cyclohexane, mesitylene and the like) is preferable.

The reaction temperature is generally 0° C.-200° C., preferably 20° C.-110° C.

The reaction time is generally 0.01 hr-200 hr, preferably 0.5 hr-24 hr.

[Purification Method of the Present Invention]

In the purification method of rosuvastatin calcium of the present invention, rosuvastatin calcium containing a compound represented by the aforementioned formula (12) can be purified. The purification method of the present invention can be performed for rosuvastatin calcium produced by the aforementioned production method of the present invention, or rosuvastatin calcium produced by other production method.

Rosuvastatin calcium here preferably targets a compound containing not less than 0.01 area %, more preferably not less than 0.05 area %, of a compound represented by the aforementioned formula (12), as measured by HPLC (High Performance Liquid Chromatography) (detection wavelength: UV 245 nm). While the upper limit is not particularly limited as long as the effect of the present invention can be obtained, it is generally not more than 99 area %, preferably not more than 50 area %, more preferably not more than 25 area %, particularly preferably not more than 5 area %, most preferably not more than 1 area %. In a particularly preferable embodiment of the present invention, rosuvastatin calcium contains not less than 0.01 area % and not more than 5 area % of a compound represented by the aforementioned formula (12).

The purification method of the present invention is characterized by comprising (B) a step of converting a compound represented by the aforementioned formula (12) to a compound represented by the aforementioned formula (13).

It is preferable to contain, prior to the aforementioned step (B), (Ab) a step of dissolving rosuvastatin calcium comprising a compound represented by the aforementioned formula (12) in a solvent.

Also, it is preferable to contain, after the aforementioned step (B), (C) a step of removing the compound represented by the aforementioned formula (13).

Furthermore, it is preferable to contain, after the aforementioned step (C), (D) a step of reacting the compound obtained by the aforementioned step (C) and a calcium compound.

The steps (Ab) and (B)-(D) of the purification method of the present invention are explained below for each step.

Step (Ab):

Step (Ab) is a step of dissolving rosuvastatin calcium comprising a compound represented by the aforementioned formula (12) in a solvent. As the solvent, ethers (e.g., methyl t-butyl ether, THF, cyclopentyl methyl ether (CPME) and the like), esters such as isopropyl acetate, ethyl acetate, methyl acetate and the like, toluene, ketones such as methyl ethyl ketone and the like, water and the like can be mentioned. Of these, ethers (e.g., methyl t-butyl ether, cyclopentyl methyl ether (CPME) and the like), esters such as isopropyl acetate, ethyl acetate, methyl acetate and the like, toluene, ketones such as methyl ethyl ketone and the like, and water are preferable.

In step (Ab), generally, rosuvastatin calcium (RSV-Ca) is converted to a compound represented by the following formula (17):

(17)

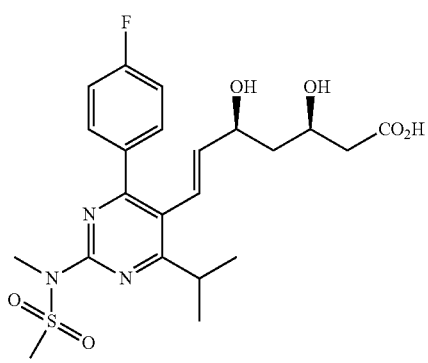

((3R, 5S, 6E)-7-[4-(4-fluorophenyl)-6-isopropyl-2-[methyl (methylsulfonyl)amino]pyrimidin-5-yl]-3,5-hydroxy-hept-6-enoic acid).

In this step, generally, a compound represented by the aforementioned formula (12) is not particularly converted.

Step (B):

In step (B), a compound represented by the aforementioned formula (12) is converted to a compound represented by the aforementioned formula (13).

In step (B), generally, a compound represented by the aforementioned formula (17) is converted to a compound represented by the aforementioned formula (16) according to the kind of the acid and base to be used for the above-mentioned reaction.

The reaction conditions and the like are not particularly limited as long as a compound represented by the aforementioned formula (12) can be converted to a compound represented by the aforementioned formula (13). A preferable example of the reaction condition in step (B) is described below.

Step (B) is preferably performed in the presence of a solvent. As the solvent, ethers (e.g., methyl t-butyl ether, THF, cyclopentyl methyl ether and the like), acetic acid esters (e.g., methyl acetate, ethyl acetate, isopropyl acetate and the like), amides (e.g., N,N-dimethylformamide, N,N-dimethylacetamide and the like), hydrocarbons (e.g., toluene, cyclohexane and the like), alcohols (e.g., methanol, ethanol, isopropanol and the like), water and the like can be mentioned. Of these, methyl t-butyl ether, THF, ethyl acetate, toluene, and water are preferable.

The reaction temperature is generally not less than 50° C., preferably not less than 60° C., and generally not more than 120° C., preferably not more than 110° C. To carry out the reaction efficiently, heating is preferably applied as necessary. In a particularly preferable embodiment of the present invention, step (B) is performed under the conditions of not less than 60° C. and not more than 100° C.

While the pH condition of step (B) is not particularly limited, acidic condition or basic condition is preferable for accelerating the reaction.

When the acidic condition is used, the step is preferably performed at not less than pH 0 and not more than pH 3. Examples of the acid that can be used here include hydrochloric acid, sulfuric acid, methanesulfonic acid, p-toluenesulfonic acid and the like. Of these, hydrochloric acid or sulfuric acid is preferable.

When the basic condition is used, the step is preferably performed at not less than pH 10 and not more than pH 14. Examples of the base that can be used here include alkali metal hydroxide (e.g., sodium hydroxide, potassium hydroxide and the like), calcium hydroxide, calcium carbonate, triethylamine, diisopropylethylamine and the like. Of these, sodium hydroxide and potassium hydroxide are preferable.

While the reaction time varies depending on other conditions, it is generally not less than 1 hr, preferably not less than 2 hr, and generally not more than 72 hr, preferably not more than 48 hr.

To shorten the above-mentioned reaction time, the reaction solution is preferably agitated as necessary in step (B).

Step (C):

In step (C), a compound represented by the aforementioned formula (13) is removed from the mixture (solution when step (Ab) is present) obtained in step (B). As used herein, removing does not necessarily mean complete removal, and the majority thereof only needs to be removed so that the purity of the obtained compound can be improved. When a compound represented by the aforementioned formula (13) is removed in this step, a compound represented by the aforementioned formula (16) remains.

The means and reaction conditions therefor are not particularly limited as long as a compound represented by the aforementioned formula (13) can be removed. A preferable example of step (C) is described below.

In step (C), a compound represented by the aforementioned formula (13) is preferably removed by extraction with an organic solvent under basic condition.

Examples of the organic solvent that can be used here include ethers (e.g., methyl t-butyl ether, cyclopentyl methyl ether (CPME) and the like), esters (e.g., isopropyl acetate, ethyl acetate, methyl acetate etc.), ketones (e.g., methyl ethyl ketone etc.), toluene and the like. Of these, the aforementioned ethers and esters are preferable. Of these, methyl t-butyl ether, cyclopentyl methyl ether, methyl ethyl ketone, and ethyl acetate are preferable.

Under basic condition preferably means not less than pH 8 and not more than pH 14, more preferably not less than pH 10 and not more than pH 14.

Examples of the base that can be used here include alkali metal hydroxide (e.g., sodium hydroxide, potassium hydroxide and the like), calcium hydroxide, calcium carbonate, triethylamine, diisopropylethylamine and the like. Of these, sodium hydroxide and potassium hydroxide are preferable.

Step (D):

In step (D), the compound obtained in the aforementioned step (C), namely, a compound represented by the aforementioned formula (16), and a calcium compound are reacted.

In step (D), a compound represented by the aforementioned formula (16) is converted to a calcium salt thereof, rosuvastatin calcium (RSV-Ca).

The reaction conditions and the like are not particularly limited as long as a calcium salt can be obtained by reacting the compound obtained in the aforementioned step (C) and a calcium compound. A preferable example of the reaction condition in step (D) and the like are described below.

As a calcium compound, calcium chloride, calcium acetate and the like can be used, and calcium chloride is particularly preferable. The amount of the calcium compound to be used is generally 0.5 equivalents-3 equivalents, preferably 0.6 equivalents-2.8 equivalents, relative to the compound obtained in the aforementioned step (C).

The reaction can be performed in a solvent. While the solvent is not particularly limited as long as the reaction proceeds, ether solvents such as MTBE, THF, CPME and the like, polar solvents such as N-methyl-2-pyrrolidone, N,N-dimethylformamide, N,N-dimethylacetamide, dimethyl sulfoxide, acetonitrile, water and the like, and further, a mixture of a polar solvent and a nonpolar solvent (e.g., toluene, cyclohexane, mesitylene and the like) is preferable.

The reaction temperature is generally 0° C.-200° C., preferably 20° C.-110° C.

The reaction time is generally 0.01 hr-200 hr, preferably 0.5 hr-24 hr.

[Rosuvastatin Calcium of the Present Invention]

Rosuvastatin calcium obtained by the production method of the present invention is highly pure, and the content of a compound represented by the following formula (11):

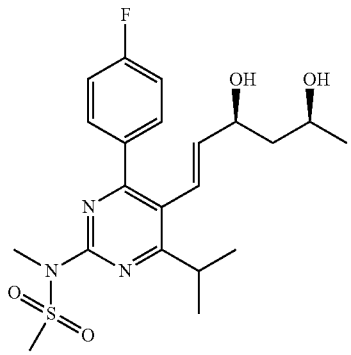

(11)

namely, 5-[trans-(3S,5R)-dihydroxyhexen-1-yl]-4-(4-fluorophenyl)-6-isopropyl-2-[methyl(methylsulfonyl)amino]pyrimidine, is preferably not more than 1500 ppm, more preferably not more than 1000 ppm, further preferably not more than 100 ppm, particularly preferably not more than 50 ppm, and preferably not less than 1 ppm. Such rosuvastatin calcium can be stably preserved.

The rosuvastatin calcium of the present invention contains a compound represented by the above-mentioned formula (13) at preferably not more than 1000 ppm, more preferably not more than 500 ppm, further preferably not more than 100 ppm. The content of a compound represented by the above-mentioned formula (13) is preferably not less than 1 ppm.

Rosuvastatin calcium containing a compound represented by the above-mentioned formula (13) at not less than 1 ppm and not more than 1000 ppm can be stably preserved.

In the present invention, powder X-ray diffraction spectrum can be measured by a known method. For example, a sample is filled on a glass sample plate, X-ray at a wavelength of 1.5406 angstrom emitted from a ceramic X-ray tube Cu operated at 45 kV and 40 mA is irradiated on the sample and measured. Since the values of powder X-ray diffraction spectrum 2θ varies, for example, within a ±0.2° error range depending on the measurement device and sample, the 2θ values in the present invention should not be interpreted as absolute values.

EXAMPLES

The present invention is explained in more detail in the following by referring to Examples, which are not to be construed as limitative.

The quantitative analysis in the Examples included measurement under the following conditions by using HPLC (High Performans Liquid Chromatography).

<Chemical Purity of DHAB>
Column: Shiseido Co., Ltd. manufactured by Capcell Pack C18 MG (4.6 mm×75 mm, 3 μm)
Mobile phase: A: 0.1 mol/L ammonium acetate, 0.1 mmol/L ethylene diamine tetraacetic acid disodium salt B: 10% mobile phase A, 90% methanol
Gradient program (B concentration): 40% (0 min)→100% (12 min)→100% (14 min)
Flow rate: 1 mL/min Column temperature: 40° C.
Detection wavelength: UV 254 nm <Chemical Purity of DOXP>
Column: Capcell Pak C18 MG (4.6 mm×75 mm, 3 μm) manufactured by Shiseido Co., Ltd.
Mobile phase: A: water/acetic acid/ammonium acetate=1000/100/7.7 (mL/mL/g) B: THF
Gradient program (B concentration): 38% (0 min)→38% (17 min)→80% (27 min)
Flow rate: 1 mL/min Column temperature: 40° C.
Detection wavelength: UV 254 nm <Chemical Purity of DOXE>
Column: Capcell Pak C18 MG (4.6 mm×75 mm, 3 μm) manufactured by Shiseido Co., Ltd.
Mobile phase: A: water/acetic acid/ammonium acetate=1000/100/7.7 (mL/mL/g) B: THF
Gradient program (B concentration): 41% (0 min)→41% (17 min)→90% (27 min)
Flow rate: 1 mL/min Column temperature: 40° C.
Detection wavelength: UV 254 nm <Chemical Purity of DOLP>
Column: Capcell Pak C18 MGIII-H (2.0 mm×100 mm, 3 μm) manufactured by Shiseido Co., Ltd.
Mobile phase: A: 0.1 M ammonium acetate/ethanol=3/2 (mL/mL) B: 0.1 M ammonium acetate/ethanol=1/4 (mL/mL)
Gradient program (B concentration): 0% (0 min)→0% (10 min)→100% (25 min)→100% (30 min)
Flow rate: 0.3 mL/min Column temperature: 40° C.
Detection wavelength: UV 245 nm In Examples 4 and 5, the following conditions were used for the measurement.
Column: Cadenza CD-C18 (4.6 mm×150 mm, 3 μm) manufactured by Imtakt Inc.
Mobile phase: A: 0.1% aqueous formic acid solution B: ethanol
Gradient program (B concentration): 40% (0 min)→60% (20 min)→80% (25 min)
Flow rate: 0.8 mL/min Column temperature: 40° C.
Detection wavelength: UV 245 nm <Chemical Purity of RSV-Ca>
Column: Cadenza CD-C18 (4.6 mm×250 mm, 3 μm) manufactured by Imtakt Inc.
Mobile phase: A: 0.1% aqueous formic acid solution B: methanol containing 0.1% formic acid
Gradient program (B concentration): 60% (0 min)→75% (12 min)→100% (20 min)
Flow rate: 0.8 mL/min Column temperature: 40° C.
Detection wavelength: UV 245 nm <Optical Purity of RSV-Ca>
Column: Chiralpak IB (4.6 mm×250 mm, 3 μm) manufactured by Daicel Corporation
Mobile phase: trifluoroacetic acid/hexane/ethanol=0.1/90/10 (mL/mL/mL)
Flow rate: 1 mL/min Column temperature: 25° C.
Detection wavelength: UV 245 nm <Analysis of DOLH in RSV-Ca>
Column: Cadenza CD-C18 (4.6 mm×250 mm, 3 m) manufactured by Imtakt Inc.
Mobile phase: A: 0.1% aqueous formic acid solution B: methanol containing 0.1% formic acid
Gradient program (B concentration): 60% (0 min)→75% (12 min)→100% (20 min)
Flow rate: 0.8 mL/min Column temperature: 40° C.
Detector: MS (polarity: positive mode: SIM fragmentor: 200 dry gas flow rate: 5 L/min nebulizer: 40 psi dry gas temperature: 250° C. vaporizer temperature: 150° C.)

<Powder X-ray Diffraction Spectrum of DOXP and DOLP>
The powder X-ray diffraction spectrum of DOXP and DOLP (Examples 2, 2', 5, and 11) was measured using X-ray diffraction apparatus XRD-6000 (manufactured by Shimadzu Corporation). X-ray at a wavelength of 1.5406 angstrom emitted from a ceramic X-ray tube Cu was irradiated on a sample. An X-ray source set in parallel was passed through an automatic divergence slit, and the reflected X-ray was measured by a high-speed semiconductor detector. A high-speed semiconductor detector was attached to the instrument. The measurement conditions were as follows.
Monochromator: used
Tube voltage: 40.0 Kv
Tube current: 40.0 mA
Divergence: 1.00 deg
Scattering: 1.00 deg
Receiving: 0.15 mm
Mode: continuous scan
Driving shaft: 2θ/θ
Data range: 5-40 deg
Step: 0.02 deg
Scan speed: 3.5000 deg/min (run time: 10 min)
Rotating speed: 60 rpm
<Powder X-ray Diffraction Spectrum of Propylamine Salt>

The powder X-ray diffraction spectrum of propylamine salt (Example 7) was measured under the same conditions as in <powder X-ray diffraction spectrum of DOXP and DOLP> except that an X-ray diffraction apparatus X'Pert-PRO MPD (manufactured by Spectris Co., Ltd.) was used and the measurement conditions were set to the following.
Monochromator: used
Tube voltage: 45.0 Kv
Tube current: 40.0 mA
Divergence: automatic
Irradiation width: 10.00 mm
Sample width: 10.00 mm
Mode: continuous scan
Driving shaft: 2θ/θ,
Data range: 5-40 deg
Step: 0.017 deg
Scan step time [s]: 10.9834
Implementation time: 10 min and 40 sec
<Powder X-ray Diffraction Spectrum of Dimethylamine Salt>

The powder X-ray diffraction spectrum of dimethylamine salt (Example 9) was measured under the same conditions as in the above-mentioned <Powder X-ray diffraction spectrum of DOXP and DOLP> except that an X-ray diffraction apparatus RAD-RB (manufactured by Rigaku Co., Ltd.) was used and the measurement conditions were set to the following.
Monochromator: used
Tube voltage: 40.0 Kv
Tube current: 100 mA
Divergence slit: 1.00 deg
Scattering slit: 1.00 deg
Receiving slit: 0.15 mm
Mode: continuous scan
Driving shaft: 2θ/θ
Data range: 2-40 deg
Step: 0.02 deg
Scan speed: 2 deg/min (Implementation time: 19 min)

Reference Example 1

Synthesis of DHAB (t-butyl 3,5-dioxohexanoate)

[Step 1]

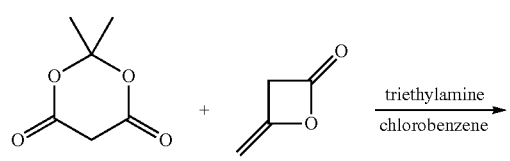

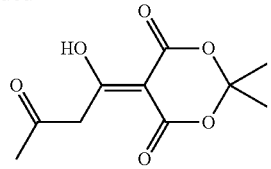

Under a nitrogen atmosphere, Meldrum's acid (MA) (900.1 g, 6.24 mol) and chlorobenzene (4532.1 g) were charged in a 10 L flask and, after start of stirring, the inside temperature was adjusted to 20° C. To the mixture was added dropwise triethylamine (631.9 g, 6.24 mol) over 25 min. After stirring for 30 min, to the mixture was added dropwise diketene (DK) (557.8 g, 6.86 mol) over 2 hr. After stirring at inside temperature 22° C. for 1.5 hr, to the reaction mixture was added dropwise a mixture of 35% hydrochloric acid (651.4 g) and water (1799.9 g) over 1 hr 20 min. The organic layer was separated, and washed with water. The obtained organic layer was dried over dry SK1B (H type ion exchange resin, manufactured by Mitsubishi Chemical Corporation).

After drying, the organic layer was filtered and used in the next step.

[Step 2]

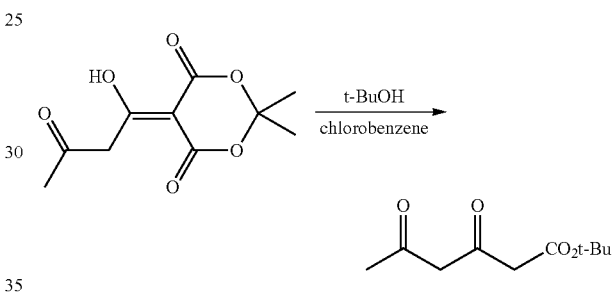

Under a nitrogen atmosphere, the organic layer obtained in the previous step was charged into a 10 L flask, and tert-butanol (555.4 g, 7.48 mol) was added. The mixture was heated to an inside temperature of 60° C. After stirring for 7 hr, the reaction mixture was cooled to room temperature. To the reaction mixture was added 7% aqueous sodium hydrogen carbonate solution (1325.8 g) and the reaction mixture was filtered. Then, the organic layer was separated, and washed with water. The organic layer was concentrated until the organic solvent was not distilled off at 60° C.

The residue was purified by thin film distillation apparatus (pressure: 50 Pa-80 Pa, heat transfer medium temperature: 110° C.). The obtained tert-butyl 3,5-dioxo-hexanoate (DHAB) was 893 g (yield: 69%) and purity by HPLC was 92.1 area %.

$^1$H-NMR (400 MHz, CDCl$_3$, tautomeric mixture) δ 1.43-1.49 (9H, m), 2.07 (2.5H, s), 2.25 (0.5H, s), 3.24 (1.7H, s), 3.46 (0.3H, s), 3.73 (0.3H, s), 5.61 (0.7H, s)

Reference Example 2

Synthesis Method of DHAE (ethyl 3,5-dioxohexanoate)

[Step 1]

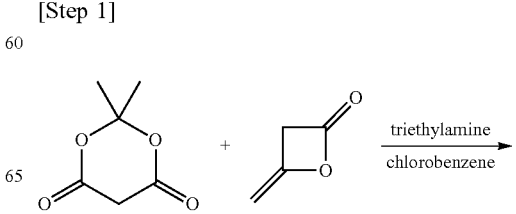

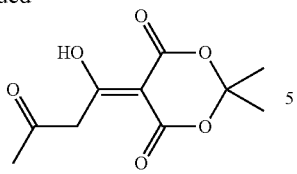

Under a nitrogen atmosphere, Meldrum's acid (MA) (100.2 g, 0.69 mol) and chlorobenzene (554 g) were charged in a 2 L flask and, after start of stirring, the inside temperature was adjusted to 20° C. To the mixture was added dropwise triethylamine (70.3 g, 0.69 mol) over 17 min. After stirring for 1 hr, to the mixture was added dropwise diketene (64.6 g, 0.76 mol) over 1 hr 20 min. After stirring at an inside temperature 25° C. for 5.5 hr, to the reaction mixture was added dropwise a mixed solution of 35% hydrochloric acid (72.3 g) and water (277.5 g), prepared in advance, over 30 min. The organic layer was separated, and washed with water. The obtained organic layer was dried over dry SK1B (H type ion exchange resin, manufactured by Mitsubishi Chemical Corporation).

After drying, the organic layer was filtered and used in the next step.

[Step 2]

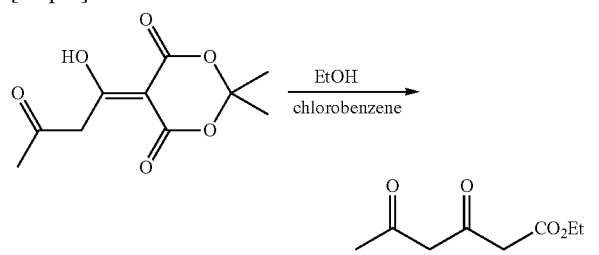

Under a nitrogen atmosphere, the organic layer obtained in the previous step was charged into a 2 L flask, and ethanol (38.5 g, 0.83 mol) was added. The mixture was heated to an inside temperature 60° C. After stirring for 9 hr, the reaction mixture was cooled to room temperature. To the reaction mixture was added 7% aqueous sodium hydrogen carbonate solution (87.2 g), and the reaction mixture was filtered. The organic layer was separated, and the organic layer was washed with water. The organic layer was concentrated until the organic solvent was not distilled off at 60° C.

The residue was purified by single distillation apparatus (pressure: 50 Pa-80 Pa, heat transfer medium temperature: 110° C.). The obtained ethyl 3,5-dioxo-hexanoate (DHAE) was 83.5 g (yield: 70%) and purity by HPLC was 97.9 area %.

Example 1

Production of DOXP (n-propyl (E)-7-[4-(4-fluorophenyl)-6-isopropyl-2-[methyl(methylsulfonyl)amino]pyrimidin-5-yl]-3,5-dioxo-6-heptenoate)

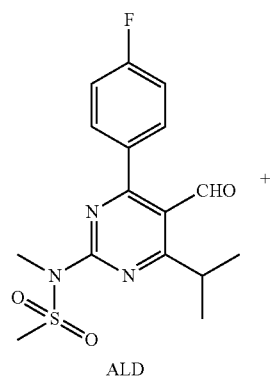

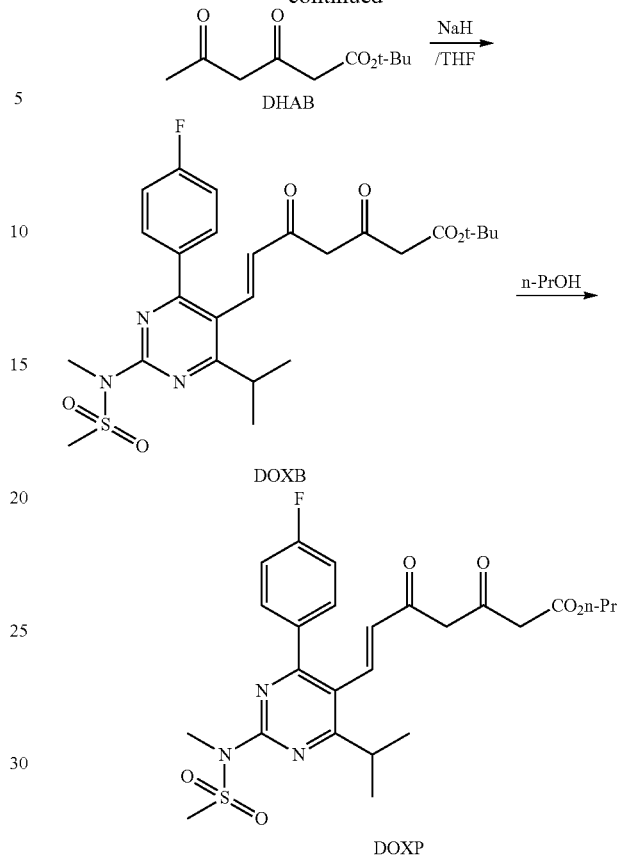

Under a nitrogen atmosphere, sodium hydride (5.50 g) (purity 62.1%, 142 mmol) and tetrahydrofuran (50 mL) were charged in a flask, and the mixture was cooled to 0° C.-5° C. To the mixture was added dropwise a solution of DHAB (68.3 mmol) obtained in Reference Example 1 in tetrahydrofuran (50 mL) over 1 hr. After the completion of the dropwise addition, the mixture was stirred at 0° C.-5° C. for 1 hr. (reaction mixture A)

Under a nitrogen atmosphere, 4-(4-fluorophenyl)-5-formyl-6-isopropyl-2-[methyl(methylsulfonyl)amino]pyrimidine (ALD (commercially available product)) (10.0 g, 28.5 mmol) and methyl tert-butyl ether (100 mL) were charged in a flask, and cooled to 0° C.-5° C. Thereafter, the reaction mixture A was added dropwise at the same temperature. After the completion of the dropwise addition, the inside temperature was heated to 20° C. over 2 hr, and the mixture was stirred at 20° C. for 4 hr. As a result of analysis by HPLC, the conversion ratio to DOXB (tert-butyl (E)-7-[4-(4-fluorophenyl)-6-isopropyl-2-[methyl(methylsulfonyl)amino]pyrimidin-5-yl]-3,5-dioxo-6-heptenoate) was 97.0%.

Thereafter, the inside temperature was cooled to 10° C., and water (100 mL) was added dropwise. After dropwise addition, the mixture was warmed to room temperature and the aqueous layer was separated by partitioning. Then, the organic layer was washed with 2% aqueous sodium hydroxide solution (50.0 g) (NaOH 1.0 g, water 49.0 g), 10% aqueous citric acid solution (50.0 g) (citric acid 5.0 g, water 45.0 g), 2% aqueous NaCl solution (60.0 g) (NaCl 2.0 g, water 58.0 g) in this order. The obtained organic layer was quantitatively analyzed by HPLC to find yield from ALD of 87.0%.

The obtained organic layer was concentrated under reduced pressure at an outer temperature 35° C. To the obtained residue was added n-propanol and the mixture was concentrated under reduced pressure at an outer temperature of 40° C. After concentration, to the residue was again added n-propanol and the mixture was concentrated under reduced pressure at an outer temperature of 40° C.

Thereafter, to the obtained residue was added n-propanol to adjust the liquid volume to 50 mL, and the mixture was heated to an inside temperature of 100° C. After 7.5 hr, analysis by HPLC revealed that the conversion ratio to DOXP was 99.0%. Thereafter, and the mixture was cooled and concentration under reduced pressure was started when the inside temperature was 60° C., and the mixture was concentrated until the solution volume reached 30 mL. When the inside temperature was adjusted to 45° C., a seed crystal of DOXP was added and the mixture was gradually cooled to 0° C.-5° C. After cooling, crystals were recovered by solid-liquid separation. The purity of the obtained crystals by HPLC was 95.5 area %.

The obtained crystal and methanol (31 mL) were charged in a 100 mL separable flask, and the mixture was heated to a refluxing temperature of the solvent to give a homogeneous solution. After confirmation of complete dissolution of the crystals, the inside temperature was lowered to 45° C. The seed crystal of DOXP was added at an inside temperature of 45° C., and the mixture was cooled to 0° C. over 2 hr. After cooling, the crystals were recovered by solid-liquid separation. The obtained wet crystals were dried under reduced pressure. The purity of the obtained DOXP by HPLC was 97.4 area %, and the recovery amount was 9.59 g (yield 64.7%).

$^1$H-NMR (400 MHz, CDCl$_3$) δ 0.92-0.96 (3H, t, J=7.5 Hz), 1.29 (3H, s), 1.31 (3H, s), 1.64-1.70 (2H, q, J=7.0 Hz), 3.36-3.42 (2H, m), 3.52 (3H, s), 3.59 (3H, s), 4.09-4.12 (2H, t, J=6.5 Hz), 5.53 (1H, s), 5.79-5.83 (1H, d, J=15.9 Hz), 7.10-7.15 (2H, m), 7.61-7.68 (3H, m)

(Production of Seed Crystal of DOXP)

Under a nitrogen atmosphere, sodium hydride (52.5 g) (purity 65%, 1.42 mol) and tetrahydrofuran (0.5 L) were charged in a reactor, and the mixture was cooled to an inside temperature of 0° C.-5° C. In a separate reaction kettle, under a nitrogen atmosphere, a solution of DHAB (137.0 g, 0.683 mol) synthesized in the same manner as in Reference Example 1 and tetrahydrofuran (0.5 L) was prepared. The solution of DHAB in tetrahydrofuran was added dropwise to a solution of sodium hydride in tetrahydrofuran over 1 hr, and the mixture was stirred at 0° C.-5° C. for 1 hr. (reaction mixture B)

Under a nitrogen atmosphere, 4-(4-fluorophenyl)-5-formyl-6-isopropyl-2-[methyl(methylsulfonyl)amino]pyrimidine (ALD) (100 g, 0.281 mol) and tetrahydrofuran (1 L) were charged in a reactor, and the mixture was cooled to 0° C.-5° C. Thereafter, the reaction mixture B was added dropwise while controlling to an inside temperature of 0° C.-5° C. After the completion of the dropwise addition, the mixture was stirred at the same temperature for 5 hr. As a result of analysis by HPLC, the conversion ratio from ALD was 99.2%.

After completion of the reaction, methyl tert-butyl ether (1 L) was added, water (1 L) was added dropwise while controlling to an inside temperature of 0° C.-5° C. After dropwise addition, the aqueous layer was separated by partitioning. Then, the organic layer was washed with 2% aqueous NaCl solution (500 g) (NaCl 10 g, water 490 g), 10% aqueous citric acid solution (1000 g) (citric acid 100 g, water 900 g), and water (500 g) in this order. The obtained organic layer was quantitatively analyzed by HPLC and DOXB was obtained from ALD at a yield of 83.2%.

The obtained organic layer was concentrated under reduced pressure at an outer temperature of 35° C. to a total amount of 500 g. To the obtained residue was added i-propanol (200 mL) and the mixture was concentrated under reduced pressure at an outer temperature of 40° C. to a total amount of 500 g. This operation was repeated three times.

Thereafter, the inside temperature was cooled to 0-5° C. over 1 hr, and the crystals were recovered by solid-liquid separation. The obtained crystals were dried under reduced pressure to give DOXB. The purity of the obtained DOXB by HPLC was 98.7 area %, and the recovery rate was 98.7 g (yield 65%).

To DOXB (1 g) obtained by the above-mentioned method was added n-propanol (10 mL), and the mixture was heated to an inside temperature of 98° C. After 10 hr, and the mixture was analyzed by HPLC to find a conversion ratio to DOXP of 99.5%.

The reaction mixture was concentrated, the obtained residue was purified by flash column chromatography (eluent: heptane/ethyl acetate=94/6 to 50/50 (volume ratio), linear gradient), a fraction containing a large amount of the object product was recovered, and concentrated at an outer temperature of 50° C. The obtained residue was dried under reduced pressure, whereby DOXP was crystallized. The purity of the obtained DOXP by HPLC was 97.2 area % and the recovery amount was 1.01 g (yield 103%).

Example 2

(Production of DOXP)

Under a nitrogen atmosphere, sodium hydride (8.28 kg) (purity 61.9%, 214 mol) and tetrahydrofuran (75 L) were charged in a reactor, and the mixture was cooled to an inside temperature of 0° C.-5° C. In a separate reactor, under a nitrogen atmosphere, a solution of DHAB (20.5 kg, 103 mol) synthesized in the same manner as in Reference Example 1 and tetrahydrofuran (75 L) was prepared. The solution of DHAB in tetrahydrofuran was added dropwise to a solution of sodium hydride in tetrahydrofuran over 5 hr, and the mixture was stirred at 0° C.-5° C. for 1 hr. (reaction mixture C)

Under a nitrogen atmosphere, 4-(4-fluorophenyl)-5-formyl-6-isopropyl-2-[methyl(methylsulfonyl)amino]pyrimidine (ALD) (14.9 kg, 42.4 mol) and methyl tert-butyl ether (150 L) were charged in a reactor, and the mixture was cooled to 0° ° C.-5° C. Thereafter, the reaction mixture C was added dropwise while controlling the inside temperature at 0° C.-5° C. After the completion of the dropwise addition, the inside temperature was warmed to 20° C.-25° C. over 2 hr, and the mixture was stirred at 20° C.-25° C. for 2 hr. As a result of analysis by HPLC, the conversion ratio from ALD was 99.3%.

After completion of the reaction, the inside temperature was cooled to 20° C. or below, and water (150 L) was added dropwise while maintaining at 20° C. or below. After dropwise addition, the aqueous layer was separated by partitioning. Then, the organic layer was washed with 2% aqueous sodium hydroxide solution (75.0 kg) (NaOH 1.5 kg, water 73.5 kg), 10% aqueous citric acid solution (75.0 kg) (citric acid 7.5 kg, water 67.5 kg), 2% aqueous NaCl solution (75.0 kg) (NaCl 1.5 kg, water 73.5 kg) in this order. The obtained organic layer was quantitatively analyzed by HPLC and DOXB was obtained from ALD at a yield of 82.8%.

The obtained organic layer was concentrated under reduced pressure at an outer temperature of 35° C. to a total amount of 30 L. To the obtained residue was added n-propanol (75 L) and the mixture was concentrated under reduced pressure at an outer temperature of 40° C. to a total amount of 30 L.

Thereafter, n-propanol (38 L) was added to the obtained residue and the inside temperature was elevated to 97° C. After reaction for 8 hr, and the mixture was analyzed by HPLC to find a conversion ratio to DOXP of 99.3%.

The mixture was concentrated under reduced pressure at an inside temperature of 60° C., and the solution volume was concentrated to 45 L. Thereafter, and the mixture was cooled to an inside temperature of 45° C., and the seed crystal of DOXP was added at the same temperature. The mixture was cooled to 0° C.-5° C. over 4 hr, and the crystals were recovered by solid-liquid separation. The purity of the obtained crystals by HPLC was 98.1 area %.

The obtained crystals and methanol (50 L) were charged in a 120 L reaction vessel, and the mixture was heated to give a homogeneous solution. After confirmation of complete dissolution of the crystals, the inside temperature was adjusted to 45° C. and the seed crystal of DOXP was added. The mixture was cooled to 0° C.-5° C. over 4 hr, and the crystals were recovered by solid-liquid separation. The obtained crystals were dried under reduced pressure to give DOXP. The purity of the obtained DOXP by HPLC was 99.0 area %, and the recovery amount was 14.0 kg (yield 63.4%).

The powder X-ray diffraction spectrum of the obtained DOXP crystal is shown in FIG. 1.

Example 2'

(Production of DOXP)

Under a nitrogen atmosphere, in a reactor, sodium hydride (17.1 kg) (purity 60%, 427 mol) was dissolved in tetrahydrofuran (THF) (150 L), and the mixture was cooled to an inside temperature of 0° C.-5° C. (solution D).

In a separate reactor, under a nitrogen atmosphere, methyl t-butyl ether (150 L) was added to dissolve DHAB (41 kg, 204 mol) synthesized in the same manner as in Reference Example 1. While controlling the inside temperature to 10° C. or below, the obtained solution was added dropwise to solution D (a solution of sodium hydride in THF) (solution E).

In a separate reactor, 4-(4-fluorophenyl)-5-formyl-6-isopropyl-2-[methyl(methylsulfonyl)amino]pyrimidine (ALD) (30 kg, 85.3 mol) was dissolved in THF (300 L). The solution was added dropwise to solution E while controlling the inside temperature to 0° C.-5° C. After the completion of the dropwise addition, and the mixture was warmed to an inside temperature of 20° C.-25° C., and stirred at the same temperature for 7 hr. As a result of analysis by HPLC, the remaining amount of ALD was 0.7%.

Thereafter, water (300 L) was added dropwise. After partitioning, the obtained organic layer was washed 3 times. As the solvent, 2% brine, 10% aqueous citric acid solution, and 2% brine were used in this order. The washed organic layer was concentrated under reduced pressure at an outer temperature of around 45° C. To the obtained residue was added n-propanol and the mixture was concentrated again under reduced pressure at an outer temperature of around 45° C.

To the obtained residue was added n-propanol, and the mixture was warmed until n-propanol was refluxed and maintained in this state for 10 hr. The obtained solution was analyzed by HPLC to find the remaining amount of DOXB of 1.6%.

The obtained solution was concentrated under reduced pressure at an outer temperature of 60° C.-70° C. Thereafter, the mixture was cooled to an inside temperature of 42° C.-45° C., and the seed crystal of DOXP was added at the same temperature. The mixture was cooled to −50° C.-0° C. over 4 hr, and wet crystals were recovered by solid-liquid separation.

The obtained wet crystals and n-propanol (60 kg) were charged in a reactor, the temperature of the mixture was raised and the mixture was heated under reflux for 1 hr. Thereafter, the inside temperature was adjusted to 42° C.-45° C., and the seed crystal of DOXP was added. Thereafter, the mixture was cooled to −5° C.-0° C. over 4 hr, and wet crystals were recovered by solid-liquid separation. The obtained wet crystals were dried under reduced pressure to give DOXP as crystals. The purity of the obtained DOXP crystals was 99.0 area % by HPLC, and the recovery amount was 23.2 kg (yield 52%).

Figure 2:
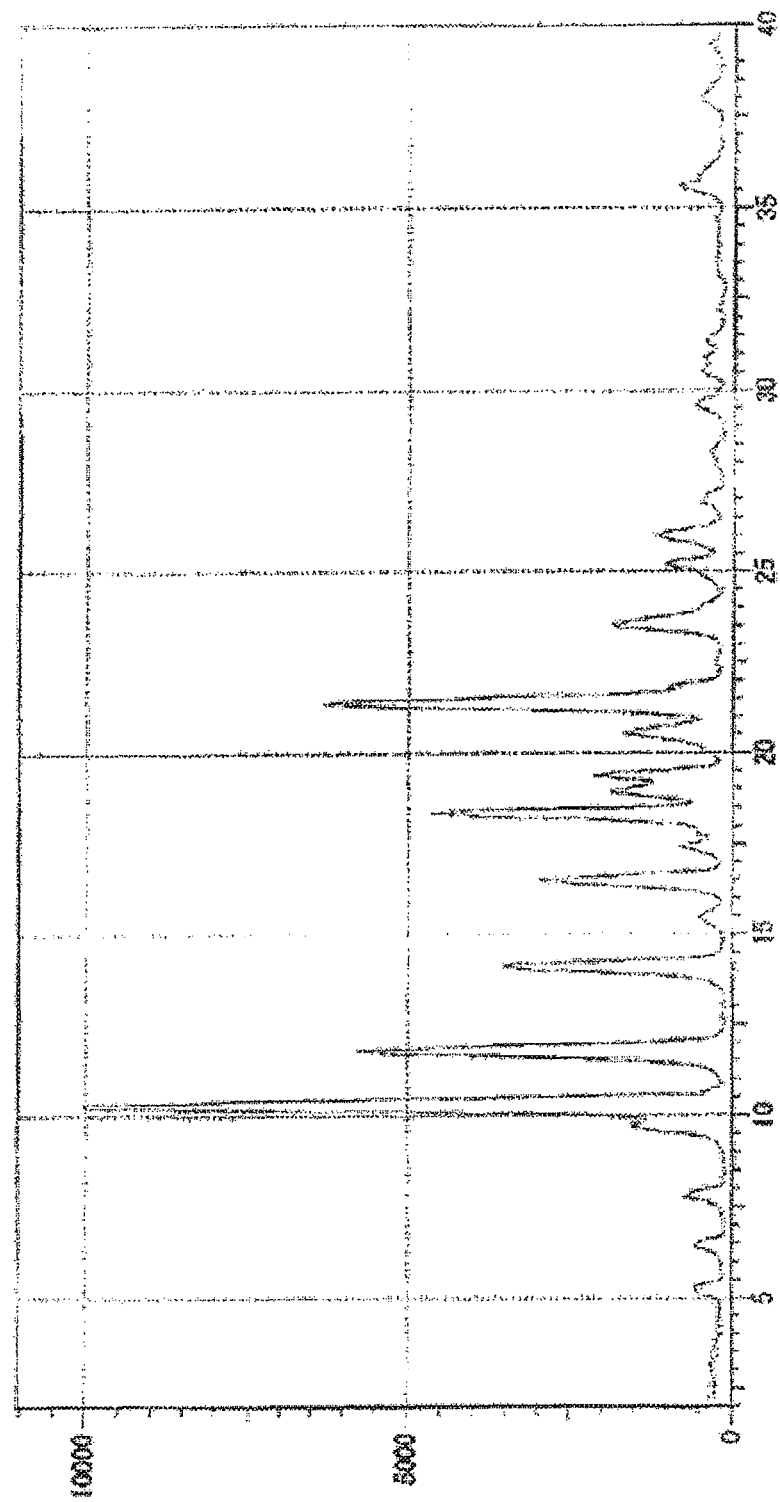
FIG. 2 shows the powder X-ray diffraction pattern of the compound obtained in Example 2', wherein the vertical axis shows intensity and the horizontal axis shows 2θ (°)

The powder X-ray diffraction spectrum of the obtained DOXP crystals is shown in FIG. 2.

Example 3

(Production of DOXP by Condensation Using Sodium Amide)

Under a nitrogen atmosphere, sodium amide (5.5 g, 142 mmol) and tetrahydrofuran (THF) (50 mL) were charged in a 250 mL separable flask. After cooling to an inside temperature of 2° C., a solution of DHAB (14.8 g) synthesized in the same manner as in Reference Example 1 in THF (50 mL) was added dropwise while controlling the temperature between 2° C.-5° C. After the completion of the dropwise addition, the mixture was stirred at an inside temperature of 3° C. for 1 hr. To this mixture was added a solution of ALD (10 g, 28.5 mmol) in MTBE (100 mL) while controlling the temperature to 0° C.-1° C. After the completion of the dropwise addition, the mixture was stirred at an inside temperature of 0° C. for 3 hr, the temperature was raised to 10° C. and the mixture was further stirred for 3.5 hr. Thereafter, to the reaction mixture was added water (100 g). After partitioning, the obtained organic layer was washed with 2 wt % aqueous sodium hydroxide solution (50 g), 10 wt % aqueous citric acid solution (50 g), and 2 wt % aqueous sodium hydroxide solution (50 g) in this order. The obtained organic layer was quantitatively analyzed by HPLC, and DOXB was obtained from ALD at a yield of 70%.

Thereafter, the organic layer was concentrated under reduced pressure at an outer temperature of 40° C., n-propanol (50 mL) was added to the residue, and the mixture was concentrated again under reduced pressure at an outer temperature of 40° C. n-Propanol was added to make the volume of the obtained residue 40 mL, and the inside temperature was raised to 97° C. The mixture was reacted at the same temperature for 5 hr, and the reaction mixture was cooled to 45° C., and the seed crystal of DOXP was added. The reaction mixture was cooled to 0° C., and the obtained crystals were collected by filtration. To the recovered crystals was added methanol (30 mL), and the mixture was dissolved by raising the inside temperature to 52° C. The solution was cooled to 40° C., and the seed crystal of DOXP was added. The solution was cooled to 0° C., and the obtained crystals were collected by filtration. The crystals dried under reduced pressure at 40° C. The weight of the obtained crystals was 7.7 g, and by quantitative analysis by HPLC, the yield from ALD was 54% and the purity was 97.8 area %.

Example 1'

Synthesis of DOXE (ethyl (E)-7-[4-(4-fluorophenyl)-6-isopropyl-2-[methyl(methylsulfonyl)amino]pyrimidin-5-yl]-3,5-dioxo-6-heptenoate))

[Step 1]

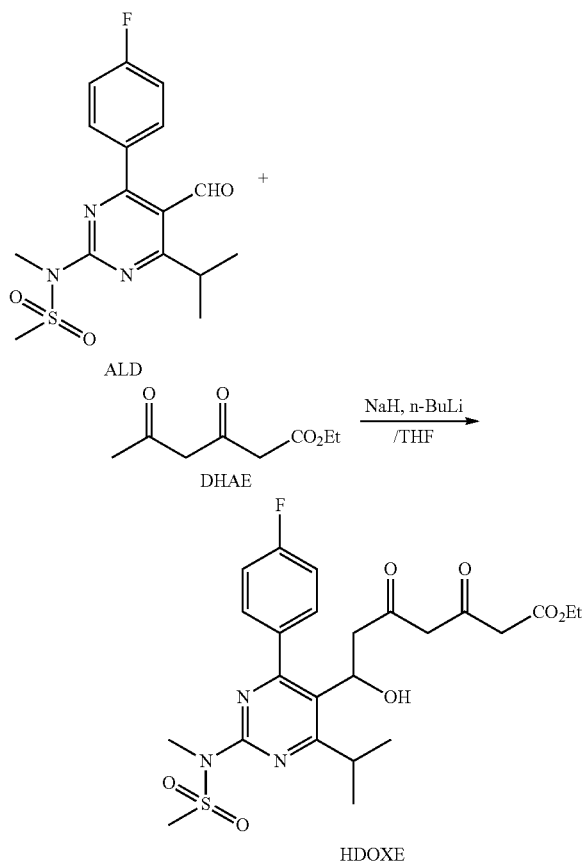

Under a nitrogen atmosphere, 60% sodium hydride (1.2 g, 29.9 mmol) was charged in a 200 mL three-necked flask, and anhydrous n-pentane (10 mL) was added. After stirring for 5 min, the mixture was stood and the supernatant was removed. Thereafter, THF (50 mL) was added, and the mixture was cooled to an inside temperature of −10° C. A solution of DHAE (4.9 g, 28.5 mmol) synthesized in Reference Example 2 in THF (10 mL) solution was added dropwise while maintaining the inside temperature of around −10° C. After stirring at around −10° C. for 50 min, the mixture was cooled to an inside temperature of −30° C. Thereafter, a solution of 1.3 mol/L n-butyllithium in THF (40.6 mL, 56, 9 mmol) was added dropwise while maintaining the inside temperature between −27° C. and −25° C. After the completion of the dropwise addition, the mixture was stirred at an inside temperature of −15° C. for 40 min. The mixture was cooled to an inside temperature of −30° C. and a solution of ALD (5 g, 14.2 mmol) in THF (90 mL) was added dropwise. The reaction mixture was warmed to an inside temperature of 0° C., and stirred for 2 hr. Thereafter, acetic acid (6.8 mL) was added dropwise at an inside temperature of around 0° C., and toluene (50 mL) and water (40 mL) were added. After partitioning, the obtained organic layer was washed with water (25 mL), and then with 25 wt % aqueous sodium hydroxide solution (25 mL). Thereafter, the organic solvent was evaporated under reduced pressure to give a crude product of HDOXE (ethyl 7-[4-(4-fluorophenyl)-6-isopropyl-2-[methyl(methylsulfonyl)amino]pyrimidin-5-yl]-7-hydroxy-3,5-dioxo-6-heptenoate) (9.2 g).

[Step 2]

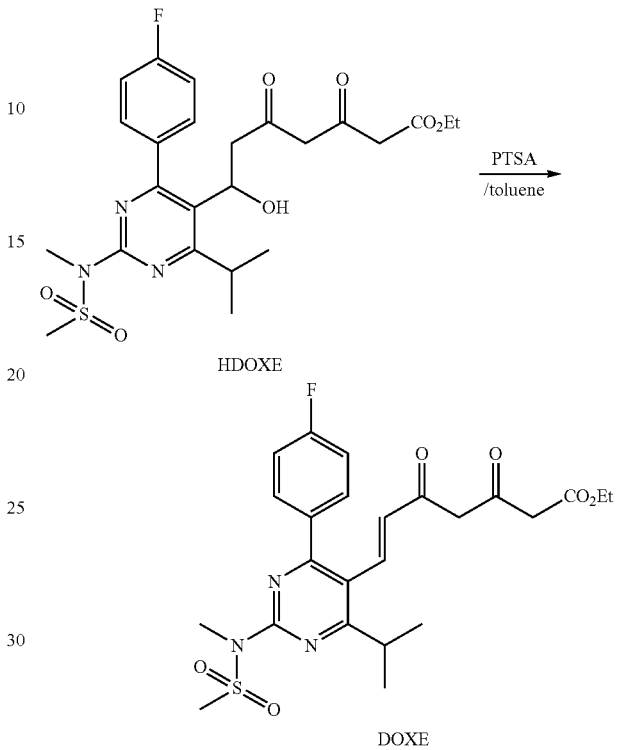

Under a nitrogen atmosphere, the crude product of HDOXE (3.7 g) (net amount equivalent 2.9 g, 5.67 mmol) obtained in the previous step, p-toluenesulfonic acid (PTSA) (0.11 g, 0.57 mmol) and toluene (60 mL) were charged in a 100 mL three-necked flask. Thereafter, the inside temperature was raised to 110° C. and the mixture was refluxed for 4 hr. Thereafter, the reaction mixture was cooled to 25° C., and saturated aqueous sodium hydrogen carbonate (20 mL) was added to the mixture. After partitioning, the obtained organic layer was dried over sodium sulfate. The dried organic layer was filtered, and the solvent was evaporated. The obtained residue was purified by silica gel column chromatography (eluent: hexane/ethyl acetate=100/0-90/10). The main fraction was concentrated to give the object DOXE (0.92 g, 32%, purity 89 area %) as an oil $^1$H-NMR (400 MHz, CDCl$_3$, tautomeric mixture) δ 1.22-1.31 (9H, m), 3.25-3.41 (3H, m), 3.52 (3H, s), 3.59 (3H, s), 4.18-4.23 (2H, q, J=4.5 Hz), 5.30 (0.7H, s), 5.52 (1.3H, s), 5.79-5.83 (1H, d, J=10.1 Hz), 7.11-7.16 (2H, m), 7.60-7.69 (3H, m)

Reference Example 3

(Preparation of Cells)
[Preparation Example of Recombinant *Escherichia coli* JM109/pKV32OCR1-GDH Co-Expressing Carbonylreductase (Hereinafter OCR1) and Glucose-1-Dehydrogenase (Hereinafter GDH)]

(1) Cloning of Gene

Primers ocr1_F (SEQ ID NO: 3) and ocr1_R (SEQ ID NO: 4) for amplifying full-length ocr1 gene were designed and synthesized based on OCR1 (JP-B-4270918, SEQ ID NO: 2) derived from the gene sequence (ocr1) encoding *Ogataea minuta* variant *nonfermentans* (*Ogataea minuta* var. *nonfermentans*) NBRC (former IFO) 1473. Then, PCR was performed according to a conventional method and using chromosome DNA of *Ogataea-Minuta* variant *nonfermentans* (*Ogataea minuta* var. *nonfermentans*) as a template to give an about 0.8 kbp DNA fragment.

Then, based on a gene sequence (hereinafter gdh (SEQ ID NO: 5)) encoding GDH (SEQ ID NO: 6), which is glucose-1-dehydrogenase encoded by a gene (GeneBank Accession No. AL009126.3) derived from *Bacillus subtilis* (*Bacillus subtilis*) wherein glutamic acid, which is the 96th amino acid residue, is substituted by alanine, primer gdh_F1 (SEQ ID NO: 7) and gdh_R1 (SEQ ID NO: 8) for amplifying full-length gdh gene were designed and synthesized. Then, PCR was performed according to a conventional method to give an about 0.8 kbp DNA fragment.

(2) Preparation of Expression Plasmid

The DNA fragment of ocr1 obtained in the above-mentioned (1) was digested with restriction enzymes EcoRI and HindIII, and introduced into the downstream of trc promoter in the plasmid pKV32 described in JP-A-2005-34025 and digested with MunI and HindIII, by using Ligation-Convenience Kit (manufactured by Nippon Gene Co., Ltd.) to give pKV32OCR1.

Then, the DNA fragment of gdh obtained in the above-mentioned (1) was digested with restriction enzymes EcoRI and XbaI, and introduced into the downstream of trc promoter in the plasmid pKV32 digested with MunI and XbaI, by using Ligation-Convenience Kit (manufactured by Nippon Gene Co., Ltd.) to give pKV32GDH.

Using pKV32GDH as a template and primers gdh_F2 (SEQ ID NO: 9) and gdh_R2 (SEQ ID NO: 10) added with restriction enzyme site HindIII, PCR was performed, and the obtained fragment was digested with restriction enzyme HindIII and inserted into the downstream of plasmid pKV32OCR1 digested with restriction enzyme HindIII in advance to give pKV32OCR1-GDH. The orientation of gdh gene in the obtained plasmid was confirmed by PCR.

(3) Preparation of Expression Strain

Using plasmid pKV32OCR1-GDH obtained in the above-mentioned (2), *Escherichia coli* JM109 (manufactured by TAKARA BIO INC.) was transformed according to a conventional method to give recombinant *Escherichia coli* JM109/pKV32OCR1-GDH.

Example 4

Production of DOLP (n-propyl (3R), (5S), (6E)-7-[4-(4-fluorophenyl)-6-isopropyl-2-[methyl(methylsulfonyl)amino]pyrimidin-5-yl]-3,5-dihydroxy-6-heptenoate)

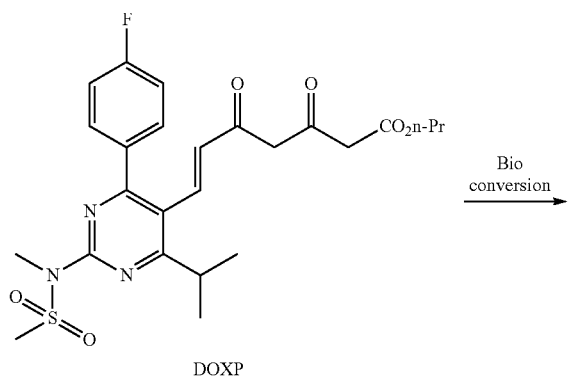

DOXP

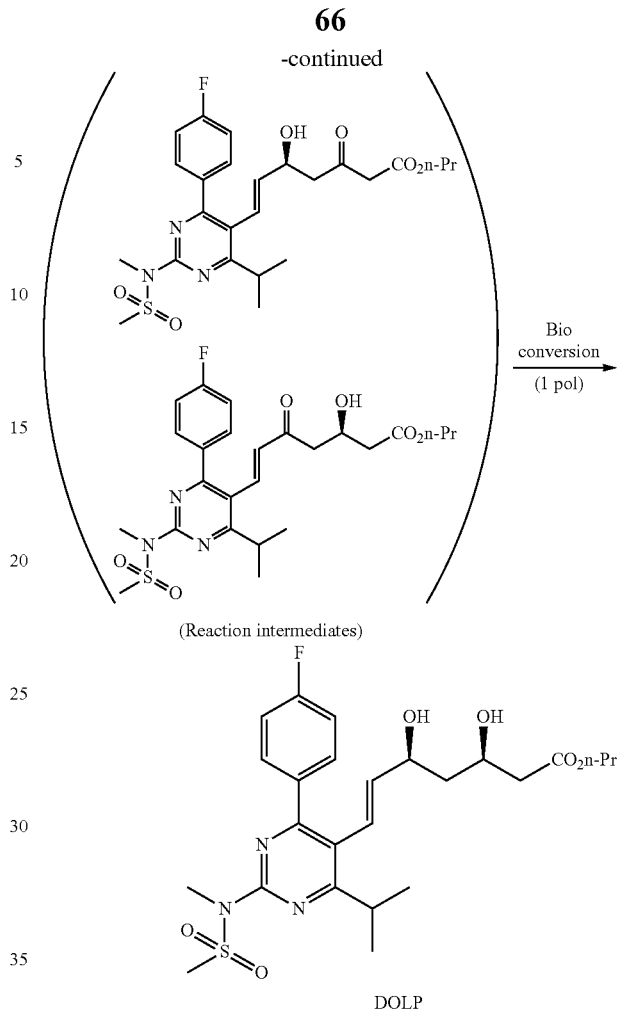

(Reaction intermediates)

DOLP

Ion exchange water (385.9 mL), glucose (19.5 g, 108.2 mmol), NADP+ (manufactured by Oriental Yeast Co., Ltd.) (75 mg, 0.1 mmol), dipotassium hydrogen phosphate (0.5 g, 2.9 mmol), and potassium dihydrogen phosphate (3.8 g, 27.9 mmol) were charged in a 1 L jar fermentor (manufactured by Able Co., Ltd., Model BMJ-01) and dissolved therein. Thereto were added frozen cells (55.6 g) of recombinant *Escherichia coli* JM109/pKV32OCR1-GDH prepared by the method of Reference Example 3 and the total amount of a substrate solution prepared by dissolving DOXP (7.0 g, 13.5 mmol) in dimethyl sulfoxide (DMSO) (86.3 g, 1111.4 mmol), and the mixture was stirred at an inside temperature of 50° C. for 3 hr. During the reaction, 25 wt % aqueous sodium hydroxide solution was added dropwise to maintain pH 6.5. The obtained reaction mixture was centrifuged at 10,000 rpm for 10 min to give a precipitate consisting of cells and reaction resultant product. The precipitate was suspended in a 5 wt % aqueous sodium sulfate solution, and extracted with ethyl acetate. Extraction with ethyl acetate was repeated three times, the obtained extracts were mixed and the mixed extract was analyzed by HPLC. As a result, the yield of DOLP was 6.05 g (yield 85.8%).

$^1$H-NMR (400 MHz, CDCl$_3$) δ 0.95 (3H, t, J=7.6 Hz), 1.26 (6H, d, J=7.2 Hz), 1.44-1.70 (4H, m), 2.48 (2H, d, J=6.8 Hz), 3.36 (1H, m), 3.52 (3H, s), 3.57 (3H, s), 3.62 (1H, s), 3.76 (1H, s), 4.09 (2H, t, J=6.8 Hz), 4.21 (1H, m), 4.46 (1H, m), 5.45 (1H, dd, J=5.6 Hz, 16.0 Hz), 6.64 (1H, d, J=16.0 Hz), 7.09 (2H, m), 7.64 (2H, m)

Example s 4-1-4-4

(Production of DOLP)

DOLP was produced under the same conditions as in Example 4 except that ion exchange water, glycerol, glucose (48.3 g, 268.1 mmol), NADP$^+$ (manufactured by Oriental Yeast Co., Ltd.) (138 mg, 0.18 mmol), dipotassium hydrogen phosphate (8.29 g, 47.6 mmol), and potassium dihydrogen phosphate (3.97 g, 29.2 mmol) were charged to achieve the glycerol concentration described in Table 6, the amount of the frozen cells of recombinant *Escherichia coli* JM109/pKV32OCR1-GDH to be used was set to 50.60 g, the substrate solution was a solution prepared by dissolving DOXP (14.4 g, 27.7 mmol) in dimethyl sulfoxide (DMSO) (124.20 g, 1589.7 mmol), the reaction time was set to 5 hr, and pH 6 was maintained during the reaction. The conversion ratio to DOLP is shown in Table 6. It is clear that the conversion ratio is improved by performing the reaction in the presence of glycerol. Production of DOLP was confirmed by the retention time of HPLC.

TABLE 6

|  | glycerol concentration (g/L) | conversion ratio (%) |
|---|---|---|
| Example 4-1 | 255 | 95.78 |
| Example 4-2 | 170 | 94.22 |
| Example 4-3 | 85 | 92.54 |
| Example 4-4 | 0 | 90.25 |

Example 5

(Production of DOLP)

Ion exchange water (1929.6 mL), glucose (97.7 g, 542.2 mmol), NADP$^+$ (manufactured by Oriental Yeast Co., Ltd.) (374 mg, 0.49 mmol), dipotassium hydrogen phosphate (2.6 g, 14.9 mmol) and potassium dihydrogen phosphate (19.1 g, 140.3 mmol) were charged in a 5 L jar fermenter (Model BMS manufactured by Able Co., Ltd.) and dissolved therein. Thereto were added frozen cells (278 g) of recombinant *Escherichia coli* JM109/pKV32OCR1-GDH prepared by the method of Reference Example 3 and the total amount of a substrate solution prepared by dissolving DOXP (35 g, 67.4 mmol) in DMSO (434.1 g, 5556.1 mmol), and the mixture was stirred at an inside temperature of 50° C. for 3 hr. During the reaction, 25 wt % aqueous sodium hydroxide solution was added dropwise to maintain pH 6.5. The obtained reaction mixture was centrifuged at 10,000 rpm for 10 min to give a precipitate consisting of cells and reaction resultant product. The precipitate was suspended in a 5 wt % aqueous sodium sulfate solution, and extracted with ethyl acetate. Extraction with ethyl acetate was repeated three times, the obtained extracts were mixed and the mixed extract was analyzed by HPLC. As a result, the yield of DOLP was 29.5 g (yield 83.7%).

(DOLP Isolation)

An ethyl acetate extract (containing 24.1 g of DOLP) of a biologically reduced reaction mixture of DOLP was concentrated under reduced pressure at an outer temperature of 40° C. After concentration, methanol was added, and the mixture was concentrated again under reduced pressure at an outer temperature of 40° C. to give a methanol solution (72.4 g) of DOLP (DOLP 24.1 g, methanol 48.3 g). To this solution were added water (36.2 g) and methanol (18.6 g) to give a 70% aqueous methanol solution containing 5 volume ratio to DOLP. This solution was heated to 50° C.-60° C. to give a homogeneous solution, and a seed crystal of DOLP was added at an inside temperature of 48° C. The mixture was cooled to an inside temperature of 40° C. over 2 hr, and stirred at said temperature for 30 min. Thereafter, the mixture was cooled to an inside temperature of 3° C. over 2 hr, stirred for 30 min, and the crystals were recovered by solid-liquid separation. The weight of the obtained wet crystals was 35.4 g. The wet crystals were dried under reduced pressure at 40° C. to give DOLP in a dried form. The recovery amount of DOLP in the dried form was 22.1 q, and the purity was 97.3 area %.

DOLP (40.7 g) (HPLC purity 98.9 area %) and toluene (204 mL) were charged in a flask, and the mixture was heated to an inside temperature of 65° C. to give a homogeneous solution. After confirmation of complete dissolution of DOLP, the mixture was cooled to an inside temperature of 45° C. A seed crystal of DOLP was added at an inside temperature of 45° C. and the mixture was stirred for 1 hr. After the completion of stirring, the inside temperature was adjusted to 50° C. and the mixture was stirred for 1 hr. After the completion of stirring, and the mixture was cooled to 0° C.-5° C. at a cooling rate of 10° C./hr, and stirred at said temperature for 1 hr. After the completion of stirring, the crystals were recovered by solid-liquid separation. The obtained wet crystals were dried under reduced pressure to give purified DOLP. The purity of the obtained purified DOLP by HPLC was 99.4 area %, the recovery amount was 38.1 g, and the recovery rate was 93.6%.

Figure 3:
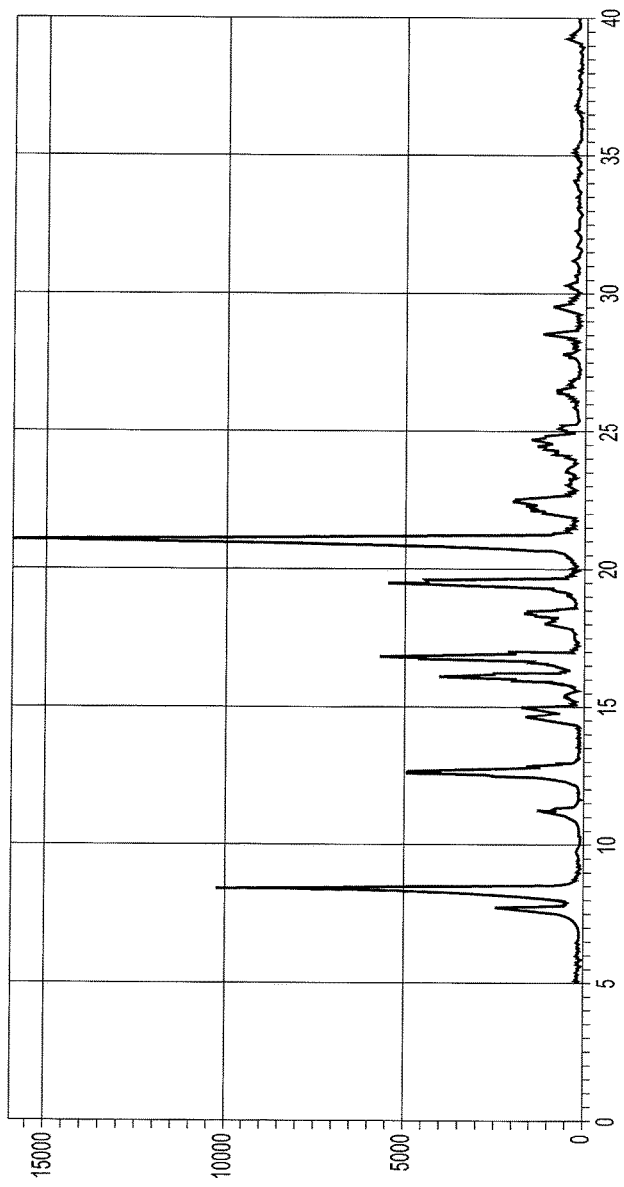
FIG. 3 shows the powder X-ray diffraction pattern of the compound (DOLP(n-propyl ((3R), (5S), (6E))-7-[4-(4-fluorophenyl)-6-isopropyl-2-[methyl(methylsulfonyl)amino]pyrimidin-5-yl]-3,5-dihydroxy-6-heptenoate)) obtained in Example 5, wherein the vertical axis shows intensity and the horizontal axis shows 2θ (°).

The powder X-ray diffraction spectrum of the obtained purified DOXP crystals is shown in FIG. 3.

(Production of Seed Crystal of DOLP)

An ethyl acetate solution containing 0.7 g of DOLP produced according to the method described in Example 4 was concentrated under reduced pressure. The obtained residue was purified by flash column chromatography (eluent:ethyl acetate/heptane=10/90 to 80/20 (volume ratio), linear gradient). A fraction containing a large amount of the object product was recovered and concentrated under reduced pressure. As a result, DOLP was crystallized. The purity of the obtained crystals was 98.7 area %, and the recovery amount was 0.4 g.

Example 5-1

DOLP (66.2 g) (HPLC purity 98.1 area %) produced according to the method described in Example 5 and toluene (400 g) were charged under a nitrogen atmosphere, and the mixture was heated until DOLP was dissolved. After confirmation of complete dissolution of DOLP, the mixture was cooled to 29° C.-31° C., seed crystal DOLP was added at the same temperature (the seed crystal was produced according to the method described in Example 5), and the mixture was stirred for 10 min. Thereafter, the mixture was heated to 50-52° C. and stirred for 1.5 hr. The obtained slurry was cooled to around 1° C. over 5 hr, and the crystals were recovered by solid-liquid separation. The obtained wet crystals were dried under reduced pressure.

The recovery amount of purified DOLP was 64.7 g. The HPLC purity of purified DOLP was 99.0 area %, which was improved by 0.9 area % from that at the time of charging.

Example 5-2

DOLP (65.3 g) (HPLC purity 97.9 area %) produced according to the method described in Example 5 and toluene (395 g) were charged under a nitrogen atmosphere, and the mixture was heated until DOLP was dissolved. After confirmation of complete dissolution of DOLP, the mixture was cooled to 34° C.-36° C., seed crystal DOLP was added at the same temperature (the seed crystal was produced according to the method described in Example 5), and the mixture was stirred for 30 min. Thereafter, the mixture was heated to 50-52° C. and stirred for 1.5 hr. The obtained slurry was cooled to around 1° C. over 11 hr, and the crystals were recovered by solid-liquid separation. The obtained wet crystals were dried under reduced pressure.

The recovery amount of purified DOLP was 63.1 g. The HPLC purity of purified DOLP was 99.3 area %, which was improved by 1.4 area % from that at the time of charging.

Example 5-3

DOLP (48.7 g) (HPLC purity 96.9 area %) produced according to the method described in Example 5 and toluene (210 g) were charged under a nitrogen atmosphere, and the mixture was heated until DOLP was dissolved. After confirmation of complete dissolution of DOLP, the mixture was cooled to 38° C.-41° C., seed crystal DOLP was added at the same temperature (the seed crystal was produced according to the method described in Example 5), and the mixture was stirred for 1 hr. Thereafter, the mixture was cooled to 33° C.-35° C., and stirred for 1 hr. The mixture was further heated to 50-53° C. and stirred for 10 min. The obtained slurry was cooled to around 3° C. over 14.5 hr, and the crystals were recovered by solid-liquid separation. The obtained wet crystals were dried under reduced pressure.

The recovery amount of purified DOLP was 46.2 g. The HPLC purity of purified DOLP was 99.5 area %, which was improved by 2.6 area % from that at the time of charging.

TABLE 7

| | aging conditions | cooling rate | purity (area %) | difference from purity on charging (area %) |
|---|---|---|---|---|
| Example 5-1 | 29-31° C. (10 min) →50-52° C. (1.5 hr) | 10.0° C./hr | 99.0 | 0.9 |
| Example 5-2 | 34-36° C. (30 min) →50-52° C. (1.5 hr) | 4.6° C./hr | 99.3 | 1.4 |
| Example 5-3 | 38-41° C. (1 hr) →33-35° C. (1 hr) →50-53° C. (10 min) | 3.3° C./hr | 99.5 | 2.5 |

Example 6

(Production of RSV-Ca)

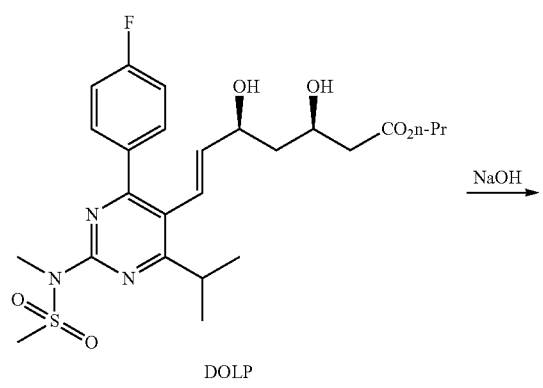

DOLP

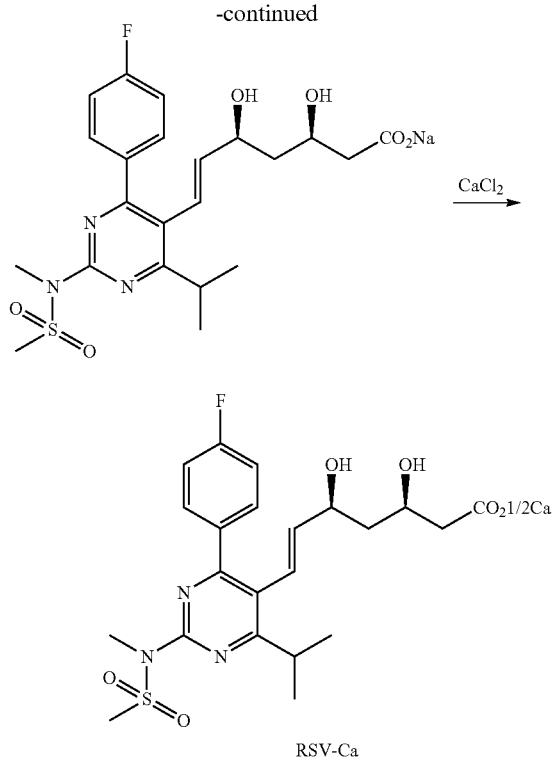

RSV-Ca

Under a nitrogen atmosphere, DOLP (36 g, 68.8 mmol) and ethanol (666 g) were charged in a flask and dissolved therein. Thereafter, water (766.8 g) was added. To the mixture was added dropwise 2 mol/L aqueous sodium hydroxide solution (38.5 mL, 77.0 mmol) at an inside temperature of 23° C. over 7 min. After stirring for 2 hr, the reaction mixture was concentrated and ethanol was evaporated. To the obtained solution was added ethyl acetate (144 g). After stirring for 20 min, the mixture was partitioned. This operation was repeated twice. Ethyl acetate contained in the obtained aqueous layer was evaporated by concentration under reduced pressure. 2 mol/L Aqueous sodium hydroxide solution was added to adjust the obtained solution to around pH 12, and the mixture was cooled to an inside temperature of 9° C. Thereafter, 0.17 mol/L aqueous calcium chloride solution (451 g) was added dropwise over 24 min. After stirring at the same temperature for 2 hr, the precipitated crystals were collected by filtration. The recovered crystals were dried under reduced pressure at 40° C. The obtained crystals (28.5 g, 83%) contained 3.4% of moisture. As a result of analysis by HPLC, the chemical purity of the obtained rosuvastatin calcium (RSV-Ca) crystals was 99.7 area %, and the optical purity was 100% e.e.

$^1$H-NMR (400 MHz, DMSO) δ 1.12 (3H, d, J=8.4 Hz), 1.23 (1H, m), 1.45 (1H, m), 1.93 (1H, m), 2.07 (1H, m), 3.37-3.30 (4H, m), 3.42 (3H, s), 3.70 (1H, br s), 4.13 (1H, br s), 4.99 (1H, br s), 5.45 (1H, dd, J=5.2 Hz, 16.0 Hz), 5.75 (1H, br s), 6.43 (1H, d, J=16.0 Hz), 7.20 (2H, m), 7.63 (2H, m)

Example 7

(Production of n-propylamine Salt)

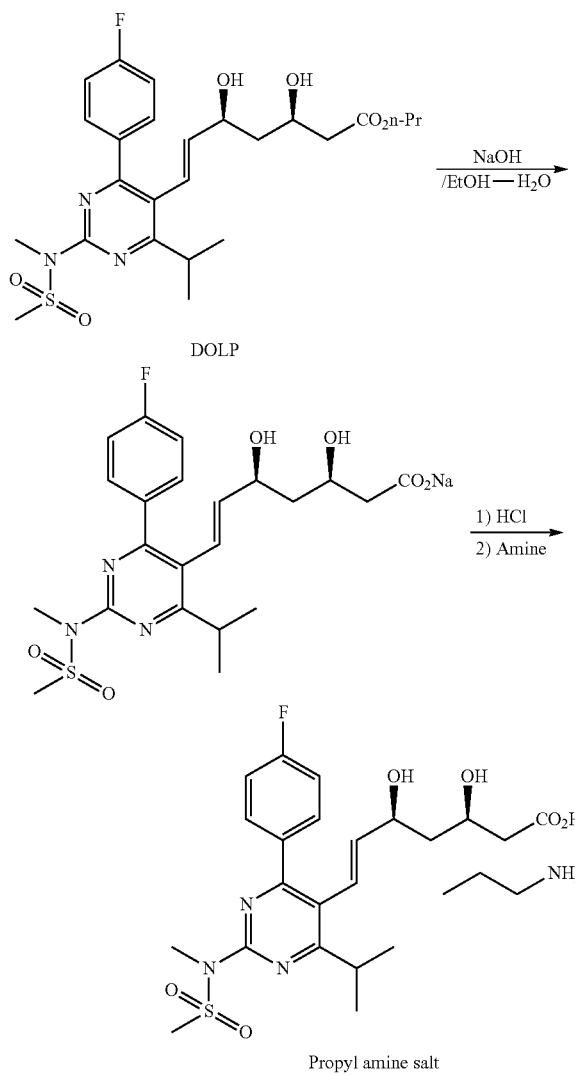

Propyl amine salt

DOLP (1 g, 1.91 mmol, purity: 99.1 area %), tert-butyl methyl ether (4.41 g) and water (10.0 g) were charged in a test tube. To the mixture was added dropwise 2 mol/L aqueous sodium hydroxide solution (1.17 g, 2.13 mmol) at room temperature. After stirring for 4 hr, the mixture was stood to allow for a partitioning operation. To the obtained organic layer was added 1 mol/L hydrochloric acid (2.5 g) to acidify the reaction system. To the mixture was added ethyl acetate (9.0 g) to allow for a partitioning operation. The obtained organic layer was washed twice with 2 wt % aqueous sodium hydroxide solution (10 g). A part of the organic solvent was evaporated under reduced pressure, and the liquid volume was adjusted to the total volume of 10 mL.

A solution (5 mL) of n-propylamine (136 mg, 2.3 mmol) in ethyl acetate was added dropwise to the aforementioned solution. To the obtained mixed solution was added a seed crystal of n-propylamine salt, and the mixture was cooled to an inside temperature of 5° C., and the precipitated crystals of n-propylamine salt were collected by filtration. The obtained crystals were dried in vacuo at an outer temperature of 40° C. As a result of HPLC analysis, the weight of the obtained n-propylamine salt was 0.90 g and the purity was 99.9 area %.

Figure 5:
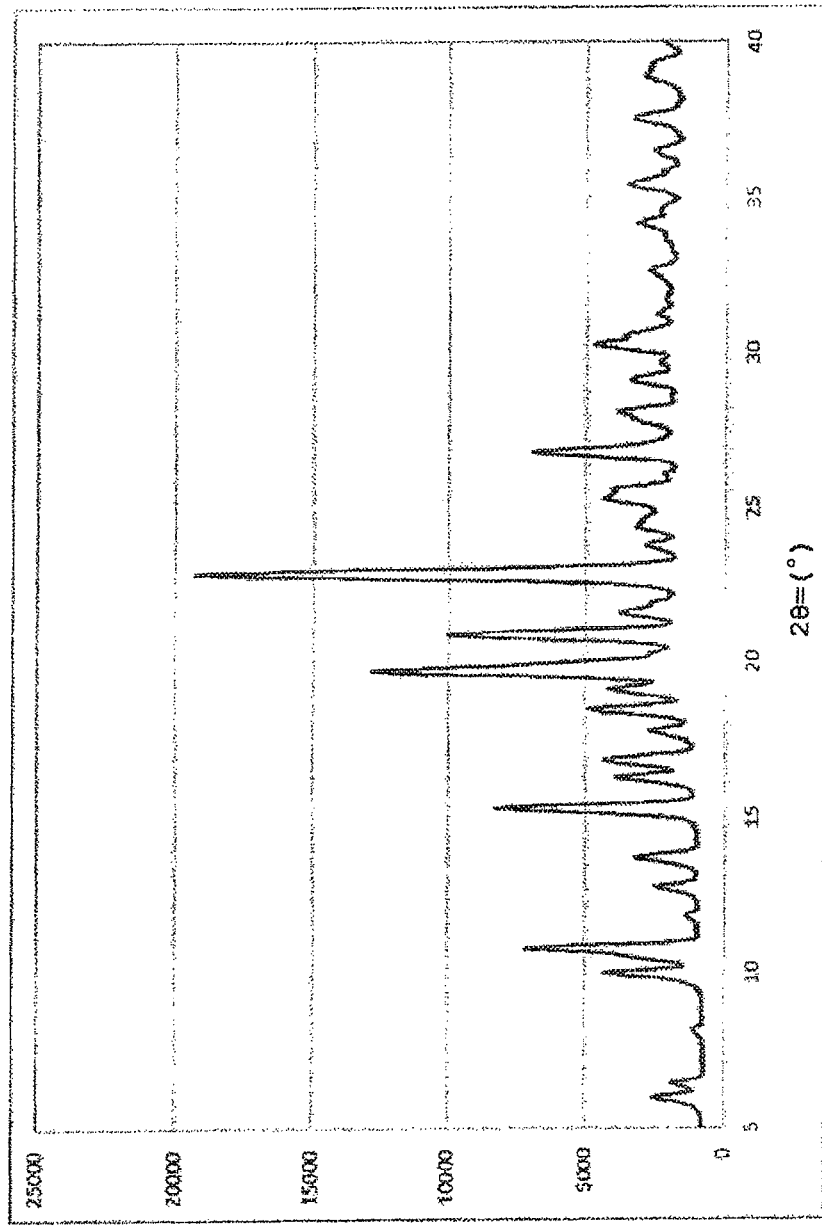
FIG. 5 shows the powder X-ray diffraction pattern of the propylamine salt obtained in Example 7, wherein the vertical axis shows intensity and the horizontal axis shows 2θ (°).

The powder X-ray diffraction spectrum of the obtained crystals of n-propylamine salt is shown in FIG. 5.

(Production of Seed Crystal of n-propylamine Salt)

Under a nitrogen atmosphere, DOLE (ethyl (3R), (5S), (6E)-7-[4-(4-fluorophenyl)-6-isopropyl-2-[methyl(methylsulfonyl)amino]pyrimidin-5-yl]-3,5-dihydroxy-6-heptenoate) (100 mg, 0.002 mmol), ethanol (2.07 g) and water (2 g) were charged in a test tube. After stirring at room temperature, 2 mol/L aqueous sodium hydroxide solution (0.16 mL) was added. After stirring at room temperature for 2 hr, ethanol was evaporated under reduced pressure. The recovered aqueous layer was extracted twice with ethyl acetate, ethyl acetate was added again, and the mixture was adjusted to pH 5 with 1 mol/L hydrochloric acid. The aqueous layer was removed by a partitioning operation, and the solvent was evaporated. To the obtained residue was added acetonitrile (1 mL), and 10 wt % aqueous n-propylamine solution (139 mg) was added dropwise. The mixture was stood at an outer temperature of 5° C. for two nights, and the precipitated crystals were collected by filtration and dried under reduced pressure to give n-propylamine salt (0.04 g).

Example 8

(Production of RSV-Ca)

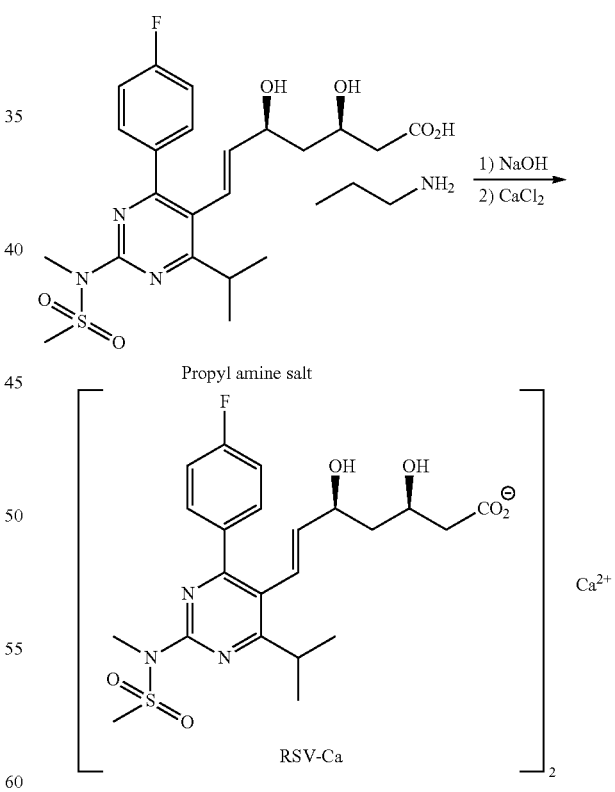

Water (6 mL) and 2 mol/L aqueous sodium hydroxide solution (0.81 mL, 1.63 mmol) were added to n-propylamine salt (800 mg, 1.48 mmol, HPLC purity: 99.9 area %). After stirring for 1 hr, to the reaction mixture was added dropwise a solution of calcium chloride (239 mg) in water (2 mL). After dropwise addition, the inside temperature was cooled to 5° C., and the precipitated crystals were collected by filtration. The obtained crystals were dried in vacuo at an outer temperature of 40° C. As a result of HPLC analysis, the weight of the obtained RSV-Ca crystals was 0.69 g and the purity was 99.9 area %.

Example 9

(Production of Dimethylamine Salt)

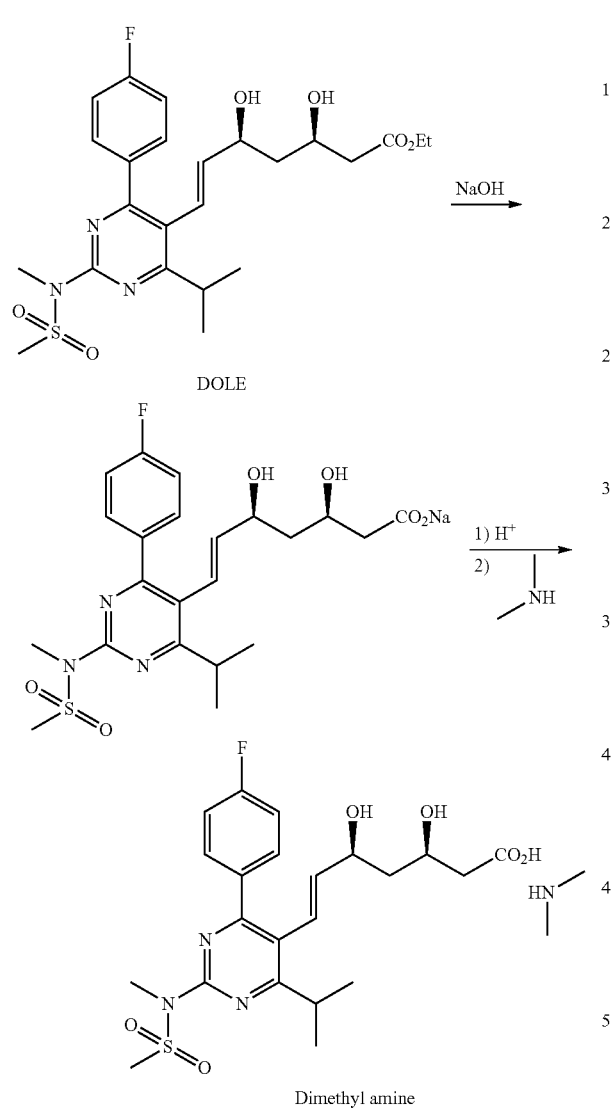

Under a nitrogen atmosphere, DOLE (100 mg, 0.002 mmol), ethanol (2.07 g) and water (2 g) were charged in a test tube. The mixture was stirred at room temperature, and 2 mol/L aqueous sodium hydroxide solution (0.16 mL) was added. After stirring for 2 hr, ethanol was evaporated under reduced pressure. The recovered aqueous layer was extracted twice with ethyl acetate, ethyl acetate was added again, and the mixture was adjusted to pH 5 with 1 mol/L hydrochloric acid. The aqueous layer was removed by a partitioning operation, and the solvent was evaporated. To the obtained residue was added acetonitrile (1 mL), and 10 wt % aqueous dimethylamine solution (212 mg) was added dropwise. The precipitated crystals were collected by filtration and dried under reduced pressure to give dimethylamine salt (0.03 g).

Figure 6:
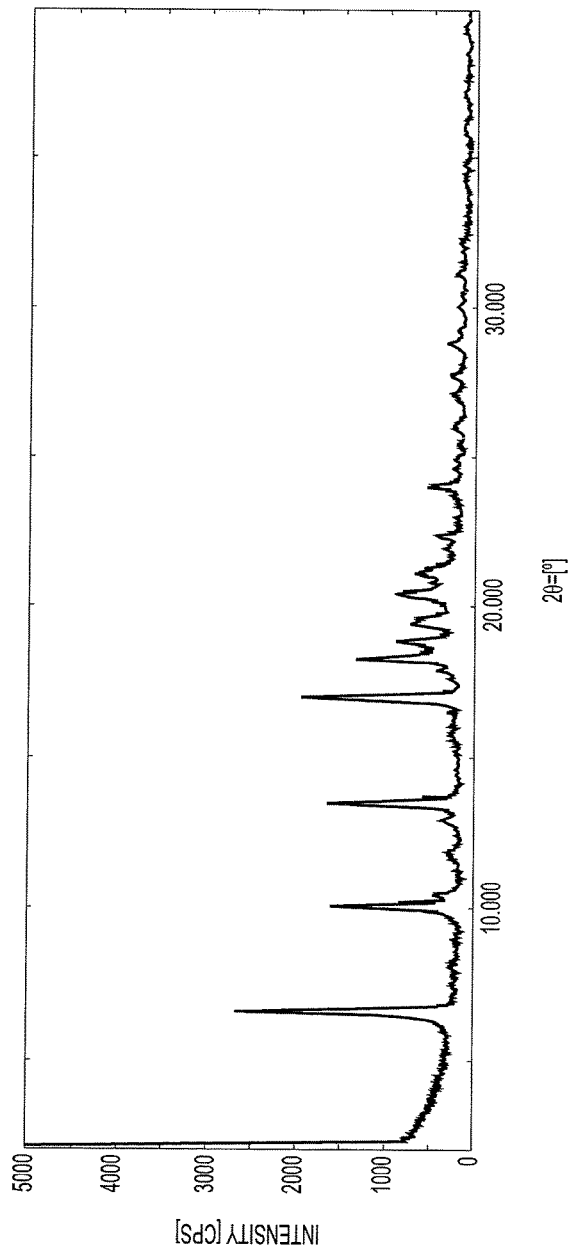
FIG. 6 shows the powder X-ray diffraction pattern of the dimethylamine salt obtained in Example 9, wherein the vertical axis shows intensity and the horizontal axis shows 2θ (°).

The powder X-ray diffraction spectrum of the obtained crystals of dimethylamine salt is shown in FIG. 6.

Example 10

(Production of RSV-Ca)

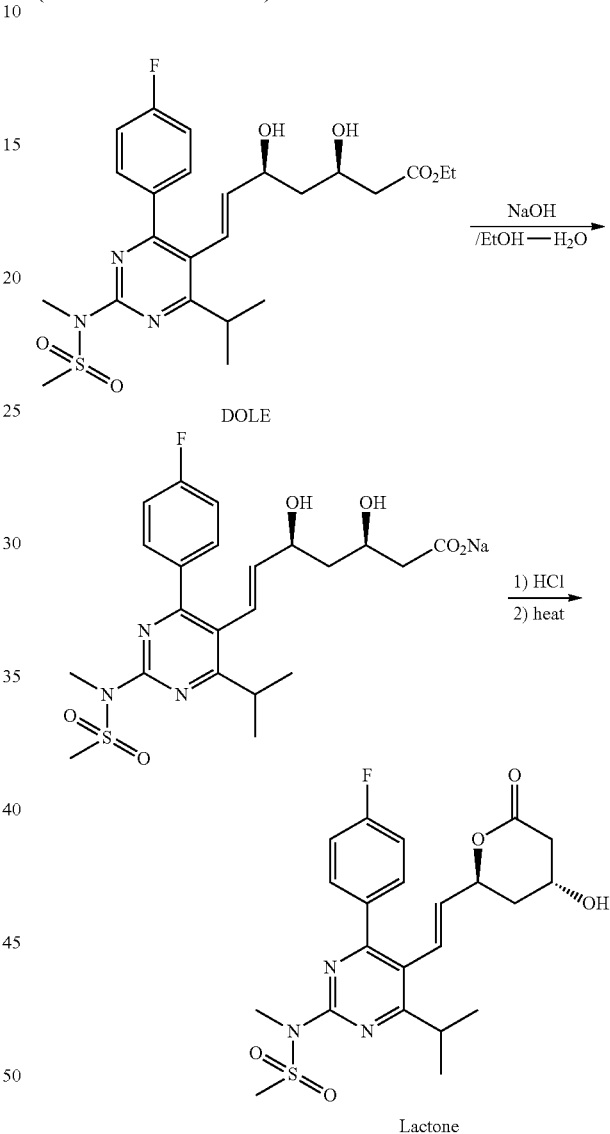

DOLE (net amount 0.5 g, 0.98 mmol, purity 92.8 area %), ethanol (9.24 g) and water (10 g) were added into a test tube. Thereto was added 1 mol/L aqueous sodium hydroxide solution (1.1 mL, 1.1 mmol) at 25° C. After stirring for 3 hr, the reaction mixture was concentrated under reduced pressure at 40° C. Thereafter, water (10 g) and ethyl acetate (2.28 g) were added to allow for partitioning. This operation was repeated twice. To the obtained aqueous layer were added ethyl acetate (10 g) and 1 mol/L hydrochloric acid (1 L). After partitioning, to the obtained aqueous layer was added ethyl acetate, and the mixture was partitioned again. The obtained organic layer was concentrated, and toluene (17.2 g) was added. Toluene (8.6 g) was concentrated under reduced pressure at an outer temperature of 40° C., and the concentrated product was heated to an inside temperature of 110° C. This temperature was maintained for 6 hr, and the mixture was cooled to an inside temperature of 5° C. The precipitated crystals were collected by filtration to give a lactone form (0.35 g). As a result of HPLC analysis, the purity of the obtained lactone form was 96.4 area %.

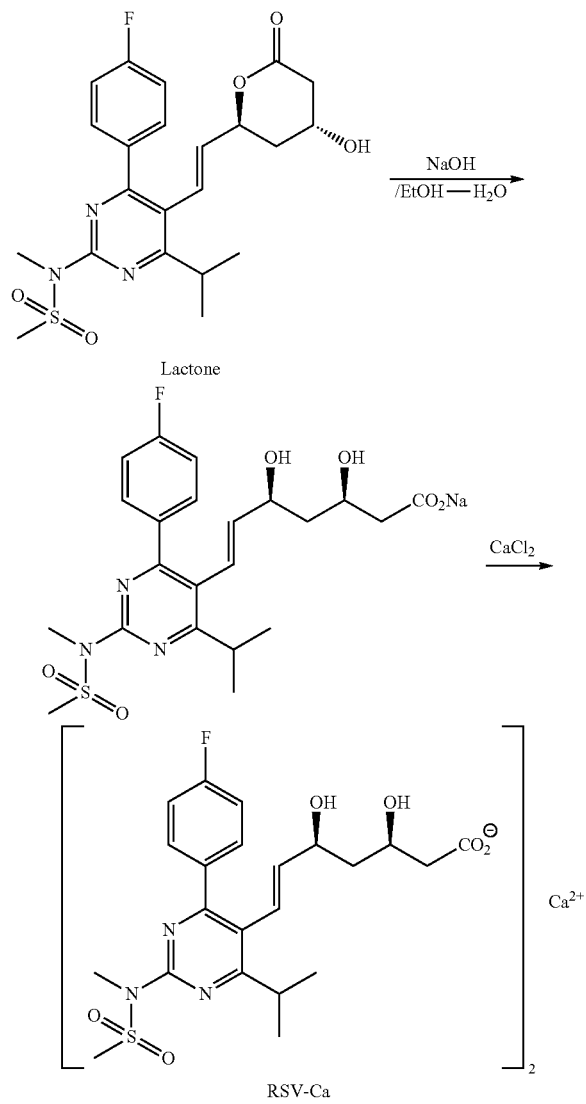

The obtained lactone form (0.2 g), ethanol (9.3 g) and water (10.6 g) were charged in a test tube, and 1 mol/L aqueous sodium hydroxide solution (0.3 g) was added. After completion of the reaction, the reaction mixture was concentrated under reduced pressure at an outer temperature of 40° C. To the obtained solution was added ethyl acetate (2.3 g) to allow for partitioning. This operation was repeated twice. The obtained aqueous layer was concentrated under reduced pressure at an outer temperature of 40° C. To the recovered solution was added water (1 g), and 0.17 mol/L aqueous calcium chloride solution (3.2 g) was added. The reaction mixture was stirred at an inside temperature of 10° C., and the precipitated crystals were collected by filtration. The obtained crystals were dried under reduced pressure at an outer temperature of 40° C. As a result of HPLC analysis, the weight of the RSV-Ca crystals was 0.8 g, and the purity was 98.2 area %.

Example 11

(Production of DOLP)

Ion exchange water (200 L), aqueous glucose (110.94 kg), dipotassium hydrogen phosphate (2.13 kg) and potassium dihydrogen phosphate (4.25 kg) were charged in a 1 m$^3$ reaction tank and dissolved therein. Then, frozen cells (52.7 kg) of recombinant *Escherichia coli* JM109/pKV32OCR1-GDH and NADP$^+$ (0.144 kg) dissolved in ion exchange water (3 L) were charged therein to give a suspension. Thereto was added a solution of DOXP (10.0 kg, 19.2 mol) obtained in Example 2 in DMSO (96.0 kg) was added, and the mixture was stirred at an inside temperature of 45° C.-52° C. for 6 hr. During the reaction, 1N aqueous sodium hydroxide solution was added dropwise to maintain pH 6.0. After completion of the reaction, the mixture was adjusted to pH 5.0 with 98 wt % sulfuric acid, and the mixture was stirred at an inside temperature of 65° C. for 1 hr. The HPLC purity of DOLP after stirring was 92.60 area %.

The reaction mixture was centrifuged, and precipitate consisting of the cells and reaction resultant product was obtained. The obtained precipitate was suspended in 20% aqueous methanol solution (502 L) and centrifuged.

(Extraction of DOLP)

The precipitate obtained by the above-mentioned method was suspended in 5 wt % aqueous sodium sulfate solution (105.3 kg), and extracted three times with ethyl acetate. The obtained extracts were mixed, and concentrated under reduced pressure. The obtained concentrate was washed with 4 wt % aqueous sodium sulfate solution (104 kg), and the obtained organic layer was filtered, and concentrated again under reduced pressure. The obtained ethyl acetate solution of DOLP was 132.8 kg, and the content of DOLP was 7.0 kg (recovery rate 70.0%, HPLC purity 94.13 area %).

(Crystallization of DOLP)

The ethyl acetate solution of DOLP (containing 6.7 kg of DOLP) obtained by the above-mentioned method was concentrated under reduced pressure. To the obtained residue was added 1-propanol (51.5 kg), and the mixture was concentrated again under reduced pressure. After concentration, water (25.6 kg) was added, and the temperature was cooled to 10° C. The seed crystal of DOLP was added to allow for precipitation of crystals, and water (12.8 kg) was added. The precipitated crystals were recovered by solid-liquid separation. The purity of the obtained DOLP was 98.80 area %. The next crystallization was performed without drying.

Under a nitrogen atmosphere, toluene (48.1 kg) was added to the wet crystals of DOLP. The mixture was heated to 45° C., and the aqueous layer was removed by partitioning. After partitioning, the mixture was concentrated under reduced pressure. The temperature was adjusted to 40° C., the seed crystal of DOLP was added and DOLP was precipitated. After cooling to 0° C., the crystals were recovered by solid-liquid separation. The crystals were washed with toluene (2.4 kg) cooled to 5° C. in advance. The purity of the obtained DOLP was 98.87 area %, and the next crystallization was performed without drying.

Under a nitrogen atmosphere, toluene (31.7 kg) was added to the wet crystals of DOLP. The mixture was heated to 62° C. to dissolve DOLP. The solution was cooled to 40° C., and the seed crystal (5.2 g) of DOLP was added to allow for crystallization. Thereafter, toluene (9 kg) was added. After cooling to 0° C., the crystals were recovered by solid-liquid separation. The crystals were washed with toluene (2.2 kg) cooled to 5° C. in advance. The purity of the obtained DOLP was 99.58 area %, and the next crystallization was performed without drying.

Figure 4:
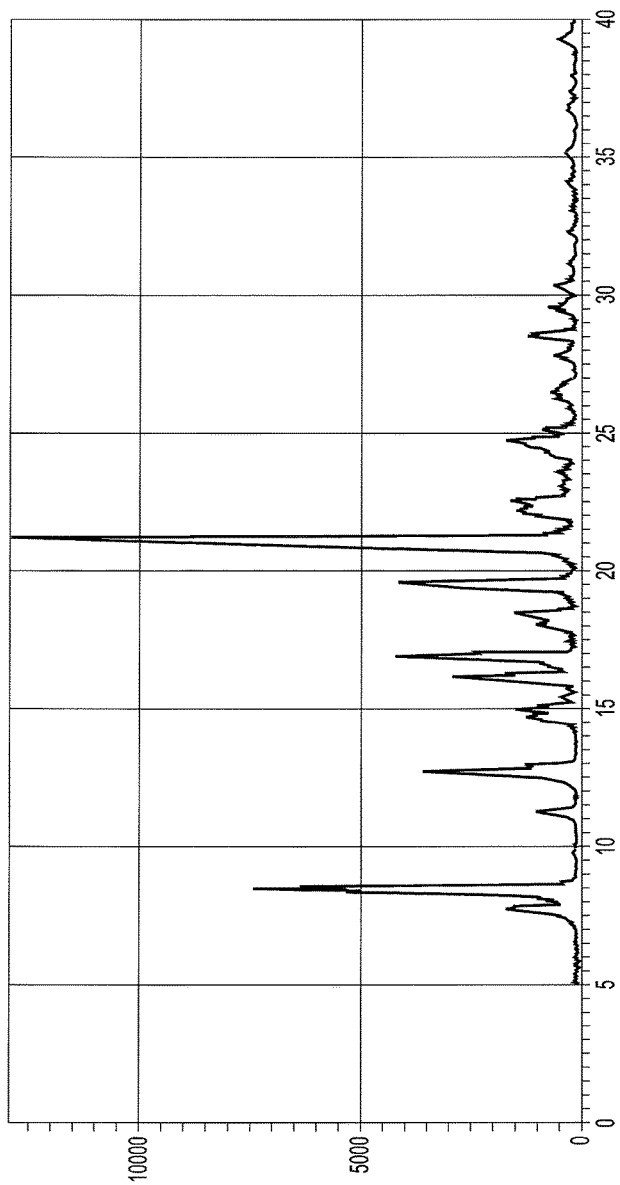
FIG. 4 shows the powder X-ray diffraction pattern of the compound (DOLP) obtained in Example 11, wherein the vertical axis shows intensity and the horizontal axis shows 2θ (°).

The above-mentioned method was repeated twice, and the obtained crystals were dried under reduced pressure and recovered. The weight of DOLP after drying was 3.41 kg (total recovery yield 48%) and the purity was 99.86 area %. The results of the powder X-ray diffraction of the obtained crystals are shown in FIG. 4 and Table 8.

TABLE 8

| 2θ | relative intensity |
|---|---|
| 7.7 | 13 |
| 8.4 | 57 |
| 11.2 | 8 |
| 12.7 | 28 |
| 12.9 | 10 |
| 14.7 | 10 |
| 15.0 | 12 |
| 16.1 | 23 |
| 16.9 | 33 |
| 18.0 | 8 |
| 18.4 | 12 |
| 19.5 | 33 |
| 21.1 | 100 |
| 22.2 | 12 |
| 22.5 | 13 |
| 23.6 | 5 |
| 24.2 | 5 |
| 24.5 | 10 |
| 24.7 | 14 |
| 25.1 | 7 |
| 26.5 | 6 |
| 27.8 | 5 |
| 28.6 | 10 |
| 29.6 | 6 |
| 30.4 | 5 |
| — | — |
| — | — |

Example 12

Under a nitrogen atmosphere, DOLP (2.99 kg, 5.71 mol) obtained in Example 11 and methyl t-butyl ether (11.1 kg) were charged in a reaction vessel, and desalting water (29.0 kg) was added. To the obtained slurry was added dropwise 2 mol/L aqueous sodium hydroxide solution (3.47 kg, 6.42 mol) at an inside temperature of 25-28° C. over 10 min. After stirring for 3.5 hr, the mixture was partitioned and methyl t-butyl ether (11.1 kg) was added to the obtained aqueous layer. The obtained solution was stirred for 30 min, and the organic layer was separated and removed again, and the aqueous layer was concentrated under reduced pressure to a liquid amount of 24 L. The obtained solution was adjusted to an inside temperature of 25-28° C., and 10% aqueous calcium chloride solution (6.92 kg, 6.22 mmol) was added dropwise over 1 hr. The obtained slurry was stirred at an inside temperature of 25-28° C. for 1 hr, cooled to 0-5° C., aged at the same temperature for 140 min and the precipitated crystals were collected by filtration. The recovered crystals were dried under reduced pressure at 40° C.

The obtained crystals (2.14 kg, yield 75%) contained 2.9% of moisture. As a result of analysis by HPLC, the chemical purity of the obtained rosuvastatin calcium (RSV-Ca) crystals was 99.93 area %, and the optical purity was 100% e.e. The crystals contained 20 ppm of a compound represented by the following formula (11):

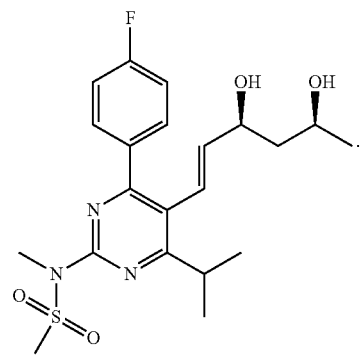

(11)

Example 13

(Production of RSV-Ca)

Under a nitrogen atmosphere, DOLP (10 g, 19.1 mmol) produced according to the method described in Example 11, methyl t-butyl ether (50 mL) and water (100 g) were mixed. To the obtained mixture was added dropwise 2 mol/L aqueous sodium hydroxide solution to adjust the mixture to pH 12-13. After stirring, the mixture was partitioned. To the obtained aqueous layer was added methyl t-butyl ether. After stirring, the mixture was partitioned, and methyl t-butyl ether contained in the obtained aqueous layer was evaporated by concentration under reduced pressure. To the obtained solution was added 0.2N aqueous acetic acid solution to adjust the mixture to pH 6-7. Thereafter, 1 mol/L calcium acetate solution was added dropwise, and the mixture was cooled. The precipitated crystals were collected by filtration and dried.

The obtained crystals (8.85 g, 92%) contained 1.9% of moisture. As a result of analysis by HPLC, the chemical purity of the obtained rosuvastatin calcium (RSV-Ca) crystals was 99.92 area %.

Example of the production method and purification method of the present invention are shown below.

For the quantitative analysis in the Examples, HPLC (High Performance Liquid Chromatography) was used and the measurement was performed under the following conditions.

<Chemical Purity of MoSi and DiSi>

Column: HP-5 (0.32 mm×30 m, film thickness 0.25 μm) manufactured by Agilent Technologies Temperature: 45° C. (0 min)→(20° C./min)→240° C. (5 min)

Inlet temperature: 250° C.

Detector temperature: 250° C.

Column flow rate: 1.5 mL/min (helium) Spirit ratio: 20:1

Detector: FID

<Chemical Purity of DOXP>

The measurement was performed under the same conditions as those described above.

<Chemical Purity of 5-MOLP and DOLP>

Column: Capcell Pak C18 MGIII-H (2.0 mm×100 mm, 3 μm) manufactured by Shiseido Co., Ltd.

Mobile phase: A: 0.1 M ammonium acetate/ethanol=3/2 (mL/mL) B: 0.1 M ammonium acetate/ethanol=1/4 (mL/mL)

Gradient program (B concentration): 0% (0 min)→0% (10 min)→100% (25 min)→100% (30 min)

Flow rate: 0.3 mL/min Column temperature: 40° C.

Detection wavelength: UV 245 nm

<Analysis of DENK in RSV-Ca>

Column: Cadenza CD-C18 (4.6 mm×250 mm, 3 μm) manufactured by Imtakt Inc.

Mobile phase: A: 0.1% aqueous formic acid solution B: methanol containing 0.1% formic acid Gradient program (B concentration): 60% (0 min)→75% (12 min)→100% (20 min)

Flow rate: 0.8 mL/min Column temperature: 40° C.

Detector: MS (polarity: positive mode: SIM fragmentor: 200 dry gas flow: 5 L/min nebulizer: 40 psi dry gas temperature: 250° C. vaporizer temperature: 150° C.)

Reference Example 4

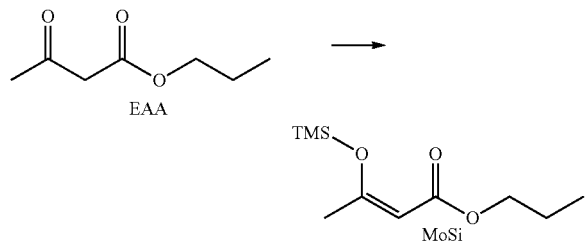

Under a nitrogen atmosphere, propyl acetoacetate (EAA) (75.4 g, 523 mmol) and n-heptane (518.1 g) were charged in a 1 L flask. The inside temperature was adjusted to 20° C., and triethylamine (58.2 g, 575 mmol) was added. Thereafter, the inside temperature was cooled to 10° C., and trimethylsilyl chloride (61.4 g, 564 mmol) was added dropwise over 40 min. Thereafter, the inside temperature was adjusted to 20° C., and the mixture was stirred for 1.5 hr. The resulting crystals were collected by filtration, and washed with 257 g of n-heptane. The obtained mother liquor was concentrated under reduced pressure at an outer temperature of 40° C. The weight of the obtained MoSi was 110.5 g, and the purity by GC was 99.1 area % containing 2.8% of n-heptane.

Reference Example 5

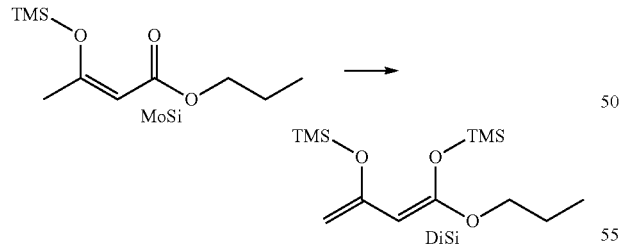

Under a nitrogen atmosphere, diisopropylamine (52.9 g, 522 mmol) and THF (244 g) were charged in a 2 L flask. The inside temperature was cooled to −25° C., a solution (200 ml) of 2.5 M n-butyllithium in n-hexane was added dropwise over 30 min. After the completion of the dropwise addition, the inside temperature was cooled to −73° C. Thereafter, a solution of MoSi (106.4 g) obtained in Reference Example 4 in THF (104 g) was added dropwise over 1 hr. After the completion of the dropwise addition, a solution of trimethylsilyl chloride (61.9 g, 570 mmol) in THF (69.8 g) was added dropwise over 40 min. The reaction mixture was warmed to room temperature, and concentrated under reduced pressure at an outer temperature of 20° C. The resulting crystals were collected by filtration, and the crystals were washed with n-heptane (132 g), and concentrated again under reduced pressure at an outer temperature of 20° C. The weight of the obtained DiSi was 144.1 g, and the purity by GC was 78.3 area %, containing 2% n-hexane, 0.1% THF, 0.16% n-heptane.

Reference Example 6

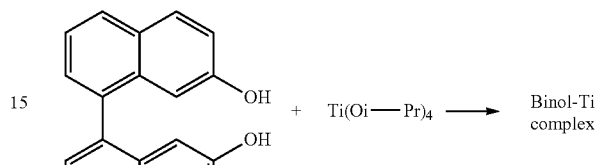

(S)-BINOL

Under a nitrogen atmosphere, methylene chloride (45 ml) and molecular sieves 4A (1 g) and (S)-1,1'-bi-2-naphthol ((S)-BINOL) (1 g) were charged in a 100 mL flask. Titanium tetraisopropoxide (1 g) was added dropwise at ambient temperature. The mixture was stirred for 2.5 hr, filtered and concentrated under reduced pressure at ambient temperature. The weight of the obtained residue was 1.59 g, which was directly used in the next reaction without purification.

Reference Example 7

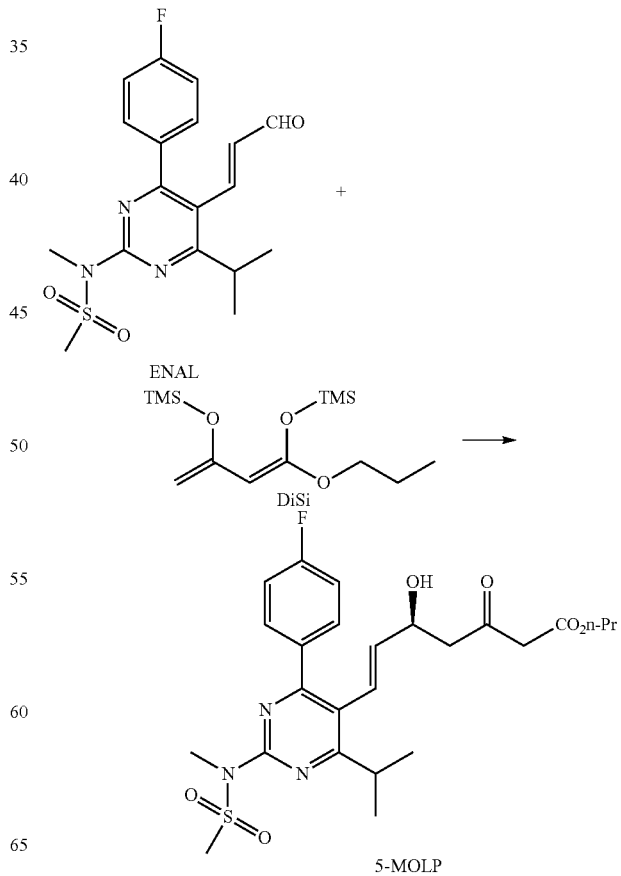

Under a nitrogen atmosphere, ENAL (5 g, 13.25 mmol), the catalyst (0.21 g) prepared in Reference Example 6, lithium chloride (0.2 g, 4.7 mmol) and THF (75 ml) were charged in a 300 mL flask. Tetramethylethylenediamine (1.46 g, 12.6 mmol) was added at an inside temperature of 27° C. After stirring at the same temperature for 1.5 hr, a solution of DiSi (10.3 g) prepared in Reference Example 5 in THF (5 ml) was added dropwise over 30 min. After stirring at the same temperature for 17 hr, the inside temperature was cooled to 12° C. and a mixed solution of 98% sulfuric acid (2.65 g) and water (22.1 g) was added. After stirring for 10 min, the mixture was stood to allow for partitioning. The obtained organic layer was washed with 5% aqueous sodium hydrogen carbonate solution (9.3 g) and then with saturated brine (10.4 g), and dried over magnesium sulfate (4.3 g). After filtration, the obtained mother liquor was concentrated under reduced pressure at an outer temperature of 43° C. The residue was purified by silica gel column chromatography (eluent: n-heptane and ethyl acetate). The fraction containing the object product was concentrated to give 5-MOLP (5.8 g). The purity of the obtained 5-MOLP by HPLC was 86.8 area %.

Reference Example 8

Under a nitrogen atmosphere, 5-MOLP (0.1 g) synthesized by the method of Reference Example 7, methyl t-butyl ether (1 mL) and water (1 mL) were charged. 2N aqueous sodium hydroxide solution (0.11 g) was added at ambient temperature. After stirring overnight at ambient temperature, and the mixture was stood and the aqueous layer and the organic layer were separated. The obtained aqueous layer was heated to an outer temperature of 80° C., and stirred for 13 hr. After completion of the reaction, the mixture was cooled to room temperature, and methyl t-butyl ether (2 ml) was added to allow for partitioning. The obtained organic layer was concentrated under reduced pressure at ambient temperature. The residue was analyzed to find that DENK was contained at a purity of 93.5 area % by HPLC analysis.

$^1$H-NMR of the obtained DENK is shown below.

$^1$H-NMR (400 MHz, CDCl$_3$) δ 1.30 (6H, d, J=6.4 Hz), 1.80 (1H, m), 2.30 (3H, s), 3.52 (3H, s), 3.59 (3H, s), 6.08 (1H, d, J=16.4 Hz), 6.22 (1H, m), 7.15 (4H, m), 7.65 (2H, m)

Example 14

(Production of DOXP)

Using DHAB produced by the same method as in the aforementioned Reference Example 1 and by the same method as in the aforementioned Example 2, DOXP was produced.

(Preparation of Cells)

Cells were prepared by the same method as in the aforementioned Reference Example 3 to give recombinant *Escherichia coli* JM109/pKV32OCR1-GDH.

(Synthesis of DOLP)

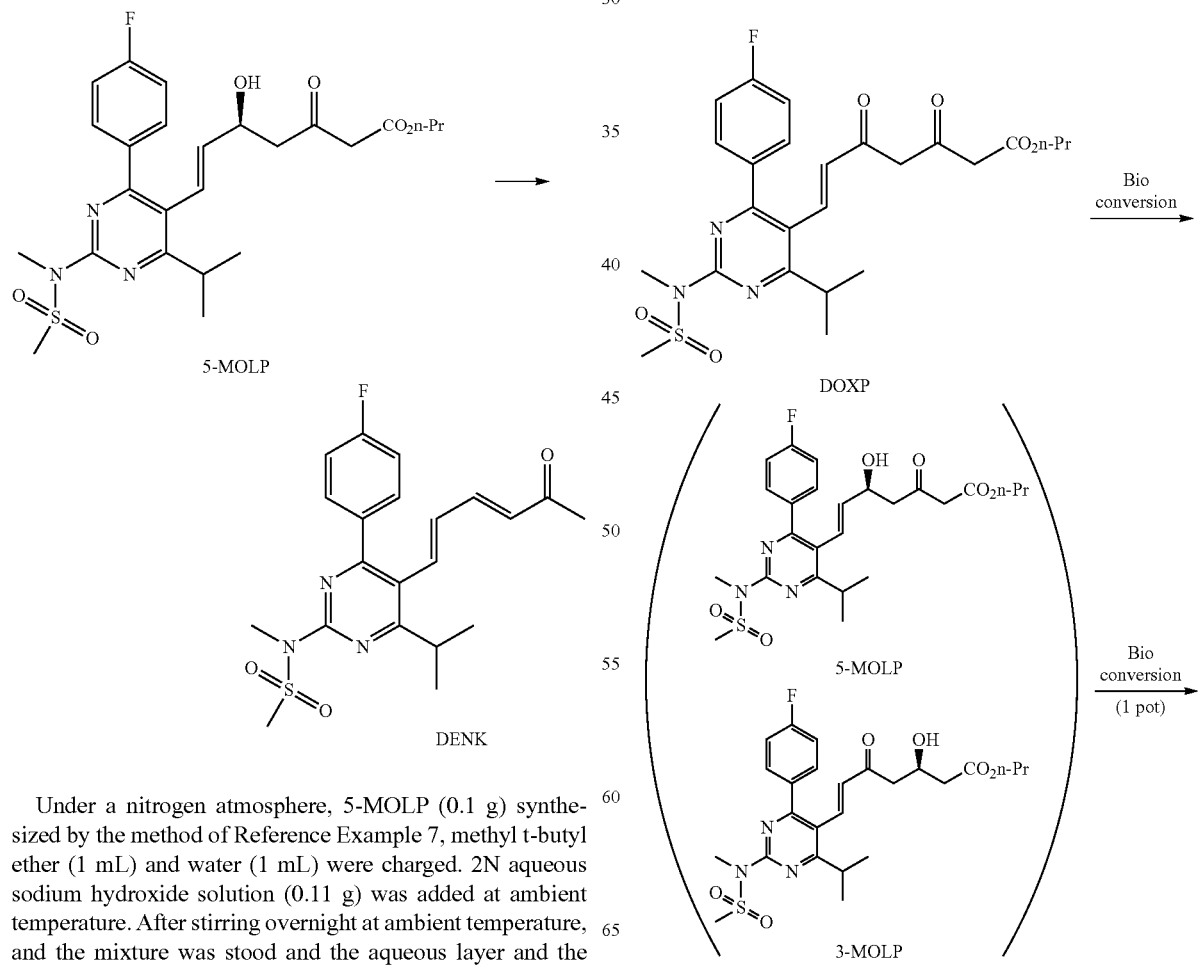

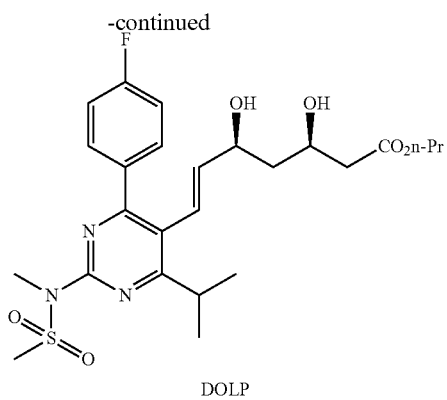

DOLP (1) Biological Reaction

Ion exchange water (900 mL), aqueous glucose (212.5 g), dipotassium hydrogen phosphate (18.5 g), potassium dihydrogen phosphate (31.0 g) and glycerol (480.0 g) were charged in a 5 L reaction tank and dissolved therein. Then, the frozen cells (202.4 g) of the recombinant *Escherichia coli* JM109/pKV32OCR1-GDH obtained above and NADP+ (552 mg) were charged and suspended therein. DOXP (57.6 g, 110.81 mmol) obtained above was dissolved in DMSO (496.8 g) and the solution was added to a suspension of the above-mentioned cells. The mixture was stirred for 6 hr while maintaining pH 6.0 by adding dropwise a 24% aqueous sodium hydroxide solution at an inside temperature of 45° C.-52° C. After completion of the reaction, the mixture was adjusted to pH 5.0 with 98% sulfuric acid, and the mixture was stirred at an inside temperature of 65° C. for 1 hr. The HPLC purity of the obtained DOLP was 92.0 area %, containing 5.1 area % of 5-MOLP.

The obtained reaction mixture was centrifuged, and precipitate consisting of the cells and reaction resultant product was obtained. The obtained precipitate was further suspended in 20% aqueous methanol solution (11.5 kg) and centrifuged.

(2) DOLP Extraction

The precipitate obtained above and sodium chloride (230 g) were suspended in acetone (1.72 kg) and solid-liquid separation was performed.

(3) DOLP Crystallization

A solution of the obtained DOLP in acetone was concentrated under reduced pressure. To the obtained residue was added 1-propanol (973 g), and the mixture was concentrated under reduced pressure. Water (192 g) was added, and the temperature was cooled to 5° C. to allow for crystal precipitation. Thereafter, water (96.9 g) was added and solid-liquid separation was performed. The obtained crystals were dried under reduced pressure. The weight of the crystals after drying was 45.9 g (yield 80%), and the purity was 98.80 area %, containing 1.5 area % of 5-MOLP.

To the crystals (DOLP) (35.0 g) obtained by the above-mentioned method was added toluene (242.2 g) under a nitrogen atmosphere. Thereafter, and the mixture was dissolved by heating to 62° C., the temperature was adjusted to around 42° C., and the seed crystal of DOLP was added. After stirring for 3.5 hr, toluene (60.5 g) was added. The temperature was cooled to 0° C., and the crystals were recovered by solid-liquid separation. The obtained crystals were dried under reduced pressure. The amount of DOLP after drying was 32.5 g (recovery yield 93%), and the purity was 99.3 area %, containing 0.4 area % of 5-MOLP.

To the obtained crystal (DOLP) (30 g) was added toluene (207.6 g) under a nitrogen atmosphere, and the mixture was heated to 61° C. to dissolve the crystals. The obtained solution was cooled to 40° C. to allow for crystallization. After aging for 1 hr, toluene (51.7 g) was added and the mixture was cooled to 0° C. and the crystals were recovered by solid-liquid separation. The obtained crystals were dried under reduced pressure. The amount of DOLP after drying was 28.3 g (recovery yield 94%), and the purity was 99.6 area %, containing 0.16 area % of 5-MOLP.

(Synthesis of RSV-Ca)

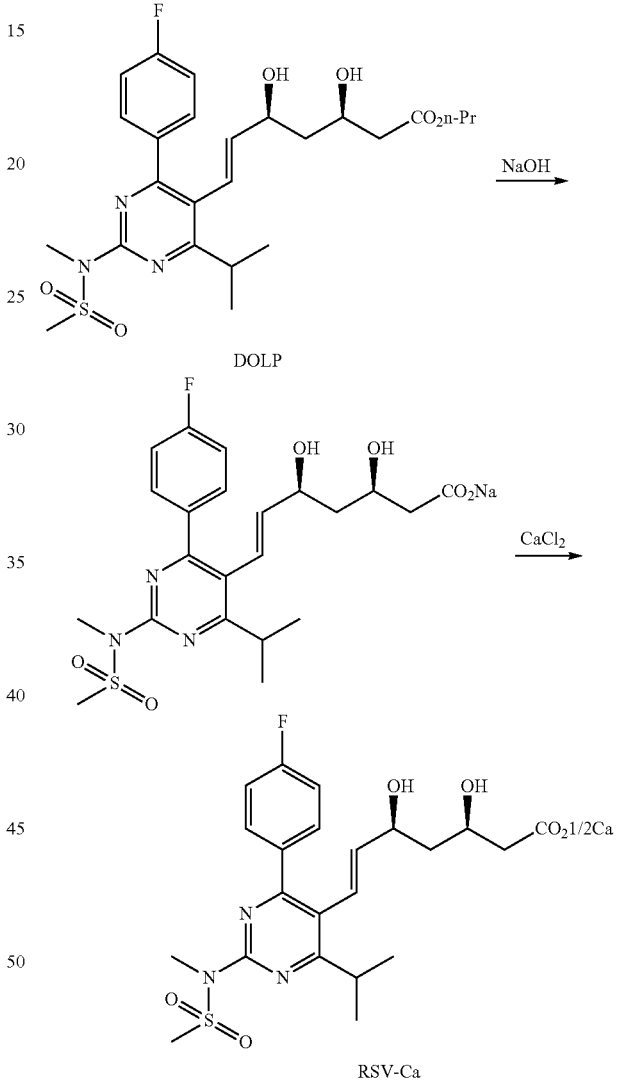

Under a nitrogen atmosphere, DOLP (10 g, 19.1 mmol) obtained by the above-mentioned method and methyl t-butyl ether (44.0 g) were charged in a reaction vessel, and desalting water (100 g) was added. Thereto was added dropwise 2 mol/L aqueous sodium hydroxide solution (10.4 g, 19.3 mmol) at an inside temperature of around 25° C. over 5 min. After stirring for 6 hr, the mixture was partitioned and the obtained aqueous layer was heated at an outer temperature of 80° C. After heating for 8 hr, methyl t-butyl ether (22.0 g) was added to the solution. The obtained solution was stirred for 10 min, the organic layer was separated and removed, and the aqueous layer was concentrated under reduced pressure to a liquid amount of 80 ml. The obtained solution was adjusted to an inside temperature of around 25° C., a solution of calcium acetate monohydrate (3.5 g) and desalting water (20 g) mixed in advance was added dropwise over 25 min. The obtained slurry was stirred at an inside temperature of around 25° C. for 1 hr, cooled to 0-5° C., and the precipitated crystals were collected by filtration. The recovered crystals were dried under reduced pressure at 40° C.

The obtained crystals were 8.8 g (yield 91%) and contained 0.9% of moisture. As a result of analysis by HPLC, the chemical purity of the obtained crystals of rosuvastatin calcium (RSV-Ca) was 99.95 area %, and contained 0.02 area % of a compound represented by the aforementioned formula (12), n-propyl 7-(4-(4-fluorophenyl)-6-isopropyl-2-(methanesulfonylmethylamino)pyrimidin-5-yl)-5-hydroxy-3-oxo-6-heptenoate (hereinafter "5-MOLA"), and 91 ppm of DENK. It is clear from the comparison with the analysis results of DOLP after drying that the content 5-MOLA decreased to $1/20$.

Example 15

(Purification of RSV-Ca)

Under a nitrogen atmosphere, rosuvastatin calcium (7.5 g) containing 5-MOLA (0.09 area %), methyl t-butyl ether (32.6 g) and water (22.2 g) were charged in a 500 ml flask, and 1N hydrochloric acid (15.8 g) was added and dissolved therein. The obtained solution was stirred for 2.5 hr and stood to allow for partitioning. Water (29.4 g) and 2N aqueous sodium hydroxide solution (8.4 g) were added to the obtained organic layer. After stirring for 10 min, the mixture was stood to allow for partitioning. The obtained aqueous layer was stirred for 34 hr with heating at an outer temperature of 80° C. Thereafter, the mixture was cooled to room temperature and extracted twice with methyl t-butyl ether (38 ml). The obtained aqueous layer was concentrated under reduced pressure at an outer temperature of 50° C. Thereafter, acetic acid was added to the concentrated solution to adjust pH in the system to 7.5. The outer temperature was set to 20° C., and a mixed solution of calcium acetate monohydrate (2.7 g) and water (14.8 g) was added dropwise over 30 min. Thereafter, the outer temperature was cooled to 0° C., and the precipitated crystals were collected by filtration. The recovered crystals were dried under reduced pressure at an outer temperature of 40° C.

The obtained crystals were 6.7 g (yield 89%) and contained 0.3% of moisture. As a result of analysis by HPLC, the chemical purity of the obtained crystals of rosuvastatin calcium (RSV-Ca) was 99.94 area %, and contained 0.02 area % of 5-MOLA. It is clear from the comparison with the analysis results of rosuvastatin calcium on charging that the content 5-MOLA decreased to $1/5$.

INDUSTRIAL APPLICABILITY

The present invention can provide a method of efficiently producing rosuvastatin calcium and intermediates therefor having a high purity, under economical conditions and at an industrial scale, without using an extremely low temperature reaction or an expensive asymmetric catalyst.

This application is based on patent application Nos. 2014-21769, 2014-209142 and 2014-209480 filed in Japan, the contents of which are incorporated in full herein.

What is claimed is:

1. A production method of a compound represented by the following formula (2):

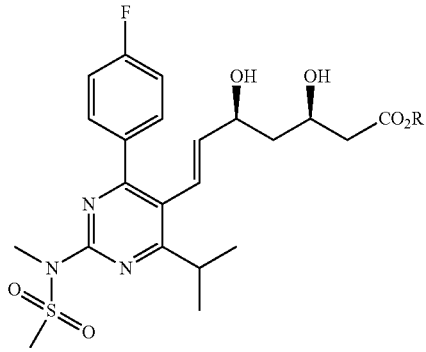

(2)

wherein R is a primary alkyl group having 1-8 carbon atoms or a secondary alkyl group having 3-6 carbon atoms, the method comprising:

(i) reducing a compound represented by the following formula (1a):

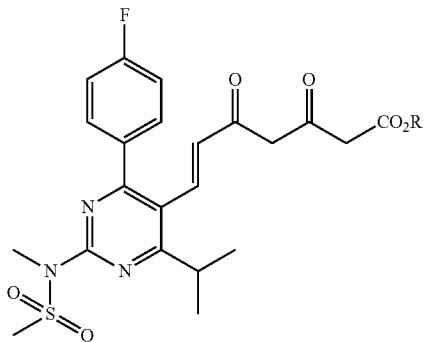

(1a)

wherein R is as defined for R in said formula (2), comprising reacting the compound with an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell;

wherein said enzyme comprises a polypeptide selected from:
(A) a carbonyl reductase (OCR1) polypeptide of SEQ ID NO: 2 from *Ogataea minuta* var. *nonfermentans* NBRC1473,
(B) a polypeptide consisting of an amino acid sequence having a homology of 90% or more to the amino acid sequence shown in SEQ ID NO: 2, and having an activity to convert a compound represented by said formula (1a) to a compound represented by said formula (2), and
(C) a polypeptide comprising an amino acid sequence which is the amino acid sequence shown in SEQ ID NO: 2, wherein 20 or less amino acids are substituted, deleted or added, and having an activity to convert a compound represented by said formula (1a) to a compound represented by said formula (2).

2. The production method according to claim 1, wherein the gene encoding said enzyme is a DNA comprising the base sequence selected from:
(D) the base sequence shown in SEQ ID NO: 1,
(E) a base sequence that hybridizes to a DNA consisting of a sequence complementary to the base sequence shown in SEQ ID NO: 1 under stringent conditions, and encodes a polypeptide having an activity to convert the compound represented by formula (1a) to the compound represented by formula (2), and
(F) the base sequence shown in SEQ ID NO: 1 wherein 60 or less bases are substituted, deleted or added, and encodes a polypeptide having an activity to convert the compound represented by formula (1a) to the compound represented by formula (2).

3. The production method according to claim 1, wherein (i) is performed in the presence of a polyhydric alcohol.

* * * * *